(12) United States Patent
Gronthos et al.

(10) Patent No.: US 12,275,801 B2
(45) Date of Patent: Apr. 15, 2025

(54) ISOLATION OF ADULT MULTIPOTENTIAL CELLS BY TISSUE NON-SPECIFIC ALKALINE PHOSPHATASE

(71) Applicants: Stan Gronthos, Adelaide (AU); Andrew Christopher William Zannettino, Highbury (AU); John Paul Simmons, Kew (AU)

(72) Inventors: Stan Gronthos, Adelaide (AU); Andrew Christopher William Zannettino, Highbury (AU); John Paul Simmons, Kew (AU)

(73) Assignee: MESOBLAST, INC., New York, NY (US)

( * ) Notice: Subject to any disclaimer, the term of this patent is extended or adjusted under 35 U.S.C. 154(b) by 875 days.

(21) Appl. No.: 16/867,252

(22) Filed: May 5, 2020

(65) Prior Publication Data

US 2020/0332023 A1    Oct. 22, 2020

Related U.S. Application Data

(60) Continuation of application No. 15/651,469, filed on Jul. 17, 2017, now abandoned, which is a continuation of application No. 15/167,934, filed on May 27, 2016, now Pat. No. 9,783,617, which is a division of application No. 14/621,470, filed on Feb. 13, 2015, now abandoned, which is a division of application No. 13/736,790, filed on Jan. 8, 2013, now abandoned, which is a continuation of application No. 11/918,593, filed as application No. PCT/AU2006/000494 on Apr. 12, 2006, now Pat. No. 8,367,405.

(60) Provisional application No. 60/670,250, filed on Apr. 12, 2005.

(51) Int. Cl.
| | |
|---|---|
| C12N 5/0775 | (2010.01) |
| A61K 35/12 | (2015.01) |
| C07K 16/40 | (2006.01) |
| C12N 5/00 | (2006.01) |
| C12N 5/16 | (2006.01) |
| C12Q 1/42 | (2006.01) |
| G01N 33/577 | (2006.01) |
| G01N 33/68 | (2006.01) |

(52) U.S. Cl.
CPC ............ *C07K 16/40* (2013.01); *C12N 5/0081* (2013.01); *C12N 5/0663* (2013.01); *C12N 5/163* (2013.01); *C12Q 1/42* (2013.01); *G01N 33/577* (2013.01); *G01N 33/68* (2013.01); *A61K 2035/124* (2013.01); *C07K 2317/76* (2013.01); *C12N 2533/56* (2013.01); *G01N 2333/916* (2013.01)

(58) Field of Classification Search
None
See application file for complete search history.

(56) References Cited

U.S. PATENT DOCUMENTS

| | | |
|---|---|---|
| 8,367,405 B2 | 2/2013 | Gronthos et al. |
| 9,783,617 B2 | 10/2017 | Gronthos et al. |
| 2002/0022676 A1 | 2/2002 | He et al. |
| 2018/0009905 A1 | 1/2018 | Gronthos et al. |

FOREIGN PATENT DOCUMENTS

| | | |
|---|---|---|
| JP | 2003-052365 | 2/2003 |
| WO | WO 1999/059500 A2 | 11/1999 |
| WO | WO 2002/016553 A2 | 2/2002 |
| WO | WO 2003/004605 A2 | 1/2003 |
| WO | WO 2004/025293 A2 | 3/2004 |

OTHER PUBLICATIONS

Gronthos et al., J Bone Miner Res. Jan. 1999; 14(1):47-56 (Year: 1999).*
International Search Report issued by the International Searching Authority (ISA/AU) on May 22, 2006 in connection with International Application No. PCT/AU2006/000494.
Hui, M-Z. et al. "Expression of tissue non-specific alkaline phosphatase stimulates differentiated behaviour in specific transformed cell populations". The Anatomical Record, 1996, vol. 244, pp. 423-436. See pp. 425-430.
MacGregor, G.R. et al. "Tissue non-specific alkaline phosphatase is expressed in both embryonic and extraembyronic lineages during mouse embryogenesis but is not required for migration of primordial germ cells". Development, 1995, vol. 121, pp. 1487-1496.
Kues, W.A. et al. "Isolation of murine and porcine fetal stem cells from somatic tissue". Biology of Reproduction, Apr. 2005 (published online Dec. 22, 2004), vol. 72, pp. 1020-1028.
Written Opinion of the International Searching Authority issued by the International Searching Authority (ISA/AU) on May 22, 2006 in connection with International Application No. PCT/AU2006/000494.
International Preliminary Report on Patentability issued by the International Bureau of WIPO dated May 22, 2006 in connection with International Application No. PCT/AU2006/000494.
Kawamura, et al. (1994), "Transdifferentiation of Pigmented Multipotent Epithelium During Morphallactic Development of Budding Tunicates", Int. J. Dev Biol, 38 :369-377.
Osyezka et al. (2002), "Multilineage Differentiation of Adult Human Bone Marrow Progenitor Cells Transduced With Human Papilloma Virus Type 16 E6/E7 Genes" Calcif Tissue Int, 71: 477-458.

(Continued)

*Primary Examiner* — Daniel C Gamett
(74) *Attorney, Agent, or Firm* — John P. White

(57) ABSTRACT

The present invention relates to the use of tissue non-specific alkaline phosphatase (TNAP) as a marker for identifying and/or isolating adult multipotential cells. The present invention also relates to cell populations enriched by methods of the present invention and therapeutic uses of these cells.

20 Claims, 24 Drawing Sheets
Specification includes a Sequence Listing.

(56) References Cited

OTHER PUBLICATIONS

Sobiesiak et al., (2010) "The Mesenchymal Stem Cell Antigen MSCA-1 Is Identical to Tissue Non-Specific Alkaline Phosphatase" Stem Cells and Development, 19: 669-677.

Vogel, et al. (2003) "Heterogeneity Among Human Bone Marrow-Derived Mesenchymal Stem Cells and Neural Progenitor Cells" Haematologica, 88:126-133.

Mi-Zhou Hui et al., (1996) "Expression of Tissue Non-Specific Alkaline Phosphatase Stimulates Differentiated Behaviour In Specific Transformed Cell Populations" Anatomical Record 244 (4) : 423-436.

Gronthos, et al. (1994) "The STRO-1+ Fraction of Adult Human Bone Marrow Contains The Osteogenic Precursors" Blood 84 (12) : 4164-4173.

Office Action issued Aug. 16, 2011 in connection with Japanese Patent Application No. JP 2008-505693.

Office Action issued Jul. 13, 2011 in connection with European Patent Application No. EP 1869165.

Office Action issued Oct. 10, 2011 in connection with Chinese Patent Application No. CN 200680020870.9.

Extended European Search Report issued by the European Patent Office on Nov. 17, 2008 in connection with European Patent Application No. 06 72 1376.

Gronthos S, et al. "The STRO-1+ Fraction of Adult Human Bone Marrow Contains the Osteogenic Precursors" Blood, American Society of Hematology, 1994, vol. 84, No. 12, pp. 4164-4173.

Hotton D, et al. "Differential Expression and Activity of Tissue-nonspecific Alkaline Phosphatase (TNAP) in Rat Odontogenic Cells in Vivo" The Journal of Histochemistry & Cytochemistry, 1999, vol. 47 (12) :1541-1552.

Magnusson P, et al. "Monoclonal Antibodies against Tissue-Nonspecific Alkaline Phosphatase" Tumor Biology, 2002, 23:228-248.

Hoshi K, et al. "Immunolocalization of tissue non-specific alkaline phosphatase in mice" Histochemistry and Cell Biology, 1997, 107(3) :183-191.

Djouad F, et al. "Transcriptional profiles discriminate bone marrow-derived and synovium-derived mesenchymal stem cells" Arthritis Research and Therapy, 2005, vol. 7, No. 6, pp. R1304-R1315.

Gronthos S, et al. "A Novel Monoclonal Antibody (STRO-3) Identifies an Isoform of Tissue Nonspecific Alkaline Phosphatase Expressed by Multipotent Bone Marrow Stromal Stem Cells" Stem Cells and Development, 2007, vol. 16, No. 6, pp. 953-963.

He et al., U.S. Patent Application Publication No. 2002-0022676 A1, published Feb. 21, 2002.

Office Action issued Sep. 4, 2012 in connection with Japanese Patent Application No. 2008-505693.

Kues et al. (2005) "Isolation of Murine and Porcine Fetal Stem Cells from Somatic Tissue," Biol. of Reproduct. 72:1020-28.

MacGregor et al. (1995) "Tissue non-specific alkaline phosphatase is expressed in both embryonic and extraembryonic lineages during mouse embryogenesis but is not required for migration of primordial germ cells," Development 121:1487-98.

Examination Report issued Apr. 17, 2013 in connection with Indian Patent Application No. 8562/DELNP/2007.

* cited by examiner

STRO-3 Antigen Expression (PE)

Figure 3

```
BLASTN 1.4.8MP [20-June-1995] [Build 16:33:28 Sep 5 1995]
Reference: Altschul, Stephen F., Warren Gish, Webb Miller, Eugene W. Myers,
and David J. Lipman (1990). Basic local alignment search tool. J. Mol.
Biol. 215:403-10.
Query= az4 (821 letters)
Database: Non-redundant PDB+GBupdate+GenBank+EMBLupdate+EMBL 534,094
sequences; 373,855,830 total letters.
Smallest Sum High    Probability
Sequences producing High-scoring Segment Pairs:  Score   P(N)        N
gb|H37944|H37944 yp47h08.r1 Homo sapiens cDNA clone 190551 5' similar to gb:X14174
ALKALINE PHOSPHATASE, TISSUE-NONSPECIFIC ISOZYME
PRECURSOR (HUMAN);. Length = 484 Plus Strand HSPs:
Score = 936 (258.6 bits), Expect = 3.0e-144, Sum P(5) = 3.0e-144
Identities = 188/189 (99%), Positives = 188/189 (99%), Strand = Plus / Plus Query:   123 CCGTGCTCCCACGCGCTTGTGCCTGGACGGACCCTCGCCAGTGCTCTGCGCAGGATTGGA 182
             ||||||||||||||||||||||||||||||||||||||||||||||||||||||||||||
Sbjct:    26 CTGTGCTCCCACGCGCTTGTGCCTGGACGGACCCTCGCCAGTGCTCTGCGCAGGATTGGA  85

Query:   183 ACATCAGTTAACATCTGACCACTGCCAGCCCACCCCCTCCCACCCACGTCGATTGCATCT 242
             ||||||||||||||||||||||||||||||||||||||||||||||||||||||||||||
Sbjct:    86 ACATCAGTTAACATCTGACCACTGCCAGCCCACCCCCTCCCACCCACGTCGATTGCATCT 145

Query:   243 CTGGGCTCCAGGGATAAAGCAGGTCTTGGGGTGCACCATGATTTCACCATTCTTAGTACT 302
             ||||||||||||||||||||||||||||||||||||||||||||||||||||||||||||
Sbjct:   146 CTGGGCTCCAGGGATAAAGCAGGTCTTGGGGTGCACCATGATTTCACCATTCTTAGTACT 205

Query:   303 GGCCATTGGCACCTGCCTTACTAACTCCTTAGTGCCAGAGAAAGAGAAAGACCCCAAGTA 262
             |||||||| ||||||||||||||||||||||||||||||||||||||||||||||||||
Sbjct:   206 GGCCATTGGACCTGCCTTACTAACTCCTTAGTGCCAGAGAAAGAGAAAGACCCCAAGTAC 265

Query:   263 CTGGCGAGACCAAGCGCAAGAGACACTGAAATATGCCCTNGGAGCTTCAGAAGCTCAAAT 422
             ||||||||||||||||||||||||||||||||||||||| ||||||||||||||||||||
Sbjct:   266 TNGCGGAGACCAAGCGCAAGAGACACTGAAATATGCCCTGGGAGCTTCAGAAGCTCAAAT 322

Query:   423 ATTGTCATCATGTTCCCTGGGAGATGGATTGGGNTTGTC 479
             ||||||||||||||||||||||||||||||||| |||||
Sbjct:   323 AATGTCATCATGTTCCTGGGAGATGGATGGGTGTCTC 377
```

Figure 7
100X magnification
400X magnification
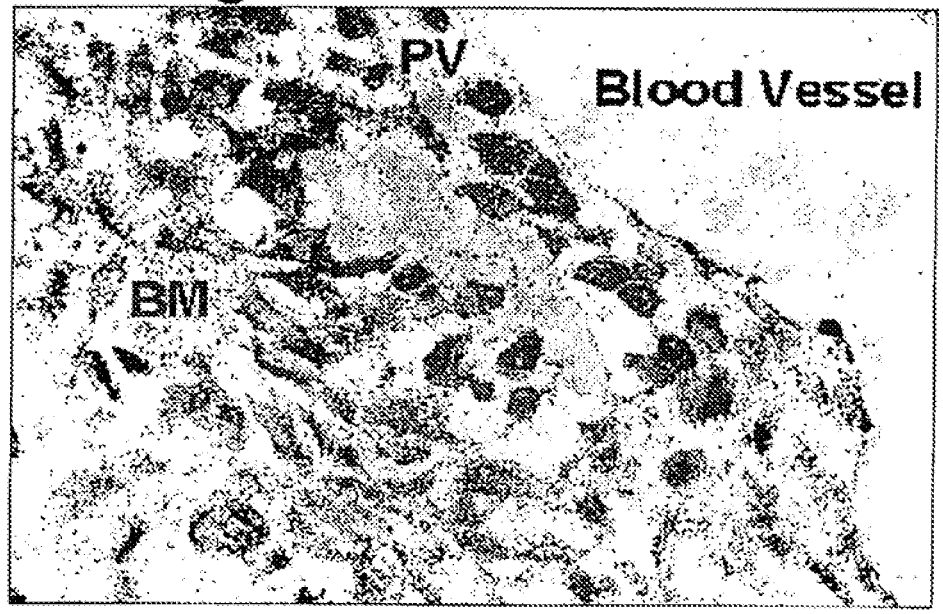

SEQUENCE LISTING

```
<160> NUMBER OF SEQ ID NOS: 3

<210> SEQ ID NO 1
<211> LENGTH: 524
<212> TYPE: PRT
<213> ORGANISM: Homo sapiens

<400> SEQUENCE: 1

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300
```

```
Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
            325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Pro Val Pro
            435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
            515                 520

<210> SEQ ID NO 2
<211> LENGTH: 524
<212> TYPE: PRT
<213> ORGANISM: Mus musculus

<400> SEQUENCE: 2

Met Ile Ser Pro Phe Leu Val Leu Ala Ile Gly Thr Cys Leu Thr Asn
1               5                   10                  15

Ser Phe Val Pro Glu Lys Glu Arg Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Val Ile Met Phe Leu Gly Asp Gly Met Gly Val
50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
130                 135                 140

Asn Glu Val Thr Ser Ile Leu Arg Trp Ala Lys Asp Ala Gly Lys Ser
```

|     |     |     |     |     | 145 |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Val Gly Ile Val Thr Thr Thr Arg Val Asn His Ala Thr Pro Ser Ala
                165                            170                    175

Ala Tyr Ala His Ser Ala Asp Arg Asp Trp Tyr Ser Asp Asn Glu Met
                180                            185                    190

Pro Pro Glu Ala Leu Ser Gln Gly Cys Lys Asp Ile Ala Tyr Gln Leu
            195                            200                    205

Met His Asn Ile Lys Asp Ile Asp Val Ile Met Gly Gly Gly Arg Lys
        210                            215                    220

Tyr Met Tyr Pro Lys Asn Arg Thr Asp Val Glu Tyr Glu Leu Asp Glu
225                    230                    235                    240

Lys Ala Arg Gly Thr Arg Leu Asp Gly Leu Asp Leu Ile Ser Ile Trp
                245                            250                    255

Lys Ser Phe Lys Pro Arg His Lys His Ser His Tyr Val Trp Asn Arg
            260                            265                    270

Thr Glu Leu Leu Ala Leu Asp Pro Ser Arg Val Asp Tyr Leu Leu Gly
        275                            280                    285

Leu Phe Glu Pro Gly Asp Met Gln Tyr Glu Leu Asn Arg Asn Asn Leu
        290                            295                    300

Thr Asp Pro Ser Leu Ser Glu Met Val Glu Val Ala Leu Arg Ile Leu
305                    310                    315                    320

Thr Lys Asn Leu Lys Gly Phe Phe Leu Leu Val Glu Gly Gly Arg Ile
                325                            330                    335

Asp His Gly His His Glu Gly Lys Ala Lys Gln Ala Leu His Glu Ala
            340                            345                    350

Val Glu Met Asp Gln Ala Ile Gly Lys Ala Gly Ala Met Thr Ser Gln
                355                            360                    365

Lys Asp Thr Leu Thr Val Val Thr Ala Asp His Ser His Val Phe Thr
        370                            375                    380

Phe Gly Gly Tyr Thr Pro Arg Gly Asn Ser Ile Phe Gly Leu Ala Pro
385                    390                    395                    400

Met Val Ser Asp Thr Asp Lys Lys Pro Phe Thr Ala Ile Leu Tyr Gly
                405                            410                    415

Asn Gly Pro Gly Tyr Lys Val Val Asp Gly Glu Arg Glu Asn Val Ser
            420                            425                    430

Met Val Asp Tyr Ala His Asn Asn Tyr Gln Ala Gln Ser Ala Val Pro
                435                            440                    445

Leu Arg His Glu Thr His Gly Gly Glu Asp Val Ala Val Phe Ala Lys
        450                            455                    460

Gly Pro Met Ala His Leu Leu His Gly Val His Glu Gln Asn Tyr Ile
465                    470                    475                    480

Pro His Val Met Ala Tyr Ala Ser Cys Ile Gly Ala Asn Leu Asp His
                485                            490                    495

Cys Ala Trp Ala Gly Ser Gly Ser Ala Pro Ser Pro Gly Ala Leu Leu
            500                            505                    510

Leu Pro Leu Ala Val Leu Ser Leu Pro Thr Leu Phe
        515                            520

<210> SEQ ID NO 3
<211> LENGTH: 524
<212> TYPE: PRT
<213> ORGANISM: Rattus norvegicus

<400> SEQUENCE: 3

-continued

```
Met Ile Leu Pro Phe Leu Val Leu Ala Ile Gly Pro Cys Leu Thr Asn
1               5                   10                  15
Ser Phe Val Pro Glu Lys Glu Lys Asp Pro Ser Tyr Trp Arg Gln Gln
            20                  25                  30
Ala Gln Glu Thr Leu Lys Asn Ala Leu Lys Leu Gln Lys Leu Asn Thr
        35                  40                  45
Asn Val Ala Lys Asn Ile Ile Met Phe Leu Gly Asp Gly Met Gly Val
50                  55                  60
Ser Thr Val Thr Ala Ala Arg Ile Leu Lys Gly Gln Leu His His Asn
65                  70                  75                  80
Thr Gly Glu Glu Thr Arg Leu Glu Met Asp Lys Phe Pro Phe Val Ala
            85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
            115                 120                 125
Gly Val Ser Ala Ala Thr Glu Arg Thr Arg Cys Asn Thr Thr Gln Gly
    130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
                180                 185                 190
Arg Pro Glu Ala Leu Ser Gln Gly Cys Lys Asp Ile Ala Tyr Gln Leu
            195                 200                 205
Met His Asn Ile Lys Asp Ile Asp Val Ile Met Gly Gly Gly Arg Lys
        210                 215                 220
Tyr Met Tyr Pro Lys Asn Arg Thr Asp Val Glu Tyr Glu Leu Asp Glu
225                 230                 235                 240
Lys Ala Arg Gly Thr Arg Leu Asp Gly Leu Asp Leu Ile Ser Ile Trp
                245                 250                 255
Lys Ser Phe Lys Pro Arg His Lys His Ser His Tyr Val Trp Asn Arg
                260                 265                 270
Thr Glu Leu Leu Ala Leu Asp Pro Ser Arg Val Asp Tyr Leu Leu Gly
            275                 280                 285
Leu Phe Glu Pro Gly Asp Met Gln Tyr Glu Leu Asn Arg Asn Asn Leu
            290                 295                 300
Thr Asp Pro Ser Leu Ser Glu Met Val Glu Val Ala Leu Arg Ile Leu
305                 310                 315                 320
Thr Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
                340                 345                 350
Val Glu Met Asp Glu Ala Ile Gly Lys Ala Gly Thr Met Thr Ser Gln
            355                 360                 365
Lys Asp Thr Leu Thr Val Val Thr Ala Asp His Ser His Val Phe Thr
            370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
                405                 410                 415
```

-continued

```
Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
        450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Ser Ser Ala Ser Ser Pro Ser Pro Gly Ala Leu Leu
            500                 505                 510

Leu Pro Leu Ala Leu Phe Pro Leu Arg Thr Leu Phe
        515                 520
```

ISOLATION OF ADULT MULTIPOTENTIAL CELLS BY TISSUE NON-SPECIFIC ALKALINE PHOSPHATASE

CROSS-REFERENCE TO RELATED APPLICATIONS

This application is a continuation of U.S. patent application Ser. No. 15/651,469 filed Jul. 17, 2017, which is continuation of U.S. patent application Ser. No. 15/167,934, filed May 27, 2016, now U.S. Pat. No. 9,783,617, issued Oct. 10, 2017, which is divisional of U.S. patent application Ser. No. 14/621,470, filed Feb. 13, 2015, which is a divisional of U.S. patent application Ser. No. 13/736,790, filed Jan. 8, 2013, which is a continuation of U.S. patent application Ser. No. 11/918,593, filed Sep. 28, 2008, now U.S. Pat. No. 8,367,405, issued Feb. 5, 2013, which is a § 371 national stage of PCT International Application No. PCT/AU2006/000494, filed Apr. 12, 2006, claiming the benefit of U.S. Provisional Application No. 60/670,250, filed Apr. 12, 2005, the contents of each of which are hereby incorporated by reference in their entirety into this application.

FIELD OF THE INVENTION

The present invention relates to the use of tissue non-specific alkaline phosphatase (TNAP) as a marker for identifying and/or isolating adult multipotential cells. The present invention also relates to cell populations enriched by methods of the present invention and therapeutic uses of these cells.

BACKGROUND OF THE INVENTION

Enrichment of Adult Multipotential Cells

Numerous studies support the concept that the non-haemopoietic cells of the bone marrow (BM), which include fibroblasts, adipocytes, choiadroblasts, smooth muscle cells, osteoblasts and other cellular elements of bone, are derived from a population of multipotential bone marrow mesenchymal precursor cells (MPC), residing somewhere in the bone marrow spaces and the surrounding connective tissue (Bianco et al., 2001; Gronthos and Simmons, 1996; Owen and Friedenstein, 1988; Prockop, 1997). These MPC are thought to give rise not only to more cells which are phenotypically and functionally identical (a process of self-renewal), but also differentiated, lineage-committed mesenchymal progeny. Due to the lack of well defined markers, little is known of the precise developmentally regulated changes in phenotype and patterns of gene expression, which occur during the differentiation and maturation of human MPC into lineage-committed progeny. Studies examining the process of osteogenesis have identified one such early marker, the transcription factor CBFA1, which enables the identification of MPC which have made a commitment to the osteogenic cell lineage (Ducy et al, 1997). However, markers such as CBFA1, can not be used to isolate and manipulate living cells within a heterogeneous cell population. This represents a major limitation, and is further compounded by a paucity of monoclonal antibodies (mAb) which are able to identify cell surface antigens which are peculiar to or restricted to the MPC compartment.

To date, the STRO-1 monoclonal antibody represents the only reagent which demonstrates immunoreactivity with all colony forming MPC (CFU-F: colony-forming units-fibroblasts) from aspirates of human marrow whilst lacking reactivity with haemopoietic stem cells (Dennis et al., 2002: GTonihos et al, 2003; Simmons and Torok-Storb, 1991).

Our studies have shown that ex vivo expanded human MPC quickly differentiate in the presence of serum, and begin expressing many of the markers associated with commitment to the osteogenic and other cell lineages (Gronthos et al., 2003). The mAb STRO-1 which identifies all MPC (CFU-F) in vivo, is down regulated following ex vivo culture of MPC. Importantly, a small proportion of cultured cells continue to express STRO-1 following ex vivo expansion and these cells are characteristic of undifferentiated MPC (Gronthos et al., 1999; Stewart et al., 1999).

Alkaline Phosphatases

Alkaline phosphatases (AP, EC 3.1.3,1) belong to a ubiquitous family of dimeric metalloenzymes which catalyse the hydrolysis of phosphomonoesters under alkaline conditions with release of inorganic phosphate (McComb et al., 1979). One can distinguish between four isoenzymes in humans: i) placenta-specific AP, ii) germ cell specific (placental) AP, iii) intestinal AP and iv) the tissue non-specific AP (TNAP) (Harris, 1990). The production of TNAP is strongest in the liver (LAP), kidney (KAP) and bones (BAP) (Moss, 1992) and is the most frequent AP isoform in serum (Mulivor, et al., 1985). The differences between LAP, KAP and BAP are due to different posttranslational O-glycosylation patterns (Miura; et al, 1994) which also results in different specific activities (Nosjean et al., 1997) although their amino acid sequences are essentially identical (Weiss et al., 1988). Furthermore Nosjean et al. (1997) have shown that the N-glycosylation of tns-AP is essential for its enzymatic activity. Consequently tissue non-specific AP is a mixture of different glycosylated APs.

The gene for human TNAP was cloned in 1986 (Weiss, et al, 1986), It codes for a protein consisting of 524 amino acids with a 17 amino acid long N-terminal signal sequence and a C-terminal GPI anchor sequence with which the protein is anchored in vivo to the outside of the plasma membrane (Hooper, 1997). Expression of a recombinant, biologically active TNAP enzyme in eukaryotic cells such as COS-1 (Fukushi, et al., 1998) and insect cells infected with baculovirus (Oda, et al., 1999) has been reported.

Although discovered more than seven decades ago, the exact function of the TNAP molecule in bone and bone marrow tissue is unclear. Several biological roles for TNAP in mammals have been proposed and include: hydrolysis of phosphate esters to supply the nonphosphate moiety; transferase action for the synthesis of phosphate esters; regulation of inorganic phosphate metabolism; maintenance of steady-state levels of phophoxyl-metabolites; acts as a phosphoprotein phosphatase (Wbyte, 1994). B/L/K-TNAP may also have a specific role in skeletal mineralization by hydrolyzing an inhibitor of calcification such as inorganic pyrophosphate, which in high concentrations can inhibit the growth of hydroxyapatite crystals (De Broe and Moss, 1992; Moss, 1992; Whyte, 1994). Alternatively, it has been suggested that TNAP could be a plasma membrane transporter for inorganic phosphate, an extracellular calcium ion binding protein that stimulates calcium phosphate precipitation and orients mineral deposition in osteoid, TNAP is known to be a marker of osteoblast differentiation. To our knowledge, however, there have been no previous reports of cell surface expression of TNAP by immature multipotential cells.

SUMMARY OF THE INVENTION

We have recently generated a novel mAb (designated STR.O-3) that identifies and isolates adult multipotential cells from unfractionated marrow and has the capacity to subdivide the STRO-1 population both in vivo and in vitro. We have determined that STRO-3 binds to tissue non-specific alkaline phosphatase (TNAP). Our results also show that STR.O-3 only reacts with a minor proportion of cells contained within adult bone marrow aspirates, and does not react with CD34 positive haemopoietic stem cells in human adult bone marrow aspixates. This indicates for the first time that TNAP is a marker that can be used for single reagent enrichment of adult multipotential cells from various tissue sources.

Accordingly, the present invention relates to the use of TNAP as a marker for the identification and/or enrichment of adult multipotential cells.

The present invention also provides a method of enriching for adult multipotential cells, the method comprising preparing a cell sample from a tissue source and enriching for cells that express the TNAP marker.

In one example the method of enriching for adult multipotential cells comprises
contacting the cell sample with a TNAP binding agent under conditions that allows binding of TNAP to the TNAP binding agent; and
separating cells bound to the TNAP binding agent.

The present invention also provides a method for identifying the presence of an adult multipotential cell in a cell sample, the method comprising identifying cells in the sample that express the TNAP marker.

In one example the method for identifying the presence of adult multipotential cells in a cell sample comprises
contacting the cell sample with a TNAP binding agent under conditions suitable for binding of TNAP to the TNAP binding agent; and
detecting the presence of the TNAP binding agent bound to cells in the sample, wherein the presence of adult multipotential cells is indicated by cells that bind to the TNAP binding agent It will be appreciated that in the context of the present invention, the cell sample may be derived from any tissue source suspected of containing adult multipotential cells. For example, the tissue source may be adipose tissue, teeth, dental pulp, skin, liver, kidney, heart, retina, brain, hair follicles, intestine, lung, spleen, lymph node, thymus, ovary, pancreas, bone, ligament, bone marrow, tendon or skeletal muscle. In a preferred embodiment, the tissue source is bone marrow.

The preferred source of cells is human, however, it is expected that the invention is also applicable to other animals, including agricultural animals such as cows, sheep, pigs and the like, domestic animals such as dogs and cats, laboratory animals such as mice, rats, hamsters and rabbits or animals that are be used for sport such as horses.

The method may also include the harvesting of a source of the multipotential cells before the first enrichment step. This may involve, for example, surgically removing tissue from a subject and separating the cells of the tissue to form a single cell suspension. This separation may be achieved by physical or enzymatic means. In one example of the invention this step involves harvesting bone marrow cells using known techniques.

The TNAP binding agent used in the methods of the present invention can be any polypeptide or compound identified, as having binding affinity to TNAP. For example, the TNAP binding agent may be an antibody or collagen, preferably collagen type I.

The TNAP binding agent can bind to any one or mote of the LAP, KAP or BAP isoforms of TNAP. In one preferred embodiment, however, the TNAP binding agent binds to BAP. In another preferred embodiment, the TNAP binding agent binds specifically to BAP.

By "binds specifically to BAP" we mean that the TNAP binding agent is capable of being bound to BAP in a selective fashion in the presence of excess quantities of other materials such as KAP and LAP, and tightly enough (i.e. with high enough affinity) that it provides a useful tool for selective enrichment of cells expressing BAP.

In a preferred embodiment, the TNAP binding agent is an anti-TNAP antibody (naturally occurring or recombinant, from any source). The anti-TNAP antibody can be a polyclonal or monoclonal antibody. In a preferred embodiment, the anti-TNAP antibody is monoclonal antibody.

Examples of suitable anti-TNAP monoclonal antibodies for use in the present invention include B4-78, 50 and B4-50 (Developmental Studies Hybridoma Bank, University of Iowa); ab17973 and abl7989 (Abeam Ltd, Cambridge, IJK); and the anti-TNAP mAbs referred to in Magnusson et al. (2002).

In a particularly preferred embodiment of the present invention, the anti-TNAP monoclonal antibody is a STRO-3 antibody produced by the hybridoma cell line deposited with ATCC on 19 Dec. 2005 under the provisions of the Budapest Treaty under deposit accession number PTA-7282, or a mAb that binds to the same epitope on TNAP as the STR.-3 antibody.

The method of enriching for adult multipotential cells according to the present invention may be based on the presence of the TNAP marker alone. In other words, the method of enrichment may involve a single reagent (i.e. a TNAP binding agent).

It will be understood, however, that the invention is not limited to the enrichment of cells by their expression of only TNAP, and in some circumstances it may be preferred to enrich for adult multipotential cells based on the expression of TNAP in combination two, three or more additional markers. Accordingly, the method of enriching for adult multipotential cells may also be based on the additional presence of one or more markers selected from the group consisting of, LFA-3, THY-1, VCAM-1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CDlO, CD13, SCF, PDGF-R, EGF-R, IGF1-R, NGF-R, FGF-R, Leptin-R, (STRO-2-Leptin-R), RANKL, STRO-1 (preferably STRO-1$^{bri}$) and CD 146 or any combination of these markers.

For example, the method may include the step of making a first partially enriched pool of cells by enriching fox the expression of a first adult multipotential cell specific marker, followed by a step of enriching for expression of TNAP from the partially enriched pool of cells. In another example, the method may include an initial enrichment step based on selection of cells expressing TNAP, followed by a step which involves enriching for a different adult multipotential cell marker. In yet another example, the method involves simultaneously selecting for cells that express TNAP and one or more additional adult multipotential cell specific markers.

It will be understood that recognition of cells carrying TNAP that forms the basis of the separation can be effected by a number of different methods, however, all of these methods rely at some point upon binding of cells to the TNAP binding agent followed by separation of those cells that exhibit binding, being either high level binding, or low level binding or no binding. The most convenient binding agents are antibodies or antibody based molecules, preferably being monoclonal antibodies or based on monoclonal antibodies because of the specificity of these latter agents.

The TNAP binding agents may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to $MACS_5$ Dynal magnetic bead selection and FACS—

In one example of the invention, the TNAP binding agent is labelled. In another example, the separatum of cells bound to the TNAP binding agent is carried out by a mechanical cell sorter.

In a further example of the invention the TNAP binding agent is coupled to a fluorescent labelling compound. In this case the separation of cells bound b the TNAP binding agent is preferably carried out using a fluorescence-activated cell sorter (FACS).

In a further example of the invention, the TNAP binding agent is linked to a solid particle. Preferably, the solid particle is a magnetic particle. In this embodiment of the invention, the separation of cells bound to the TNAP binding agent is preferably carried out by separating the particulate! phase from the liquid phase. In a further preferred embodiment of the invention, prior to the separation, step the cell sample is contacted with an antibody directed against the TNAP binding agent linked to a solid particle, and wherein the separation of cells bound to the TNAP binding agent is earned out by separating the particulate phase from the liquid phase.

In a further example of the invention the cells of the cell sample are adherent cells cultivated on a solid-support, and removal of unbound TNAP binding agents is carried out by rinsing.

A further example of the invention, the cells of the cell sample are cultivated in suspension, and removal of unbound TNAP binding agents is carried out by centrifuging the cell sample and separating off the resulting supernatant In a further example, the cell sample is subjected to a further cell sorting procedure to enrich or diminish the cell population in ceils expressing at least one further muMpotential cell marker. The multipotential cell marker may one or more markers selected from the group consisting of LFA-3, THY-1, VCAM-1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CDlO, CD13, SCF PDGF-R, EGF-R, IGF1-R, NGF-R, FGF-R, Leptin-R, (STRO-2=Leptin-R), RANKL, STRO-1 (preferably STRO-$1^{bri}$) and CD146 or any combination of these markers.

The present invention also provides an enriched population of adult multipotential cells as obtained by a method according to the present invention.

The present invention also provides an enriched population of TNAP+ adult multipotential cells.

In a preferred embodiment of the present invention, at least 1%, 2%, 3%, 4%, 5%, 10%, 15%, 20%, 30%, 40%, 50%, 60%, 70%, 80%, 90% or 95% of the total enriched cell population are adult multipotential cells that have the phenotype TNAP+.

In an embodiment, culturing the enriched population of the invention results in a higher proportion of cells that are STRO+ when compared to cells selected using STRO-1 as a marker and cultured under the same conditions. Preferably, such culturing is for about 4 or about 6 passages. Preferably, the cells were obtained from the bone marrow.

In another embodiment, the enriched population of the invention comprises about 79% to about 99%, more preferably about 84% to about 94%, and even more preferably about S9%, cells which are CD45+.

Preferably, the enriched population of adult multipotential cells were obtained by a method according to the present invention.

The present invention also provides an expanded cell population obtained by culturing an enriched population of adult multipotential cells according to the invention.

In one embodiment, the enriched cell population of the invention, or an expanded cell population of the invention, comprises at least some cells which are genetically modified.

The present invention also provides a method of generating a tissue specific committed cell population, the method comprising
culturing a population of adult multipotential cells of the present invention in the presence of one or more stimulatory factors, and
subjecting said cultured population to conditions biasing differentiation of the adult multipotential cells to a specific tissue type.

In one embodiment of this method of the invention the tissue type is selected from the group consisting of cardiac muscle, vascular tissue, bone tissue, cartilage tissue, fat tissue, neural tissue, smooth muscle and endothelial tissue.

The invention will also be understood to encompass a composition comprising enriched adult multipotential cells of the present invention and/or an expanded cell population of the invention.

In a preferred embodiment, the composition further comprises a stimulatory factor. Such a composition is likely to be beneficial therapeutically and thus will be prepared in a pharmaceutically acceptable form.

The level of the stimulatory &ctor(s) present in the composition may be determined empirically but in most cases is likely to be in the order of nanograms or tens of nanograms per millilitre.

The stimulatory factor used in a method of the invention, and/or present h a composition of the invention, can be any suitable factor capable of promoting cell division and/or differentiation. Such factors are well known in the art and include, but are not limited to 1α,25-dihydroxyvitamin $D_3$ (1,25D), platelet derived growth factor (PDGF), tumor necrosis factor α(TNF-α), interleukin-1β(TL-1β) and stromal derived factor 1α(SDF-1α).

In another embodiment the composition further comprises a factor to bias differentiation of the adult multipotential cells of the present invention to one specific tissue type. Preferably, the tissue type is selected from the group consisting of cardiac muscle, vascular tissue, bone tissue, cartilage tissue, iai tissue, neural tissue, smooth muscle and endothelial tissue Conditions that bias differentiation of the adult multipotential cells of the present invention to bone precursor cells or bone may involve, for example, culturing in αMEM supplemented with 10% FCS, 100 µM L-ascorbate-2-phosphate, dexamethasone $10^{-7}$M and 3 mM inorganic phosphate. These conditions have been shown to induce human bone marrow stromal cells to develop a mineralized bone matrix in vitro (Gronthos et al, 1994).

Suitable conditions for differentiating the adult multipotential cells of the present invention into osteoblasts may involve cultivating the cells in the presence of type I collagen, fibrinogen, fibrin, polyglycolic acid, polylactic acid, osteocalcin, or osteonectin. In one particular example, the cells are cultivated in the presence of type I collagen, fibrinogen, and fibrin. In an alternative example, the cells are cultivated in the presence of type I collagen, fibrinogen, fibrin, osteocalcin, and osteonectin. In the context of this method, type I collagen, fibrinogen, fibrin, polyglycolic acid, polylactic acid, osteocalcin, or osteonectin may be used alone or in the presence of a growth factor. It will be understood that any combination of the compounds listed above in this paragraph is contemplated by the present invention.

In a further embodiment, a composition of the invention further comprises a fibrin glue.

The present invention also provides a method for generating or repairing tissue in a subjects the method comprising administering to the subject an enriched or expanded cell population of the present invention.

The present invention also provides a method for generating or repairing tissue in a subject, the method comprising administering to the subject a composition of the present invention.

The enriched or expanded cell population of multipotential cells obtained according to the present invention may be used, for example, in the formation and repair of bones, and as such a combination of multipotential cells as well as a suitable support may be introduced into a site requiring bone formation. Thus, for example, skeletal defects caused by bone injury or the removal of sections of bone infected with tumour may be repaired by implanting cultured or expanded adult multipotential cells contained in calcium phosphate ceramic vehicles into the defect site. For appropriate methods and techniques see Caplan et aL in U.S. Pat. Nos. 5,226,914 and 5,837,539, both of which use cruder preparations of stem cells when compared to the present invention.

In addition, the enriched cell population or composition may be used to assist in anchoring prosthetic devices. Thus, the surface of a prosthetic device such as those used in hip, knee and shoulder replacement, may be coated with the enriched multipotential cells prior to implantation. The multipotential cells may then differentiate into osteogenic cells to thereby speed up the process of bony ingrowth and incorporation of the prosthetic device (see Caplan. et al. in U.S. Pat. Nos. 5,226,914 and 5,837,539).

The enriched cell population or composition might also be used in gene therapy so that, for example, an enriched population may have exogenous nucleic acid transformed into it and then such a population may be introduced into the body of the patient to treat a disease or condition. Alternatively it might be used for the release of therapeutics. For appropriate techniques we refer to U.S. Pat. No. 5,591,625 by Gerson et al. which uses cruder preparations of stem cells when compared to the present invention.

Alternatively the enriched population or composition may be used to augment bone marrow transplantation, wherein the composition containing enriched adult multipotential cells can be injected into a patient undergoing marrow transplantation prior to the introduction of the whole marrow. In this way the rate of haemopoiesis may be increased, particularly following radiation or chemotherapy. The composition might also encompass a mixture of multipotential cells and haemopoietic cells which may be useful in radiotherapy or chemotherapy.

Also provided is the use of an enriched or expanded cell population of the present invention for the manufacture of a medicament for generating or repairing tissue in a subject Also provides is the use of a composition of the present invention for the manufacture of a medicament for generating or repairing tissue in a subject.

The present invention also provides an isolated cell which has been obtained by a method of the invention, or a progeny cell thereof, wherein the cell is genetically modified.

In a preferred embodiment, the cell is genetically modified to express a heterologous protein. The heterologous protein may be any protein of interest. For example, the heterologous protein may be a stimulatory factor such as 1α1,25-dihydroxyvitamin $D_3$ (1,25D), platelet derived growth factor (PDGF), tumor necrosis factor α(TNF-α), interleukin-1β(IL-1β) and stromal derived factor Ia (SDF-1α).

In another example, the heterologous protein is a bioactive factor which accelerates differentiation of the adult multipotential cell to specific tissue types. The bioactive factor may be, for example, a synthetic glucocorticoid, such as dexamethasone, or a bone morphogenic protein, such as BMP-2, BMP-3, BMP-4, BMP-6 or BMP-7.

The present invention also provides a [STRO-3] hybridoma cell line deposited with ATCC on 19 Dec. 2005 under fixe provisions of the Budapest Treaty under deposit accession number PTA-7282.

The present invention also provides a STR.O-3 antibody produced by the hybridoma cell line deposited with ATCC on 19 Dec. 2005 under the provisions of the Budapest Treaty under deposit accession number PTA-7282.

The present invention also provides an isolated antibody which binds to the same epitope on multipotential cells as the STRO-3 antibody produced by the hybridoma cell line deposited with ATCC on 19 Dec. 2005 under the provisions of the Budapest Treaty under deposit accession number PTA-7282.

The present invention also provides a composition comprising an antibody of the invention. Preferably, the composition further comprises one or more suitable carriers.

Also provided is a kit comprising an enriched cell population of the invention, an expanded cell population of the invention, a composition of the invention, an isolated cell of the invention, a hybridoma of the invention and/or an antibody of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The various features and embodiments of the present invention, referred to in individual sections above apply, as appropriate, to other sections, mutatis mutandis.

Consequently features specified in one section may be combined with features specified in other sections, as appropriate.

BRIEF DESCRIPTION OF THE FIGURES

FIG. 3. FASTA Alignment Analysis of STRO-3 antigen derived PCR Products Following partial sequence analysis, the resultant nucleotide sequence was compared with sequences submitted to the combined Geribank/EMBL database via standard "FASTA alignment analysis", and revealed 100% homology with the BLK isoform of ALP complementary DNA sequence (Genbank accession #H37944).

RT-PCR was employed to identify the alkaline phosphatase isoform encoded by the cDNA using total RNA isolated from BAF-3 cells expressing the STRO-3 cell surface Ag as described in the methods. The PCR primers used identified sequences specific to either the (L) liver (216 bp) or (B) bone (215 bp) alkaline phosphatase isoforms as previously described by Sato and colleagues (1994) (Sato et al., 1994). Following PCR amplification the products were run on a 1.5% agarose gel and stained with ethidium bromide. The results indicated that the STRO-3 antigen expressing BAF-3 cells only expressed transcripts corresponding to the bone-specific (B) alkaline phosphatase isoform.

FIG. 7. The Expression of STRO-3 Antigen in Human Bone Tissue The immunoreactivity of STRO-3 mAb was also assessed in sections of developing bone marrow using immunohistochemistry as described in the methods. Five micron sections of paraffin-embedded, 55 day old human limb, was stained with STRO-3 mAb, as described in the methods. While expression of the STRO-3 antigen (TNAP) was evident in the mesenchymal cells of the bone marrow spaces (BM), perivascular regions (PV) and at the interface of the growth plate region, no staining was observed in the periosteum (P) or cartilage (C).

Figure 8:
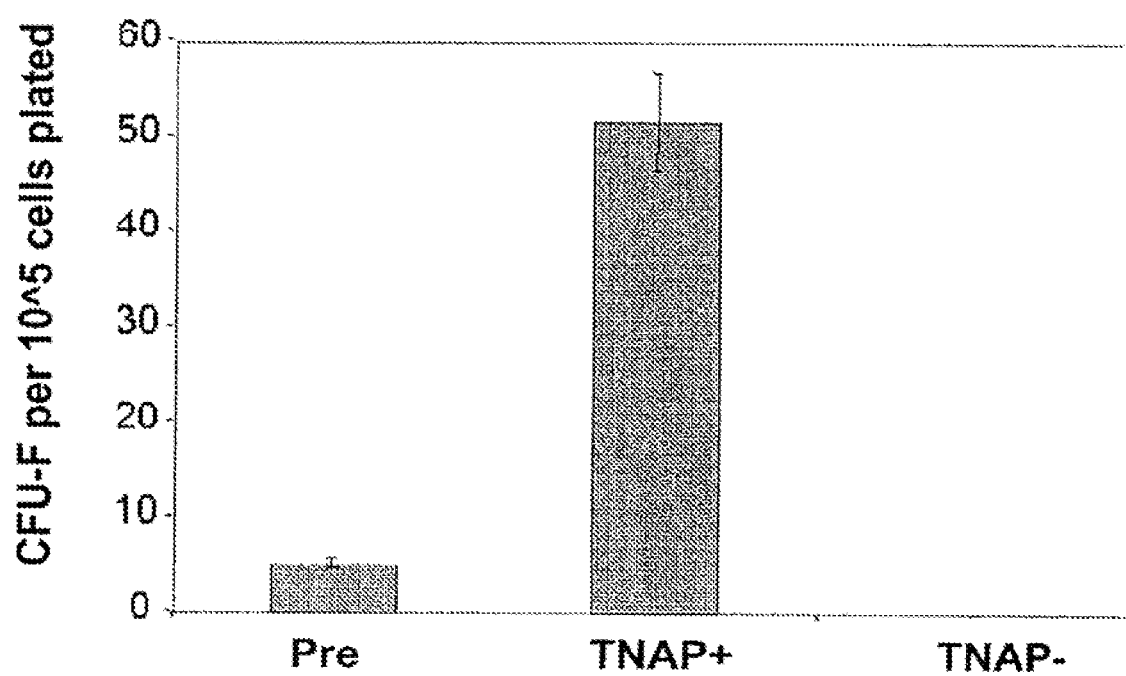

FIG. 8. Clonogenic cells are Exclusively Restricted to the STRO-3 mAb Positive Fraction of Human BM A single cell suspensions of unfractionated BM (Pre) and MACS selected TNAP positive (TNAP+) and TNAP negative (TNAP-) human BM were plated into regular growth medium (Gronthos et al., 2003) to assess the incidence of adherent colony-forming cells in each cell fraction. Following 12 days of culture, colonies (aggregates of 50 cells or more) were stained and scored as described in Methods. The bar graph depicts the number of elenaogenic colonies per $10^5$ cells plated for each cell fraction averaged from two separate experiments. Our data demonstrate that CFU-F are exclusively restricted to the TNAP positive fraction of BM.

Figure 9:
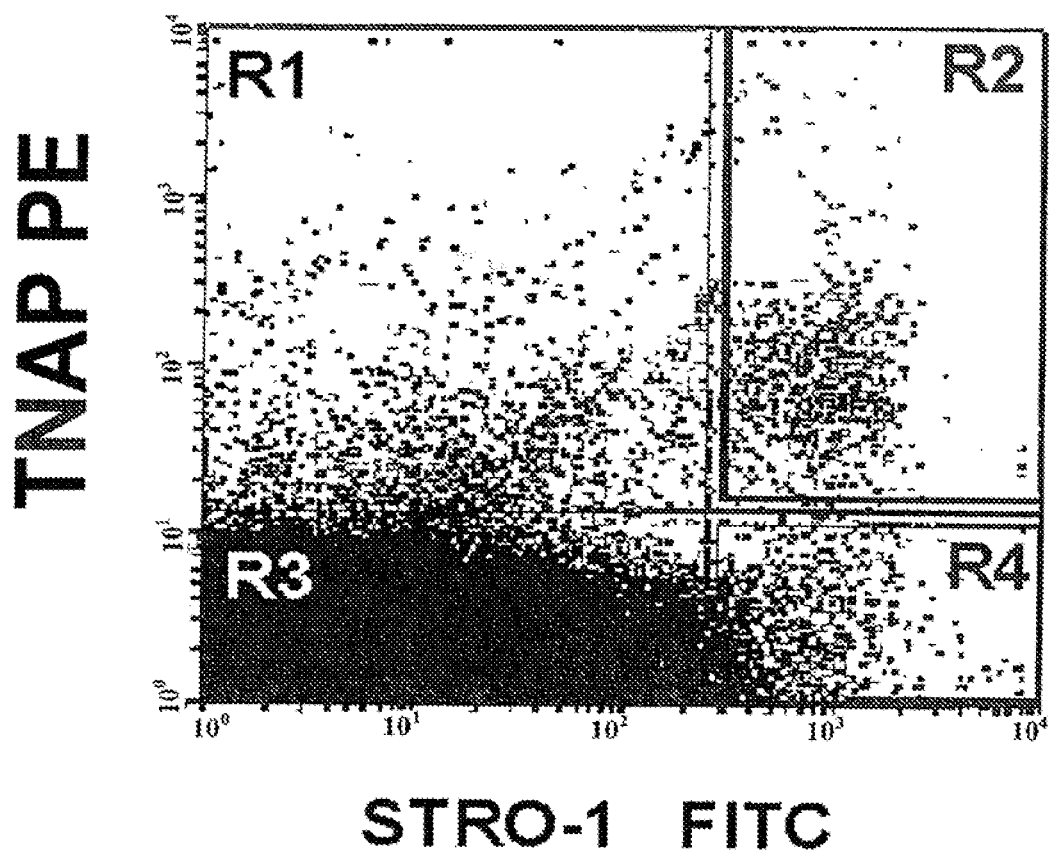

FIG. 9. Co-expression of TNTAP and the Mesenchymal Precursor Cell Marker, STRO-1 by Adult Human BMMNC Dual-color immunofluorescence and flow cytometry was performed by incubation, of STRO-1 MACS-selected BMMNC and indirectly labelled with a goat anti-murine IgM antibody coupled to FITC (x axis), and STRO-3 mAb (murine IgG1) indirectly labelled with a goat anti-murine IgG coupled to PE (y axis). The dot plot histogram represents $5 \times 10^4$ events collected as list mode data. The vertical and horizontal lines were set to the reactivity levels of <1.0% mean fluorescence obtained with the isotype-matched control antibodies, 1B5 (TgG) and 1A6.12 (IgM) treated under the same conditions. The results demonstrate that a minor population, of STRO-1 bright cells co-expressed TNAP (upper right quadrant) while the remaining STRO-1+ cells failed to react with the STRO-3 mAb. Cells isolated by FACS from all four quadrants were subsequently assayed for the incidence of CFU-F (Table 2).

Figure 10:
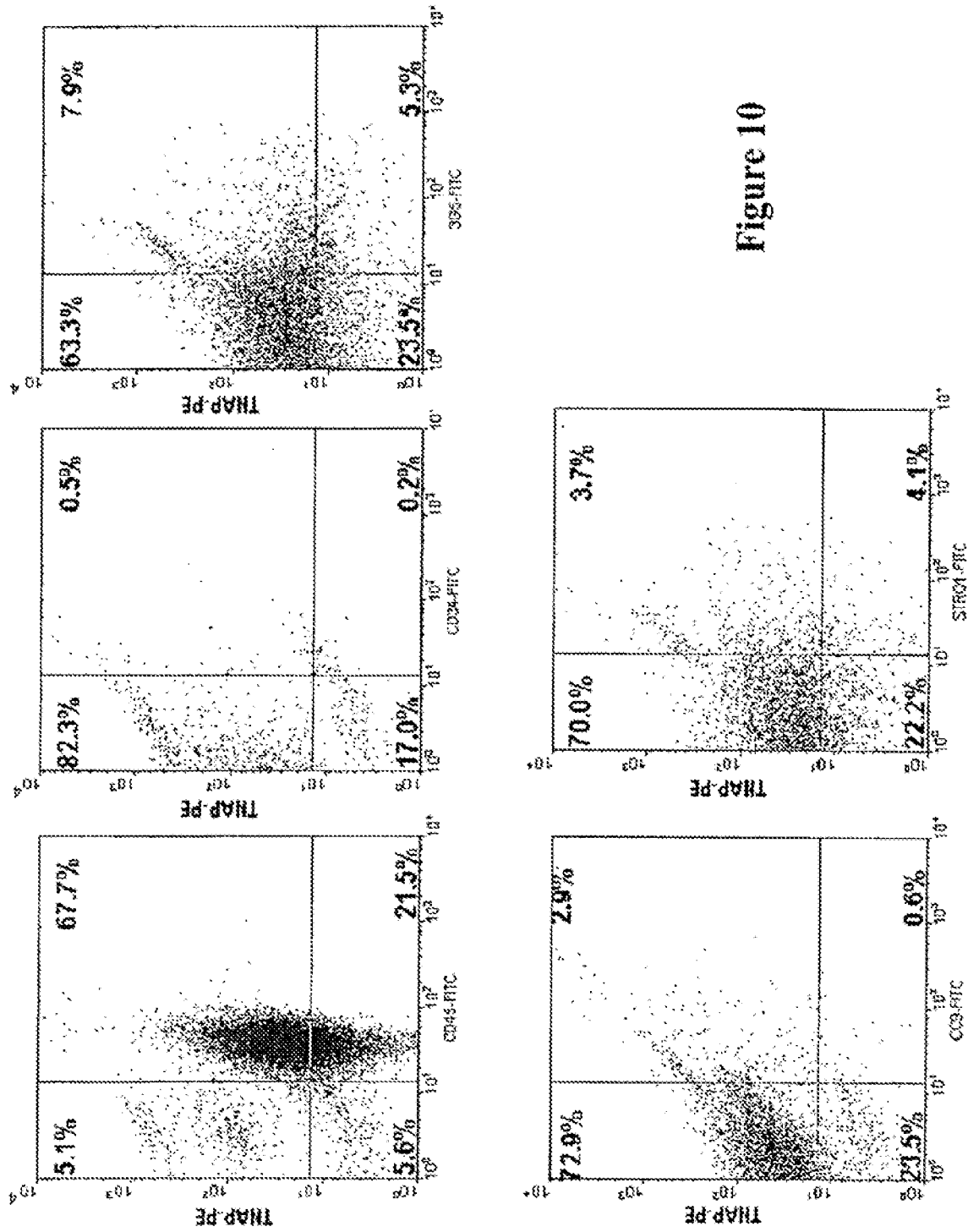

FIG. 10. Compression of CD45, CD34, 30%, CC9 and STRO-1 with TNAP by STR.0-3 mAb enriched cells FIG. 11. STRO-3 mAb selected cells maintain high levels of STRO-1 expression following multiple passages FIG. 12. STRO-1 expression in bone marrow derived cells selected using an antibody that binds thereto FIG. 13. Early (P2) and late (P5) passage phenotypic characteristics of STRO-3 mAb selected, culture expanded muMpotential cells STRO-3 selected adult multipotential cells (P1) are a population with a surface phenotype characterised by high levels of CC9, STRO-1 and STRO-3 antigen expression. Following 5 passages in culture the cell population (P5) demonstrates significant retention of STRO-1 expression.

Figure 14:
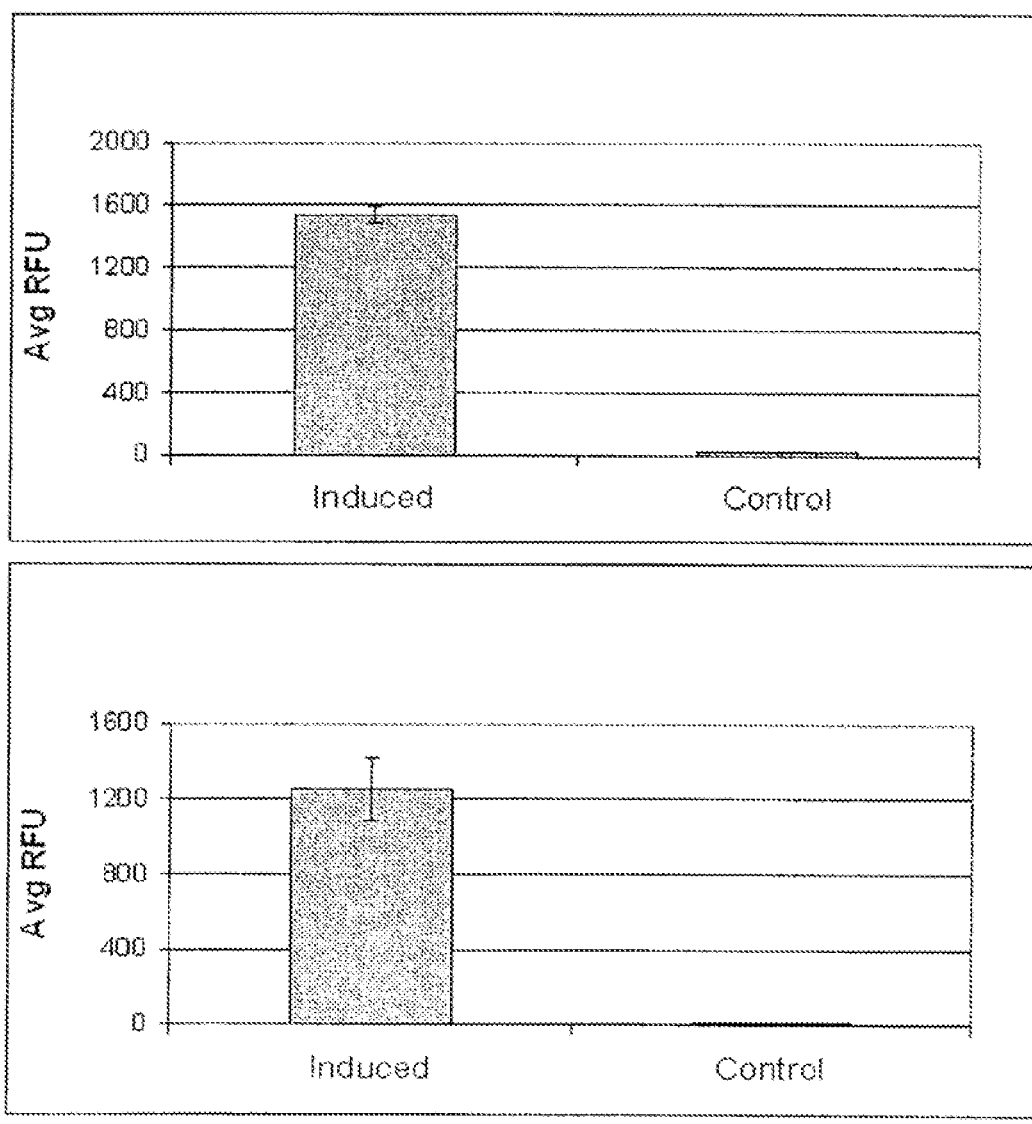

FIG. 14. Differentiation of STRO-3 mAb selected cells into adipocytes

Two lots of STRO-$3_{mAB}$Ab selected cells, 2242A and 2070C, were assayed for differentiative capacity. The graphs depict the average relative fluorescence units (Avg RFU) for cells induced with Adipogenic Induction Medium versus control uninduced cells.

Figure 15:
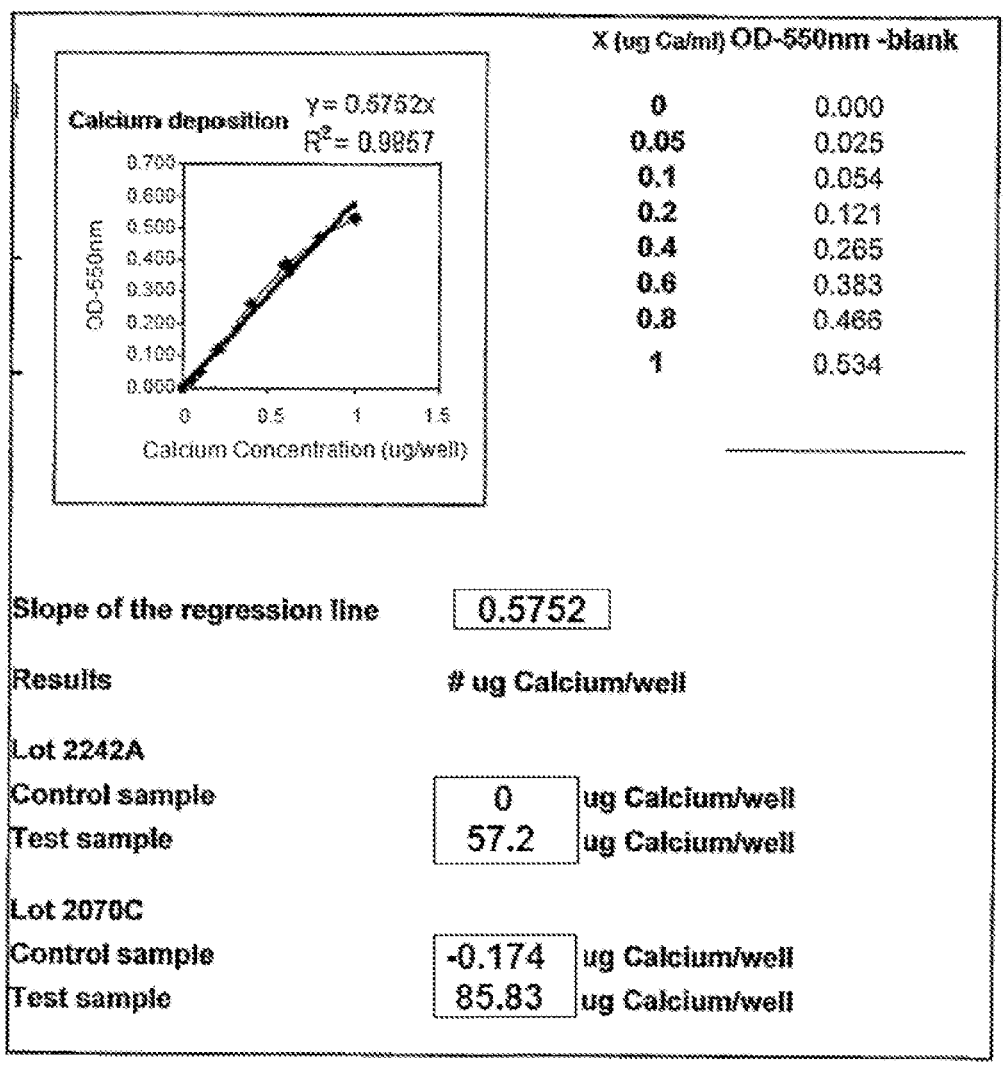

FIG. 15. Differentiation of STRO-3 mAb selected cells into osteocytes A standard curve was generated by taking the OD 550nr α of samples having known calcium concentrations. Two lots of STRO-$3_{mAb}$Ab selected cells, 2242A and 2070C, were induced with Osteogenesis Induction Medium. Cell extracts of induced and uninduced cells were prepared and measured at OD 550 nm.

Figure 16:
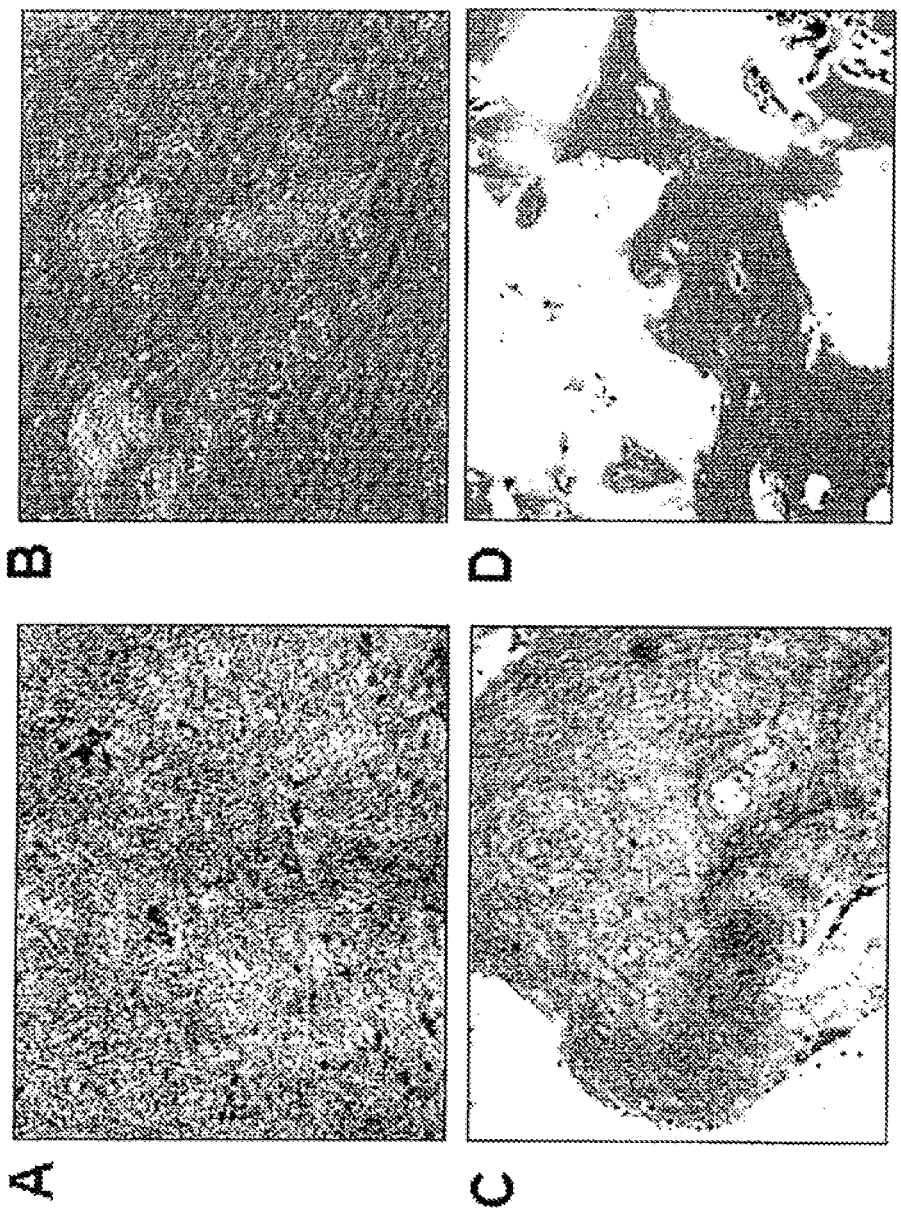

FIG. 16. Differentiation of STRO-3 mAb selected cells into functional osteoblasts A—STRO-3 mAb selected adult multipotential cells were cultured for three weeks in COMEM supplemented with 10% FCS, 100 µM L-ascorbate-2-phosphate, dexamethasone 10-7 M and 3 mM inorganic phosphate and stained for mineral deposits with Alizarin Red. B—Oil Red O stained cells following culture of STRO-3 mAb selected adult multipotential cells in the presence of 0.5 μM methylisobutylmethylxanthine, 0.5 μM hydrocortisone, and 60 μM indomethacin. C—Cell cultures treated with 10 ng/ml TGF-p3 and stained with Alcian Blue to identify proteoglycan synthesis. D—Histological examination of culture expanded STRO-3 mAb selected adult multipotential cells following implantation.

Figure 17:
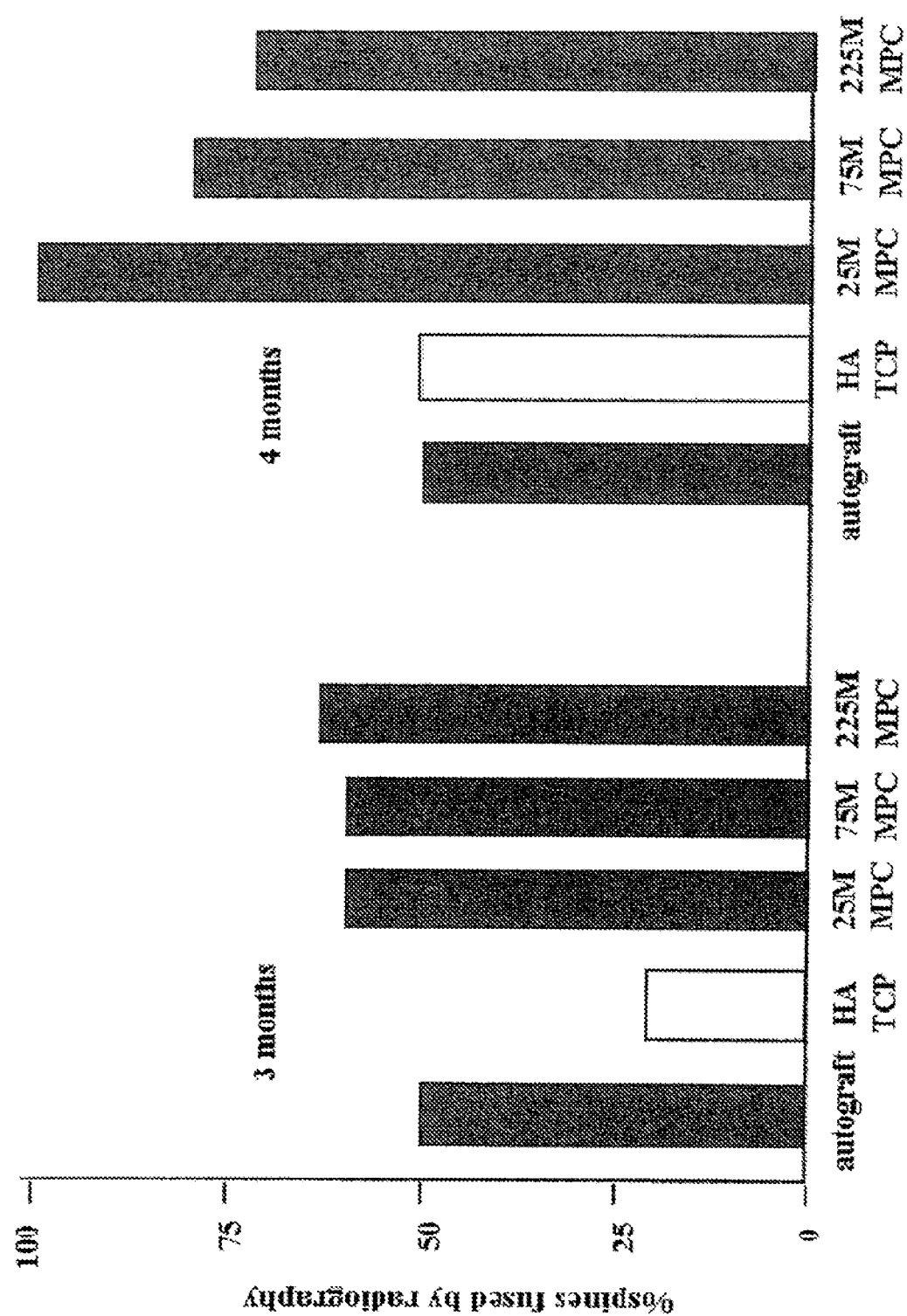

FIG. 17. Rate of spinal fusion following administration of culture expanded STRO-3 mAb selected cells FIG. 18. Robust spinal fusion in culture expanded STRO-3 mAb selected cells treated sheep FIG. 19. STRO-3 mAb selected culture expanded allogeneic adult multipotential cells in an ovine transpedicular screw fixation model FIG. 20. Dose-dependent bone growth by allogeneic culture expanded STRO-3 mAb selected cells in critical-sized sheep segmental tibial defect FIG. 21. Greater rate of union in culture expanded STRO-3 mAb selected cells treated groups with critical sized segmental tibial defect FIG. 22. Culture expanded STRO-3 mAb selected cells significantly improve cardiac function 2 weeks following rat myocardial infarction FIG. 23. Effects of allogenic sheep culture expanded STRO-3 selected cells (passage 5) directly injected into sheep heats immediately after acute ligation of both diagonal and coronary arteries A—% reduction in ejection fraction, B—% change in diastolic volume, and C—% change in systolic volume of sheep.

Figure 24:
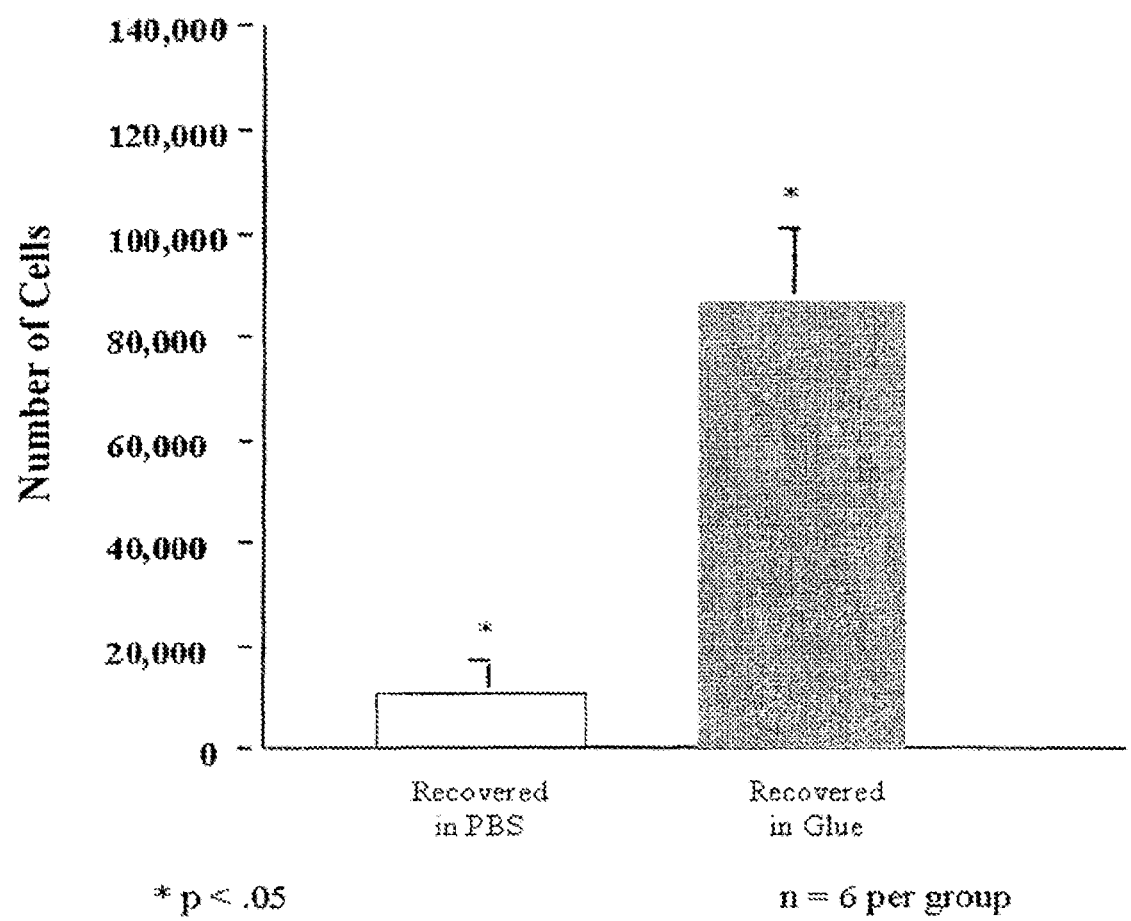

FIG. 24. Increased cell survival when delivered in fibrin glue compared to saline solution

DETAILED DESCRIPTION OF THE PREFERRED EMBODIMENTS

Micro-Organism Deposit Details

The hybridoma which produces the monoclonal antibody designated STRO-3 was deposited on 19 Dec. 2005 with American Type Culture Collection (ATCC) under accession number PTA-7282.

This deposit was made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent patent The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

General Techniques

Unless specifically defined otherwise, all technical and scientific terms used herein shall be taken t have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature ia sources such as, J. Perbal, A Practical Guide to Molecular Cloning, John. Wiley and Sons (1984), J. Sambrookk et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub, Associates and Wiley-Interscience (1988, including all updates until present), Ed Harlow and David Lane (editors) Antibodies: A Laboratory Manual, Cold Spring Harbour Laboratory, (1988); and J. E. Coligan et al. (editors) Current Protocols in Immunology, John Wiley & Sons (including all updates until present).

Adult Multipotential Cells

By "adult multipotential cells" we mean cells derived from adult tissue which are capable of giving rise to any of several mature cell types. As used herein, this phrase encompasses adult stem cells and progenitor cells, such as mesenchymal precursor cells (MPC) and multipotential progeny of these cells.

Mesenchymal precursor cells (MPCs) are cells found in bone marrow, blood, dermis, and periosteum; and are capable of differentiating into specific types of mesenchymal or connective tissues including adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. Mesenchymal precursor cells are defined as cells which are not terminally differentiated; which can divide without limit; and divide to yield daughter cells that ate either stem cells or are progenitor cells which in time will irreversibly differentiate to yield a phenotypic cell. MPCs are non-hematopoietic progenitor cells that are capable of forming large number of multipotential cells.

The terms 'enriched', 'enrichment' or variations thereof are used herein to describe a population of cells in which the proportion of one particular cell type or the proportion of a number of particular cell types is increased when compared with the untreated population.

In a preferred embodiment of the present invention, at least 1%, 2%, 3%, 4%, 5%, 10%, 15%, 20%, 30%, 40%, 50%, 60%, 70%, 80%, 90% or 95% of the total enriched cell population are adult multipotential cells that have the phenotype TNAP+.

In a particularly preferred embodiment, TNAP+ cells of the invention are able to bind the STRO-3 antibody produced by the hybridoma cell line deposited with ATCC on 19 Dec. 2005 under the provisions of the Budapest Treaty under deposit accession number PTA-7282.

In one embodiment, the enriched population of the invention comprises about 79% to about 99%, more preferably about 84% to about 94%, and even more preferably about 89.2%, cells which are CD45+.

In another embodiment, the enriched population of the invention comprises less than about 2%, more preferably less than about 1%, cells that are CD34+. In another embodiment, the enriched population comprises no cells that are CD34+.

In another embodiment, the enriched population of the invention comprises less than about 6%, more preferably less than about 3.5%, cells that are CC9+.

In a further embodiment, the enriched population of the invention comprises about 23% to about 3%, more preferably about 8% to about 18%, and even more preferably about 13.2%, cells which are 3G5+.

In yet a further embodiment, the enriched population of the invention comprises about 12% to about 3%, more preferably about 10% to about 6%, and even more preferably about 7.8%, cells which are STRO-1+.

In a further embodiment, an enriched cell population of the invention has not been cultured in vitro.

Furthermore, in a preferred embodiment, the enriched cell population of the invention is capable of giving rise to clonogenic CFU-F.

In an embodiment, culturing the enriched population of the invention results in a higher proportion of cells that are STR.O+ when compared to cells selected using STRO-1 as a marker and cultured under the same conditions. Preferably, such culturing is for about 4 or about 6 passages. Preferably, the cells were obtained from the bone marrow.

In a further embodiment, culturing the enriched population of the invention results in an increase in the number of progeny cells that are STRO+ when compared to the starting cell population, for example, after 2, 4 or 6 passages. In comparison, culturing STRO-1 enriched cells results in a decreased number of progeny cells that are STRO+ when compared to the starting (STRO-1 selected) cell population, for example, after 4 or 6 passages.

In another embodiment, the enriched cell population is homogenous for TNAP+ cells, The present invention also relates to progeny cells (also referred to herein as expanded cells) which are produced from the in vitro culture of adult multipotential cells of the invention. Expanded cells of the invention may a have a wide: variety of phenotypes depending on the culture conditions (including the number and/or type of stimulatory factors in the culture medium), the number of passages and the like.

In one embodiment, such expanded cells (at least after 5 passages) can be TNAP–, CC9+, HLA class I–, HLA class IF, CD14", CD 19–, CD3", CD 11a-c–, CD31", CD86" and/or CD80–. However, ft is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9–). In one preferred embodiment, expanded cells of the invention, still have the capacity to differentiate into different cell types.

In one embodiment, an expended cell population of the invention comprises cells wherein at least 25%, more preferably at least 50%, of the cells are CC9+.

In another embodiment, an expended cell population of the invention comprises cells wherein at least 40%, more preferably at least 45%, of the cells are STRO-1+.

In, a further embodiment, culturing the enriched population of the invention results in adult multipotential cells that may also express markers selected from the group consisting of LFA-3, THY-1, VCAM-1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CD10, CD3, SCF, PDGF-R, EGF-R, IGF1-R, NGF-R, FGF-R Leptin-R, (STRO-2=Leptin-R), RANKL, STRO-1$^{bright}$ and CD146 or any combination of these markers.

It is preferred that a significant proportion of the adult multipotential cells are capable of differentiation into at least two committed cell types. Non-limiting examples of the lineages to which the adult multipotential cells may be committed include bone precursor cells; hepatocyte progenitors, which are pluripotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentfrvproducing cells and chondrocytes, and precursor cells of flie following: retinal pigment epithelial cells, fibroblasts, skin cells such as kerathiocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells. In a preferred embodiment, the adult multipotential cells are at least capable of being cultured, in vivo or in vitro, to produce adipocytes, osteocytes and/or chondrocytes.

In another embodiment, "adult multipotential cells" of the invention are not capable of giving rise, upon culturing, to hematopoietic cells.

The term "adult" is used in its broadest sense to include a postnatal subject. In a preferred embodiment, the term "adult" refers to a subject that is postpubertal. The term, "adult" as used herein can also include cord blood taken from a female. The term "adult" does not include cells obtained from an embryo and/fetus. Thus, the "adult multipotential cells" of the invention may also be considered as "non-embryonic multipotential cells".

When we refer to a cell as being "positive" for a given marker it may be either a low (Io or dim) or a high (bright bri) expresser of that marker depending on the degree to Which the marker is present on the cell surface, where the terms relate to intensity of fluorescence or other colour used in the colour sorting process of the cells: The distinction of lo (or dim or dull) and bri will be understood in the context of the marker used on a particular cell population being jsørted. When we refer herein to a cell as being "negative" for a given marker, it does not mean that the marker is not expressed at all by that cell. It means that the marker is expressed at a relatively very low level by that cell, and that it generates a very low signal when detectably labelled.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance-STRO-1$^{bri}$ cells produce a greater fluorescent signal, when labelled with a FITC-conjugated STRO-1 antibody as determined by FACS analysis, than non-bright cells (STRO-1$^{dull/dim}$). Preferably, "bright" cells constitute at least about 0.1% of the most brightly labelled bone marrow mononuclear cells contained in the starting sample, In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a preferred embodiment, STRO-1$^{bright}$ cells have 2 log magnitude higher expression of STRO-1 surface expression. This is calculated relative to "background", namely cells that are STRO-F. By comparison, STRO-1$^{dim}$ and/or STRO-1$^{intermediate}$ cells have less than 2 log magnitude higher expression of STRO-1 surface expression, typically about 1 log or less than "background".

Tissue Non-Specific Alkaline Phosphatase (TNAP)

When used herein the term "TNAP" is intended to encompass all isoforms of the protein. For example, the term encompasses the liver isoform (LAP), the bone isoform (BAP) and the kidney isoform (KAP). In a preferred embodiment, the TNAP is BAP. La a particularly preferred embodiment. TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Ia the context of the present invention, the TNAPP is preferably human TNAP. For example, the TNAP may be human TNAP comprising the amino acid sequence shown in SEQIDNO:1.

However, it will be understood that the term "TNAP" is not limited to the human sequence but also includes homologous sequences obtained from any source, for example homologues, particularly orthologues (i.e. homologues obtained from species other than humans), allelic variants, as well as fragments and synthetic peptides or derivatives thereof as discussed below.

A number of $T_{TNAP}$ orthologues are already known and include mouse TNAP (SEQ ID NO:2) and rat TNAP (SEQ ID NO:3).

In a preferred embodiment of the present invention, a homologous sequence is an amino acid sequence which is at least 70, 80 or 90% identical, preferably at least 95 or 98% identical at the amino acid level over at least 20, preferably 50 or 100 amino acids with a sequence as shown SEQ ID NO:1, SEQ ID NO: 2 or SEQ ID NO:3.

Although homology can also be considered in the art in terms of similarity (i.e. amino acid residues having similar chemical properties/functions), in the context of the present invention it is preferred to express homology in terms of sequence identity. The % identity of a polypeptide Js determined by FASTA (Pearson and Lipman, 1988) analysis (GCG program) using the default settings and a query sequence of at least 50 amino acids in length, and whereby the FASTA analysis aligns the two sequences over a region of at least 50 amino acids. More preferably, the FASTA analysis aligns the two sequences over a region of at least 100 amino acids. More preferably, the PASTA analysis aligns the two sequences over a region of at least 250 amino acids. Even more preferably, the FASTA analysis aligns the two sequences over a region of at least 350 amino acids, The terms "variant" or "derivative" in relation to the amino acid sequences of the present invention and/or for use in the present invention includes any substitution of, variation of, modification of, replacement of, deletion of or addition of one (or more) amino acids from or to the sequence providing the resultant amino acid sequence preferably has at least 25 to 50% of the biological activity as a naturally occurring TNAP more preferably at least substantially the same activity. The relevant biological activity includes the ability of the variant or derivative to bind to natural TNAP ligands.

In general, preferably less than 20%, 10% or 5% of the amino acid residues of a variant or derivative are altered as compared with the corresponding region of the naturally occurring TNAP, the percentage typically being lower the shorter the amino, acid sequence e.g. less than 5% for amino acid sequences of 20 amino acids or less.

The term "TNAP" also encompasses fragments of the above mentioned full-length polypeptides and variants thereof, including fragments of the sequences set out in the sequence listing herein. Preferred fragments include those that include an epitope. Suitable fragments will be at least about 6 or 7 amino acids in length, e.g. at least 10, 12, 15 or 20 amino acids in length. They may also be less than 200, 100 or 50 amino acids in length. Polypeptide fragments of the polypeptides depicted in the sequence listings and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

In an embodiment, the term TNAP does not encompass placental AP.

TNAP Binding Agents

When used herein, the phrase "TNTAP binding agent" refers to a moiety that recognises and/or binds to TNAP.

Preferred TNAP binding agents are polypeptides or compounds identified as having binding affinity to TNAP. For example, $T_{TNAP}$ has been characterised as having a collagen binding loop (Mornet et al., 2001). Accordingly, the TNAP agent may be collagen, preferably type I collagen.

Particularly preferred TNAP binding agents are anti-TNAP antibodies (naturally occurring or recombinant, from any source).

The term "antibody" as used in this invention includes intact molecules as well as fragments thereof, such as Fab, F(ab')2, and Fv which are capable of binding the epitopic determinant These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;
(2) Fab', the fragment of an antibody molecule can be obtained by treating whole antibody with pepsin, followed by reduction, to yield an intact light chain and a portion of the heavy chains two Fab' fragments are obtained per antibody molecule;
(3) (Fab')2, the fragment of the antibody that can be obtained by treating whole antibody with the enzyme pepsin without subsequent reduction; F(ab)2 is a dimer of two Fab' fragments held together by two disulfide bonds;
(4) Fv, defined as a genetically engineered fragment containing the variable region of the light chain and the variable region of the heavy chain expressed as two chains; and
(5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbour Laboratory. New York (1988), incorporated herein by reference).

Antibodies of the present invention can be prepared using cells expressing TNAP, full length TNAP or fragments thereof as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide may then be used to immunise the animal (e.g., a mouse or a rabbit).

If desired, polyclonal antibodies can be further purified, for example, by binding to and ehition from a matrix to which the peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

Monoclonal antibodies may be prepared using any technique which provides for the production of antibody molecules by continuous cell lines in culture, such as, for example, the hybridoma technique, the human B-cell hybridoma technique, and the EBV-hybiidoma technique (Kohler et al., 1975; Kozbor et al., 1985; Cote et al., 1983; Cole et al., 1984).

Methods known in the art also allow antibodies exhibiting binding for TNAPP to be identified and isolated from antibody expression libraries.

Antibodies with an epitopic specificity which is the same as or similar to that of mAb STRO-3 can be identified by their ability to compete with that particular mAb for binding to TNAP (e.g. to cells bearing TNAP, such as MPCs, or to isolated TNAP protein or fragments thereof). Using receptor chimeras (Rucker et al., 1996) or other techniques known to those skilled in the art, the binding site of STRO-3 mAb may be mapped.

It is also possible to determine, without undue experimentation, if a monoclonal antibody has the same specificity as STRO-3 mAb by ascertaining whether the former prevents the latter from binding to TNAP. If the monoclonal antibody being tested competes with STRO-3 mAb, as shown by a decrease in binding by STRO-3 mAb, then the two monoclonal antibodies bind to the same, or a closely related, epitope.

Still another way to determine whether a monoclonal antibody has the specificity of STRO-3 mAb is to pre-incubate the monoclonal antibody being tested with TNAP, and then add STRO-3 mAb to determine if STRO-3 mAb is inhibited in its ability to bind to TNAP. If the binding of STRO-3 mAb is inhibited then, in all likelihood, the monoclonal antibody being tested has the same, or functionally equivalent, epitopic specificity as STRO-3 mAb.

Monoclonal antibodies useful in the present invention can be engineered so as to change the isotype of the antibody. Fox example, an IgG2A isotype can be engineered as an IgG1, IgG2B, or other isotypes.

It will be appreciated that a TNAP binding agent such as an antibody of the invention may be conjugated to a compound that is useful, for example, in cell separation, therapeutic or diagnostic applications. In one example, an antibody of the invention is conjugated to a label. The label may be any entity the presence of which can be readily detected. For example, the label may be a direct label, such as those described in detail in May et. al., U.S. Pat. No. 5,656,503. Direct labels are entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

Conjugation of a label to a binding agent such as an antibody of the invention can be by covalent or non-covalent (including hydrophobic) bonding, or by adsorption. Techniques for such conjugation are commonplace in the art and may be readily adapted for the particular reagents employed.

A binding agent for use in the methods of the invention, such as an antibody of the invention, may also be coated onto a solid support. For example, the antibody can be coated on, a synthetic plastics material, magnetic, particle, microtitre assay plate, microarray chip, latex bead, filter comprising a cellulosic or synthetic polymeric material, glass or plastic slide, dipstick, capillary fill device and the like.

A binding agent for use in the methods of the invention, such as an antibody of the invention, may also be incorporated into a device for cell separation. For example, the device may be an automated cell selection device based on MACS technology. Such a device enables large scale magnetic cell selection in a closed and sterile system. For example, the device may comprise an integrated computer, a magnetic separation unit, a peristaltic pump and various pinch valves. The integrated computer preferably controls all components of the instrument and directs the system to perform procedures in a standard sequence. The magnetic separation unit preferably includes a movable permanent magnet and a holder for the selection column. The peristaltic pump preferably controls the flow rate through the tubing set. Pinch valves can be used to ensure controlled flow of buffer and cell suspension. Before selection the cells are magnetically labeled by using an antibody of the present invention. A single-use tubing set, including separation columns, may then be attached to the device and the cell preparation bag, containing the labeled cells-, may be connected to the tubing set. After starting the selection program, the system automatically applies the cell sample to the separation column, performs a series of washing steps depending on the program chosen and finally elutes the purified target cells.

Cell-Sorting Techniques

The ability to recognise adult multipotential cells with TNAP binding agents, such as anti-TNAP antibodies, allows not only for the identification and quantification of these cells in tissue samples, but also for their separation and enrichment in suspension. This can be achieved by a number of cell-sorting techniques by which cells are physically separated by reference to a property associated with the cell-antibody complex, or a label attached to the antibody. This label may be a magnetic particle or a fluorescent molecule. The antibodies may be cross-linked such that they form aggregates of multiple cells, which are separable by their density. Alternatively the antibodies may be attached to a stationary matrix, to which the desired cells adhere.

Various methods of separating antibody-bound cells from unbound cells are known. For example, the antibody bound to the cell (or an anti-isotype antibody) can be labelled and then the cells separated by a mechanical cell sorter that detects the presence of the label. Fluorescence-activated cell sorters are well known in the art. In one embodiment, the anti-TNAP antibody is attached to a solid support. Various solid supports are known to those of skill in the art, including, but not limited to, agarose beads, polystyrene beads, hollow fiber membranes, polymers, and plastic petri dishes. Cells that are bound by the antibody can be removed from the cell suspension by simply physically separating the solid support from the cell suspension.

Super paramagnetic microparticles may be used for cell separations. For example, the microparticles may be coated with anti-TNAP antibodies. The antibody-tagged, super paramagnetic microparticles may then be incubated with a solution containing the cells of interest. The microparticles bind to the surfaces of the desired adult multipotential cells, and these cells can then be collected in a magnetic field.

In another example, the cell sample is allowed to physically contact, for example, a solid phase-linked anti-TNAP monoclonal antibody. The solid-phase linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads. The exact conditions and duration of incubation for the solid phase-linked antibodies with the adult multipotential cell containing suspension will depend upon several factors specific to the system employed. The selection of appropriate conditions, however, is well within the skill of the art.

The unbound cells are then eluted or washed away with physiologic buffer after allowing sufficient time for the adult multipotential cells t be bound. The unbound cells can be recovered and used for other purposes or discarded after appropriate testing has been done to ensure that the desired separation had been achieved. The bound cells are then separated from the solid-phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting an enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either said enriched fraction or the unbound fraction may be cryopreserved in a viable state for later use according to conventional technology or introduced into the transplant recipient Production of Genetically Modified Cells In one embodiment the present invention relates to genetically modified cells, particularly genetically modified adult multipotential cells of the invention. Preferably, the cells are genetically modified to produce a heterologous protein. Typically, the cells will be genetically modified such that the heterologous protein is secreted from the cells. However, in an embodiment the cells can be modified to express a functional non-protein encoding polynucleotide such as dsRNA (typically for RNA silencing), an antisense oligonucleotide or a catalytic nucleic acid (such as a ribozyme or DNAzyme).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into an adult multipotential cell or modification of an endogenous gene within adult multipotential cell. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., 1992) or culturing with, viral supernatant alone with or without appropriate growth factors and polycations (Xu et al., 1994).

An exogenous polynucleotide is preferably introduced to a host cell in a vector. The vector preferably includes the necessary elements for the transcription and translation of the inserted coding sequence. Methods used to construct such vectors are well known in the art. For example, techniques for constructing suitable expression vectors are described in detail in Sambrobk et al., Molecular Cloning: A Laboratory Manual, Cold Spring Harbor Press, N.Y. (3rd Ed., 2000); and Ausuhel et al., Current Protocols in Molecular Biology, John Wiley & Sons, Inc., New York (1999).

Vectors may include but are not limited to viral vectors, such as retroviruses, adenoviruses, adeno-associated viruses, and herpes simplex viruses; cosmids; plasmid vectors; synthetic vectors; and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, ρSV2CAT, pXtl from Stratagene; and pMSG, pSVL, pBPV and ρSVK3 from Pharmacia.

Preferred vectors include retroviral vectors (see, Coffin et al., "Retroviruses", Chapter 9 pp; 437-473, Cold Springs Harbor Laboratory Press, 1997). Vectors useful in the invention can be produced recombinantly by procedures well known in the art. For example. WO94/29438, WO97/21824 and WO97/21825 describe the construction of retroviral packaging plasmids and packing cell lines. Exemplary vectors include the pCMV mammalian expression vectors, such as pCMV6b and pCMVGc (Chiron Corp.), pSFFV-Ne θ, and pBlescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MINGFR and MINT. Additional vectors include those based on Gibbon ape leukemia virus (GALV) and Moloney murine sarcoma virus (MOMSV) and spleen focus forming virus (SFFV). Vectors derived from the murine stem cell virus (MESV) include MESV-MiLy.

Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the at Numerous promoters are known in addition to the promoter of the LTR, Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; and the Granzyme B promoter. Additionally inducible or multiple control elements may be used. The selection of a suitable promoter will be apparent to those sidled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbours a provints. The provirus has been crippled so that although it may produce all the proteins required to assemble infectious viruses, its own RNAA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSL-CRIP, RDI 14, GP7C-tTA-G10, ProPak-A (PPA-6), and PT67. Reference is made to Miller fet al., 1986; Miller et al., J 1989; Danos et al., 1988; Pear et al., 1993; and Finer et al., 1994.

Other suitable vectors include adenoviral vectors (see, Frey et al., 1998; and WO 95/27071) and adeno-associated viral vectors. These vectors are all well known in the art, e.g., as described in Chatterjee et al., 1996; and Stem Cell Biology and Gene Therapy, eds. Quesenbeπy et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences. Preferably the additional nucleic acid sequence is a polynucleotide which encodes a selective marker, a structural gene, a therapeutic gene, or a cytokine/chemokine gene.

A selective marker may be included in the construct, or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial MsD gene, murine CD24 (HSA), murine CDSa (IyQ, bacterial genes which confer resistance to puromycin or pMeomycin and β-glactosidaee.

The additional polynucleotide sequence(s) may be introduced into the host cell on the same vector or may be introduced into the host cells on a second vector. In a preferred embodiment, a selective marker will be included on the same vector as the polynucleotide.

The present invention also encompasses genetically modifying the promoter region of an endogenous gene such that expression of the endogenous gene is up-regulated resulting in the increased production of the encoded protein compared to a wild type adult multipotential cells, Administration of Stimulatory Factors Methods of the present invention may involve the use one or more stimulatory factors. Furthermore, compositions of the invention may comprise one or more stimulatory factors.

In one embodiment, a method of the invention may involve administering one or more stimulatory factors such as 1α,25-dihydroxyvitamk $D_3$ (1,25D), platelet derived growth factor (PDGF), tumor necrosis factor α(TNF-α), interleukin-1β (IL-1β) and stromal derived factor 1α (SDF-1α) topically, systematically, or locally such as within an implant or device.

In particular embodiments, a preferred range for stimulatory factors may be 0.1 nM-0.1 M, 0.1 nM-0.05 M, 0.05 nM-15 μM or 0.01 uM-10 μM. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

The amount of stimulatory factor in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous t formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier.

It will be appreciated that the stimulatory factor may be administered in the form of a composition comprising a pharmaceutically acceptable carrier or excipient.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known, in the art. Except insofar as any conventional media or agent is incompatible with the active compound, use thereof in the pharmaceutical compositions of the invention is contemplated. Supplementary active compounds can also be incorporated into the compositions.

Pharmaceutical formulations for parenteral administration may include liposomes. Liposomes and emulsions are well known examples of delivery vehicles or carriers that are especially useful for hydrophobic drugs. Depending on biological stability of the therapeutic reagent, additional strategies for protein stabilization may be employed. Furthermore, one may administer the drug in a targeted drug delivery system, for example, in a liposome coated with target-specific antibody. The liposomes will bind to the target protein and be taken up selectively by the cell expressing the target protein.

Therapeutic compositions typically should be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol propylene glycol, and liquid polyethylene glycol, and fee like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

Prolonged absorption of the injectable compositions can be brought about by including in the composition an agent which delays absorption, for example, monostearate salts and gelatin. Moreover, the stimulatory factor may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Additionally, suspensions of stimulatory factors may be prepared as appropriate oily suspensions for injection. Suitable lipophilic solvents or vehicles include fatty oils such as sesame oil; or synthetic fatty acid esters, such as ethyl oleate or triglycerides; or liposomes, Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. Ia the case of sterile powders for the preparation of sterile injectable solutions, the preferred methods of preparation are vacuum drying and freeze-drying which yields a powder of the active ingredient plus any additional desired ingredient from a previously sterile-filtered solution thereof. La accordance with an alternative aspect of the invention, the stimulatory factor may be formulated with one or more additional compounds that enhance its solubility.

If the compositions are to be administered by inhalation, they may be conveniently delivered in the form of an aerosol spray presentation from pressurized packs or a nebuliser; together with the use of a suitable propellant, e.g., dichlorodifluoroinethane, tr chlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin, for example, for use in an inhaler may be formulated containing a powder mix of the compound and a suitable powder base such as starch or lactose.

Cellular Compositions

The cellular compositions of the present invention, such as those comprising adult multipotential cells, are useful for the regeneration of tissue of various types, including bone, cartilage, tendon, ligament, muscle, skin, and other connective tissue, as well as nerve, cardiac, liver, lung, kidney, pancreas, brain, and other organ tissues.

In some embodiments, the compositions of the present invention may be administered in combination with an appropriate matrix, for instance, for supporting the cells and providing a surface for bone, cartilage, muscle, nerve, epidermis and/or other connective tissue growth. The matrix may be in the form of traditional matrix biomaterials. The matrix may provide slow release of cells and/or the appropriate environment for presentation thereof: In some embodiments, various collagenous and non-collagenous proteins are expected to be upregulated and secreted from the cells. This phenomenon accelerates tissue regeneration by enhancing matrix deposition. Matrix proteins can also be expressed in the genetically engineered cells and enhance the engraftment and attachment of transplanted cells into the transplant area.

The choice of matrix material is based on biocompatibility, biodegradability, mechanical properties, cosmetic appearance and interface properties. The particular application of the cellular based compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The cellular compositions of the invention may be used to treat patients requiring the repair or replacement of cartilage or bone tissue resulting from disease or trauma or failure of the tissue to develop normally, or to provide a cosmetic function, such as to augment facial or other features of the body. Treatment may entail the use of the cells of the invention to produce new cartilage tissue or bone tissue. For example, compositions comprising undifferentiated or chondrogenic differentiation-reduced precursor cells may be used to treat a cartilage condition, for example, rheumatoid arthritis or osteoarthritis or a traumatic or surgical injury to cartilage. As another example, compositions comprising bone precursor cells may be used to treat bone conditions, including metabolic and non-metabolic bone diseases. Examples of bone conditions include meniscal tears, spinal fusion, spinal disc removal, spinal reconstruction, bone fractures, bone/spinal deformation, osteosarcoma; myeloma, bone dysplasia, scoliosis, osteoporosis, periodontal disease, dental bone loss, osteomalacia, rickets, fibrous osteitis, renal bone dystrophy, and Paget's disease of bone.

The cellular compositions of the invention may be administered alone or as admixtures with other cells. Cells that may be administered in conjunction with the compositions of the present invention include, but are not limited to, other multipotent or pluripotent cells or chondrocytes, chondroblasts, osteocytes, osteoblasts, osteoclasts, bone lining cells, stem cells, or bone marrow cells. The cells of different types may be admixed with a composition of the invention immediately or shortly prior to administration, or they may be co-cultured together for a period of time prior to administration.

The cellular compositions of the invention may be administered with other beneficial drugs or biological molecules (growth factors, trophic factors). When the adult multipotential cells are administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, $TPO_5$ IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRAMLAST, REMICADE, SIROLIMUS, and NSAIDs (non-steroidal anti-inflammatory drugs; e.g., TEPOXALIN-TOLMETIN, SUPROFEN); immunosuppressive/immunomodulatory agents (e.g., calcineurin inhibitors, such as cyclosporins tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, Pack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

In one embodiment, cellular compositions of the invention are administered as undifferentiated cells, i.e., as cultured in Growth Medium. Alternatively, the cellular compositions way be administered following exposure in culture to conditions that stimulate differentiation toward a desired phenotype, for example, an osteogenic phenotype.

The cellular compositions of the invention may be surgically implanted, injected, delivered (e.g., by way of a catheter or syringe), or otherwise administered directly or indirectly to the site in need of repair or augmentation. The cells may be administered by way of a matrix (e.g., a three-dimensional scaffold). The cells may be administered with conventional pharmaceutically acceptable carriers. Routes of administration of the cells of the invention or compositions or components (e.g., ECM, cell lysate, conditioned medium) thereof include intramuscular, ophthalmic, parenteral (including intravenous), intraarterial, subcutaneous, oral, and nasal administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration.

When cells are administered in semi-solid or solid devices, surgical implantation into a precise location in the body is typically a suitable means of administration. Liquid or fluid pharmaceutical compositions, however, may be administered to a more general location (e.g., throughout a diffusely affected area, for example), from which they migrate to a particular location, e.g., by responding to chemical signals.

Other embodiments encompass methods of treatment by administering pharmaceutical compositions comprising cellular components (e.g., cell lysates or components thereof) or products (e.g., extracellular matrix, trophic and other biological factors produced through genetic modification).

Dosage forms and regimes for administering cellular compositions described herein are developed in accordance with good medical practice, taking into account the condition of the individual patient, e.g., nature and extent of the condition being treated, age, sex, body weight and general medical condition, and other factors known to medical practitioners. Thus, the effective amount of a pharmaceutical composition to be administered to a patient is determined by these considerations as known in the art.

In some embodiments of the invention, it may not be necessary or desirable to immunosuppress a patient prior to initiation of therapy with cellular compositions of the present invention. Accordingly, transplantation with allogeneic, or even xenogeneic, adult multipotential cells may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. Adult multipotential cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art, As an alternative, adult multipotential cells may be genetically modified to reduce their immunogenicity.

Survival of transplanted cells in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the target tissue, and examining it visually or through a microscope. Alternatively, cells can be treated with stains that are specific for cells of a specific lineage. Transplanted cells can also be identified by prior incorporation of tracer dyes such as rhodamine-or fluorescein-labeled microspheres, fast blue, bisbenzamide, ferric microparticles, or genetically introduced reporter gene products, such as beta-galactosidase or beta-glucuronidase.

Functional integration of transplanted cells into a subject can be assessed by examining restoration of the function that was damaged or diseased, for example, restoration of joint or bone function, or augmentation of function.

Cellular compositions of the invention may include one or more bioactive factors, for example but not limited to a growth factor, a differentiation-inducing factor, a cell survival factor such, as caspase inhibitor, or an anti-inflammatory agent such as p38 kinase inhibitor.

Alternatively, cells to be transplanted may be genetically engineered to express such growth factors, antioxidants, antiapoptotic agents, or anti-inflammatory agents. Pharmaceutical compositions of the invention may comprise homogeneous or heterogeneous populations of cells, extracellular matrix or cell lysate thereof, or conditioned medium thereof in a pharmaceutically acceptable carrier. Pharmaceutically acceptable carriers for the cells of the invention include organic or inorganic carrier substances suitable which do not deleteriously react with the cells of the invention or compositions or components thereof. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring, Pharmaceutical carriers suitable for use in the present invention, are known in the art and are described, for example, in Pharmaceutical Sciences (17th Ed., Mack Pub. Co., Easton, Pa. and WO 96/05309.

One or more other components may be added to transplanted cells, including selected extracellular matrix components, such as one or more types of collagen known in the art, and/or growth factors, platelet-rich plasma, and drugs. Alternatively, the cells of the invention may be genetically engineered to express and produce for growth factors. Details on genetic engineering of the cells of the invention are provided herein.

IQ a non-limiting embodiment, a formulation comprising the cells of the invention is prepared for administration directly to the site where the production of new tissue, such as bone tissue, is desired. For example, and not by way of limitation, the cells may be suspended in a hydrogel solution for injection. Examples of suitable hydrogels for use in the invention include self-assembling peptides, such as RAD1 6. Alternatively, the hydrogel solution containing the cells may be allowed to harden, for instance in a mold, to form a matrix having cells dispersed therein prior to implantation. Or, once the matrix has hardened, the cell formations may be cultured so that the cells are mitotically expanded prior to implantation. The hydrogel is an organic polymer (natural or synthetic) which is cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are cross-linked Ionically, or block polymers such as polyethylene oxide-polypropylene glycol block copolymers which are crosslinked by temperature or pH, respectively. In some embodiments, the support for the cells is biodegradable.

In some embodiments of the invention, the formulation comprises an in situ polyrnemable gel, as described, for example, in U.S. Patent Application Publication 2002/0022676; Anseth et al, 2002; and Wang et al., 2003.

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers ox polymers can also be used. Examples of acidic groups axe carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), polyvinyl imidazole), and some ïmmo substituted polyphosphates. The ammonium or quaternary salt of the polymers can also be formed from the backbone nitrogens or pendant imïno groups. Examples of basic side groups are amino and imi πo groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can b e synthesized that degrade by hydrolysis by incorporating monomers having imidazole, amino acid ester, or glycerol side groups. For example, a polyanionic poly[bis(carboxylatopheaioxy)] phosphazene (PCPP) can be synthesized, which is cross-linked with dissolved multivalent cations in aqueous media at room temperature or below to form hydrogel matrices.

Biodegradable polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

Hydrolysis of the side chain results in erosion of the polymer. Examples of hydrolyεtng side chains are unsubstituted and substituted imidazoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom, Other "R" groups can be organic residues that do not participate in hydrolysis, such as methyl phenoxy groups or other groups shown in the scientific paper of Allcock et al. (1977). Methods of synthesis of the hydrogel materials, as well as methods for preparing such hydrogels, are known in the art.

Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation, of tissue or its physicochemical characteristics, or as support for the viability of the cells, or inhibition of inflammation or rejection. The cells may be covered by an appropriate wound covering to prevent cells from leaving the site. Such wound coverings are known as those of skill in the art.

Fibrin Glue

Fibrin glues are a class of surgical sealants which have been used in various clinical settings. As the skilled address would be aware, numerous sealants are useful in compositions of the invention. However, a preferred embodiment of the invention relates to the use of fibrin glues with cells of the invention.

When used herein the term "fibrin glue" refers to the insoluble matrix formed by the cross-linking of fibrin polymers in the presence of calcium ions. The fibrin glue may be framed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XI). As will be appreciated by those sMlled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor Xiπ. The catalyst of fibrin glue formation may be derived from blood plasma, cryoprecipitate or other plasma fractions containing fibrinogen or thrombin. Alternatively, the catalyst may be produced by recombinant DNA technology.

The rate at which the clot forms is dependent upon the concentration of thrombin mixed with fibrinogen. Being an enzyme dependent reaction, the higher the temperature (up to 37° C.) the faster the clot formation rate. The tensile strength of the clot is dependent upon the concentration of fibrinogen used.

Use of fibrin glue and methods for its preparation and use are described by I-fiεh et al. in U.S. Pat. No. 5,643,192. Hirsh discloses the extraction of fibrinogen and thrombin components from a single donor, and the combination of only these components for use as a fibrin glue. Marx, U.S. Pat. No. 5,651,982, describes another preparation and method of use For fibrin glue. Marx provides a fibrin glue with liposomes for use as a topical sealant in mammals. The preparation and use of a topical fibrinogen complex (TFC) for wound healing is known in the field. PCT Application No. PCT/US95/15S76, PCT Publication No, WO96/17633—of The American Red Cross discusses TFC preparations continuing fibrinogen, thrombin, and calcium chloride, for example, at pages 16-18 of PCT Publication No. WO96/17633.

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body.

Formulation of a Bone Tissue Patch

Culture or co-cultures of cells of the invention in a pre-shaped well enables the manufacture of a tissue patch of pre-determined thickness and volume. The volume of the resulting tissue patch is dependent upon the volume of the well and upon the number of adult multipotential cells in the well. Tissue of optimal pre-determined volume may be prepared by routine experimentation by altering either or both of the aforementioned parameters.

The cell contacting surface of the well may be coated with a molecule that discourages adhesion of adult multipotential cells to the cell contacting surface. Preferred coating reagents include silicon based reagents i.e., dichlorodimethylsilane or polytetrafluoroethylene based reagents, i.e., TEFLON. Procedures for coating materials with silicon based reagents, specifically dichlorodimethylsilane, are well known in the art. See for example, Sambrook et al. (1989). "Molecular Cloning A Laboratory Manual". Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., TEFLON, Untreated cell culture plastics, i.e., plastics that have not been treated with or made from materials that have an electrostatic charge are commercially available, and may be purchased, for example, from Falcon Labware, Becton-Dïckinson, Lincoln Park, NJ The aforementioned materials, however, are not meant to be limiting. It is appreciated that any other pliable or moldable biocompatible material that inherently discourages the attachment of adult multipotential cells may be useful in the practice of the instant invention.

Cells of the invention in suspension may be seeded into and cultured in the pre-shaped well. The cells may the induced to differentiate to a chondrogenic or osteogenic phenotype in culture in the well or may have been induced to differentiate prior to seeding in the well. The cells may be diluted by the addition of culture medium to a cell density of about $1\times10^5$ to $1\times10^9$ cells per milliliter.

The cells may form a cohesive plug of cells. The cohesive plug of cells may be removed from the well and surgically implanted into the tissue defect. It is anticipated that any undifferentiated cells, such as adult multipotential cells of invention, may differentiate in situ thereby to form tissue in vivo.

Bone defects may be identified inferentially by using computer aided tomography (CAT scanning); X-ray examination, magnetic resonance imaging (MRI), analysis of synovial fluid or serum markers or by any other procedures known in the art. Defects in mammals also are readily identifiable visually during arthroscopic examination or during open surgery of the joint. Treatment of the defects can be effected during an arthroscopic or open surgical procedure using the methods and compositions disclosed herein.

Accordingly, once the defect has been identified, the defect may be treated by the following steps of (1) surgically implanting at the pre-determined site a tissue patch prepared by the methodologies described herein, and (2) permitting the tissue patch to integrate into pre-determined site.

The tissue patch optimally has a size and shape such that when the patch is implanted into the defect, the edges of the implanted tissue contact directly the edges of the defect. In addition, the tissue patch nay be fixed in place during the surgical procedure. This can be effected by surgically fixing the patch into the defect with biodegradable sutures and/or by applying a bioadhesive to the region interfacing the patch and the defect.

In some instances, damaged tissue may be surgically excised prior to the implantation of the patch of tissue.

Transplantation of Cells Using Scaffolds

The cellular compositions of the invention or co-cultures thereof may be seeded onto or into a three-dimensional scaffold and implanted in vivo, where the seeded cells will proliferate on the framework and form a replacement tissue, such as bone tissue in vivo in cooperation with the cells of the patient.

For example, but not by way of limitation, the scaffold may be designed such that the scaffold structure: (1) supports the seeded cells without subsequent degradation; (2) supports the cells from the time of seeding until the tissue transplant is remodeled by the host tissue; (2) allows the seeded cells to attach, proliferate, and develop into a tissue structure having sufficient mechanical integrity to support itself in vitro, at which point, the scaffold is degraded. A review of scaffold design is provided by Hutmacher (2001).

Scaffolds of the invention can be administered in combination with any one or more growth factors, cells, for example stem cells, bone marrow cells, chondrocytes, chondroblasts, osteocytes, osteoblasts, osteoclasts, bone lining cells, or their precursors, drugs or other components described above that stimulate tissue formation or otherwise enhance or improve the practice of the invention. The cells of the invention to be seeded onto the scaffolds may be genetically engineered to express growth factors or drugs.

The cells of the invention can be used to produce new tissue in vitro, which can then be implanted, transplanted or otherwise inserted into a site requiring tissue repair, replacement oτ augmentation in a patient In a non-limiting embodiment, the cells of the invention are used to produce a three-dimensional tissue construct in vitro, which is then implanted in vivo. As an example of the production of three-dimensional tissue constructs, see U.S. Pat. No. 4,963,489, which is incorporated herein by reference. For example, the cells of the invention may be inoculated or "seeded" onto a three-dimensional framework or scaffold, and proliferated or grown in vitro to form a living tissue that can be implanted in vivo.

The cells of the invention can be grown freely in a culture vessel to sub-confmβncy or confluency, lifted from the culture and inoculated onto a three-dimensional framework. Inoculation, of the three-dimensional framework with a high concentration of cells, e.g., approximately $10^6$ to $5\times10^7$ cells per milliliter, will result in the establishment of the three-dimensional support in relatively shorter periods of time.

Examples of scaffolds which may be used in the present invention include nonwoven mats, porous foams, or self assembling peptides. Nonwoven mats may, for example, be formed using fibers comprised of a synthetic absorbable copolymer of glycolic and lactic acids (PGA/PLA), sold under the tradename VICRYL (Ethicon, Inc., Somerville, NJ). Foams, composed of, for example, poly(epsilon-caprolactone)/poly(glycolic acid) (PCL/PGA) copolymer, formed by processes such as freeze-drying, or lyophilized as discussed in U.S. Pat. No. 6,355,699, are also passible scaffolds. Hydrogels such as self-assembling peptides (e.g., RAD16) may also be used. These materials are frequently used as supports for growth of tissue.

The three-dimensional framework may be made of ceramic materials including, but not limited to: mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS (University of Florida, Gainesville, Fla.), and mixtures thereof. There are a number of suitable porous biocompatible ceramic materials currently available on the commercial market such as SURGIBON (Unilab Surgibone, Inc., Canada), ENDOBON (Merck Biomaterial France, France), CEROS (Mathys, A-G., Bettlach, Switzerland), and INTERPORE (Interpoie. Irvine, Calif., United States), and mineralized collagen bone grafting products such as HEALOS (Orquest, Inc., Mountain View, Calif.) and VITOSS, RHAKOSS- and CORTOSS (Orthovila, Malvern, Pa.). The framework may be a mixture, blend or composite of natural and/or synthetic materials. In some embodiments, the scaffold is in the form of a cage. In a preferred embodiment, the scaffold is coated with collagen.

According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling.

In another preferred embodiment the cells of the invention are seeded onto foam scaffolds that may be composite structures. In addition, the three-dimensional framework may be molded into a useful shape, such as that of the external portion of the ear, a bone, joint or other specific structure in the body to be repaired, replaced or augmented.

In another preferred embodiment, the cells are seeded onto a framework comprising a prosthetic device for implantation into a patient, as described in U.S. Pat. No. 6,200,606, incorporated herein by reference. As described therein, a variety of clinically useful prosthetic devices have been developed for use in-bone and cartilage grafting procedures, (see e.g. Bone Grafts and Bone Substitutions. Ed. M. B. Habal & A. H. Reddi, W. B. Saunders Co., 1992). For example, effective knee and hip replacement devices have been and continue to be widely used in the clinical environment Many of these devices are fabricated using a variety of inorganic materials having low immunogenic activity, which safely function in the body. Examples of synthetic materials which have been tried and proven include titanium alloys, calcium phosphate, ceramic hydroxyapatite, and a variety of stainless steel and cobalt-chrome alloys. These materials provide structural support and can form a scaffolding into which host vascularization and cell migration can occur.

The framework may be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosamhioglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PU RPANN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

In some embodiments, the surface of the scaffold is textured. For example, in some aspects of the invention, the scaffold is provided with a groove and ridge pattern. The grooves are preferably less than about 500 microns, more preferably less than about 100 microns, and most preferably between about 10 nanometers and 10 microns, Such-"microgrooves" allow the cells to align and/or migrate guided by the surface grooves.

In some embodiments, it is important to re-create in culture the cellular microenvironment found in vivo, such that the extent to which, the cells of the invention are grown prior to implantation in vivo or use in vitro may vary. In addition, growth factors, chondrogenic differentiation inducing agents, osteogenic inducing agents, and angiogenic factors may be added to the culture medium prior to, during, or subsequent to inoculation of the cells to trigger differentiation and tissue formation by the cells or progeny thereof.

The three-dimensional framework may be modified so that the growth of cells and the production of tissue thereon is enhanced, or so that the risk of rejection of the implant is reduced. Thus, one or more biologically active compounds, including, but not limited to, antiinflammatories, immunosuppressants or growth factors, may be added to the framework.

EXAMPLES

The present invention will now be described in more detail with reference to the following non-limiting examples.

Example 1: Generation of the mAb STRO-3

Materials and Methods

Human MPC Cultures

Stromal cultures were established, essentially as described previously (Gronthos et al., 2003). The use of normal bone marrow (BM) cells for these studies was approved by the Human Ethics Committee of the Royal Adelaide Hospital, Australia. After washing-thrice in "HHF" (Hanks Buffered Salt Solution (HBSS) supplemented with 20 mM HEPES and 5% FCS), the $1-5 \times 10^7$ bone marrow mononuclear cells (BMMNCs) were resuspended in 10 ml of alpha modification of Eagles' medium (α-MEM: Flow Laboratories, Irvine, Scotland) supplemented with Folic acid (0.01 mg/ml), myo-inositol (0.4 mg/ml) (Sigma Chemical Co. St Louis, MO), 50 mM/L 2-mercaptoethanol, imM/L hydrocortisone sodium succinate (Sigma), 12.5% FCS, and 12.5% horse serum (CSL, Melbourne, Australia) and cultured in 25 cm² flasks (Becton Dickinson Labware, Franklin Lakes, NJ), Upon development of a confluent stromal layer, the cells were detached using 0.05% (w/v) trypsin-EDTA in PBS (Gibco) and replated in the same medium at approximately $1-2 \times 10^4$ cells per cm² in 2×75 cm² tissue culture flasks (Becton Dickinson Labware, Franklin Lakes, NJ).

Results and Discussion

A panel of mouse monoclonal antibodies reactive with human MPC were generated following the fusion of splenocytes derived from mice immunized with cultured human BM stromal cells. Preliminary screens were designed to identify mAbs which reacted with normal human bone cells (NHBC) and MPC but exhibited limited reactivity with the majority of BMMNC. One mAb, STRO3, was initially selected for further analysis due to its unique pattern of reactivity with different cell lines. Tertiary clones of the STRO-3 hybridoma were isolated by limiting dilution in 96-well plates and subsequently screened as described above. The distribution patterns of STRO-3 with various stromal cell types are summarized in Table 1. The mAb STRO-3 exhibited reactivity to a proportion of NHBC and MPC and with only a minor proportion of BMMNC. The immunoglobulin isotype of STRO-3 from tertiary hybridoma supernatants was determined to be IgGi using an isotype detection kit (Roche).

TABLE 1

Immunoreactivity of STRO-3 supernatants from tertiary cloned hybridomas on different cell types using in situ immunofluorecence as described in the methods.

| Cell Type | In Situ Immunofluoresce Staining |
|---|---|
| Peripheral blood mononuclear cells | NS |
| Bone marrow mononuclear cells | +/− (neutrophils) |
| Ex vivo expanded MPC | +/− |
| Cultured normal human bone cells | ++/− |
| Human foreskin fibroblasts | +/− |
| Human ubilical vein endothelial cells | NS |
| Murine bone marrow stromal line BMS2 | NS |

TABLE 1-continued

Immunoreactivity of STRO-3 supernatants from tertiary cloned hybridomas on different cell types using in situ immunofluorecence as described in the methods.

| Cell Type | In Situ Immunofluoresce Staining |
|---|---|
| Human osteosarcoma cell line SAOS-2 | ++ |
| Human osteosarcoma cell line MG63 | NS |
| Human osteosarcoma cell line HOS | ++ |

(+) Low fluorescence staining on all cells
(++) High fluorescence staining on all cells
(NS) No fluorescence staining on cells
(+/−), (−H−/−) Fluorescence Staining on a subpopulation of cells Example 2: Molecular Characterization of the STRO-3 Antigen Materials and Methods Expression Cloning of the cDNA Encoding STRO-3 Antigen The cDNA encoding the cell surface antigen identified by the mAb STRO-3 was isolated from a human bone marrow stromal cell cDNA library hi the retroviral vector, pRUFneo as described (Zannettino et al., 1996). Briefly, cDNA synthesised from mRNA from HBMSC cultures was cloned into the retroviral vector pRUFneo. Plasmid DNA from the library was used to transfect a viral packaging line (PA317). Virus containing supernatant from these cells was used to infect the packing cell line ψ2, which in turn was used to infect the murine factor-dependent cell line BAF-3. Infected cells were selected for G418 resistance, labelled with STRO-3 antibody and cells specifically binding the antibody were isolated by immunomagnetic bead selection (Dynabead, Dynal, Oslo, Sweden). After expansion of the initially selected cells in culture, immunomagnetic bead selection was repeated a further two times. BAF-3 cells which demonstrated specific binding of STRO-3 antibody (approximately 60%) were purified by fluorescence-activated cell sorting (FACS) and clones isolated following culture in semi-solid media as previously (Zannettino et al., 1996). To recover proviral cDNA inserts corresponding to the STRO-3 antigen, the polymerase chain reaction (PCR) using retroviral specific primers was performed on genomic DNA prepared from three STRO-3-expressing BAF-3 clones, as previously described (Zannettino et al., 1996).

Partial-Sequencing of PCR-rescued cDNA clones and Computer Analysis:

As described previously (Zannettino et al., 1996), cDNA clones generated by PCR were gel purified and subcloned into the pGEM-T vector (Promega, Madison, WI) as recommended by the manufacturer. Double-stranded DNA was prepared by standard alkaline lysis "mini-prep" method (Qiagen miniprep Kit) and 1-2 pg was used per sequencing reaction. Reactions were prepared using the PRISM™ Ready Reaction Cycle sequencing kit (Applied Biosystem, Foster City, CA), as recommended by the manufacturer. Reactions analysing both cDNA strands were run on a Applied Biosystems 373 automated sequence analyser and 500-600 bp of 5' and 3' sequence data was routinely obtained per clone. Sequence data were then analysed by accessing the Genbank and European Molecular Biology laboratory (EMBL) data bases at the National Centre for Biotechnological Information (NCBI).

Recloning of the STRO-3 Antigen cDNA Clone into pRVFneo and Validation of Surface Antigen Expression Following PCR recovery of proviral cDNA inserts from genomic DNA, unique Barn HI and Xho I restriction sites present in the 5' and 3' flanking regions respectively, were utilised to "redone" the cDNA into the MCS of the retroviral vector pRUFneo. E. coli DHlOB cells were transformed and plasmid DNA isolated using Qiagen-tip 100 columns (Qiagen, Victoria, Australia) as recommended by the manufacturer. Stable, G418 resistant ψ2 virus-producing cell lines were produced by calcium phosphate transfection and used to infect BAF-3 cells by co-cultivation, as described previously (Zannettino et al., 1996), G418 resistant FDC-Pl cells were then analysed for antigen expression by indirect immunofluorescence and flow cytometry.

Reverse Transcriptase Polymerase Chain Reaction (RT-PCS) Analysis.

Total cellular RNA was prepared from clones of STRO-3 antigen BAP-3 cells using RNAzolB extraction method (Biotecx Lab. Inc., Houston, TX), according to the manufacturer's recommendations. RNA isolated from each subpopulation was then used as a template for cDNA synthesis, prepared using a First-strand cDNA synthesis kit (Pharmacia Biotech, Uppsala, Sweden). The expression of bone and Liver/kidney isoform of ALP transcripts was assessed by PCR amplification, using a standard protocol as described previously (Groathos et al, 1999). The alkaline phosphatase primer sets used in this study have been previously described (Sato et al., 1994). Following amplification, each reaction mixture was analysed by 1.5% agarose gel electrophoresis, and visualised by ethidiuni bromide staining. RNA integrity was assessed by the expression of GAPDH (Gronthos et a, 1999), Results and Discussion Using a retroviral expression library strategy pioneered in our laboratory, we subsequently identified the gene encoding for the protein identified by the STRO-3 mAb (Zannettino et al., 1996). Briefly, the murine cell line BAF-3, was infected with retroviral particles constructed from a library of cDNAs derived from cultured human MPC. BAF-3 clones reactive with STRO-3 were isolated by immunomagnetic bead selection using sheep anti-mouse IgG magnetic beads.

Figure 1:
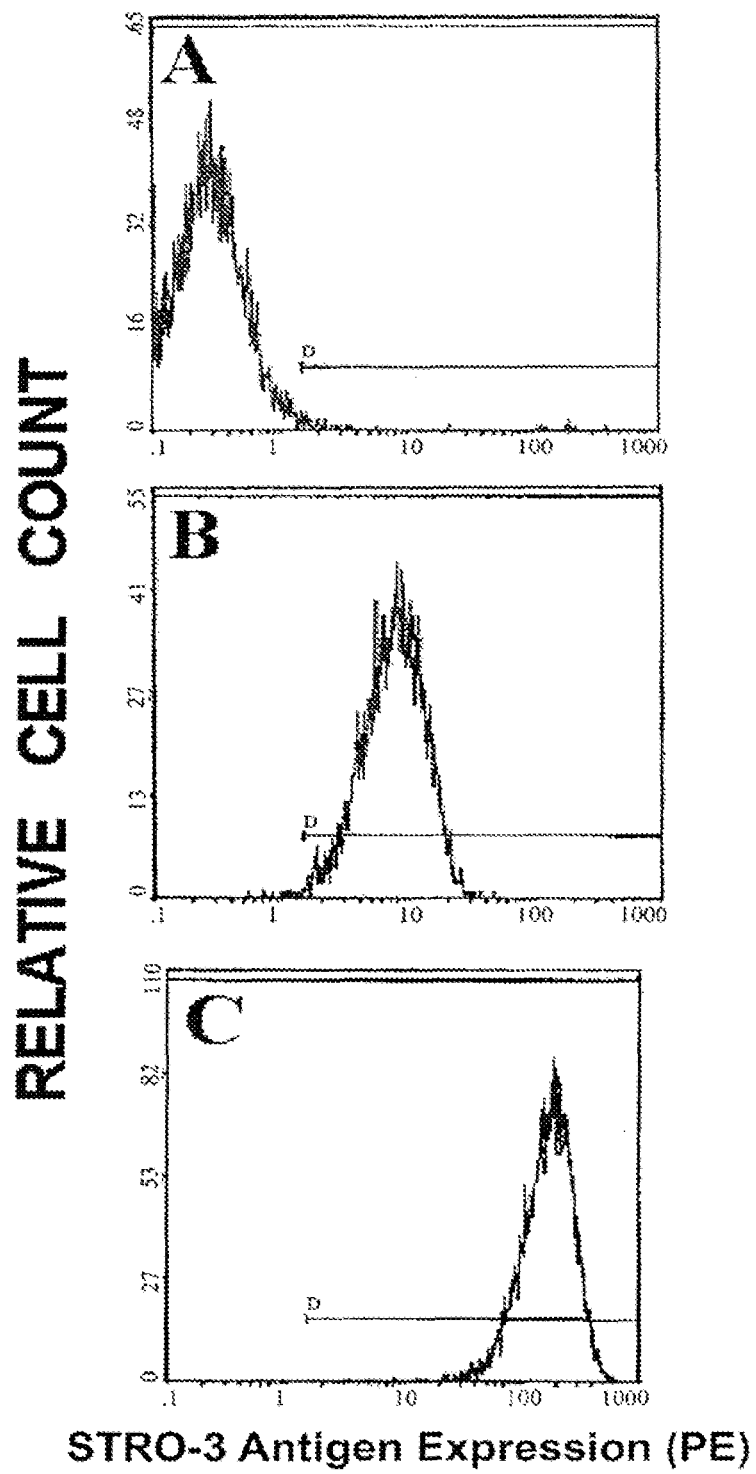
FIG. 1 Flow Cytometric Analysis of STRO-3-Selected BAF-3 Cells Progressive enrichment of BAF-3 expressing the STRO-3 surface Ag. BAF-3 cells selectively isolated by the magnetic bead/mAb capture and enrichment procedure were immunolabeled with the STRO-3 mAb and analyzed by flow cytometry after one (A), two (B), and three (C) rounds of selection. Magnetic bead selection and enrichment were carried out until homogeneity of Ag expression was achieved.

As shown in FIG. 1, flow cytometric analysis of cells which were recovered following several rounds of bead selection were found to express the STRO-3 antigen at appreciable levels. Clones of STRO-3-expressing BAF-3 cells were subsequently prepared by seeding the pool of immunomagnetic bead-selected cells at low density into semi-solid methylcellulose, as described in the methods. A randomised selection of BAF-3 colonies were then isolated and expanded in liquid culture supplemented with murine IL-3 and G418—Selected clones demonstrating a high reactivity with STRO-3 were then expanded in culture, and genomic DNA prepared as described in the methods. The cDNA inserts were subsequently rescued from the provims by long-range PCR amplification as previously described (Zannettino et al., 1996).

Figure 2:
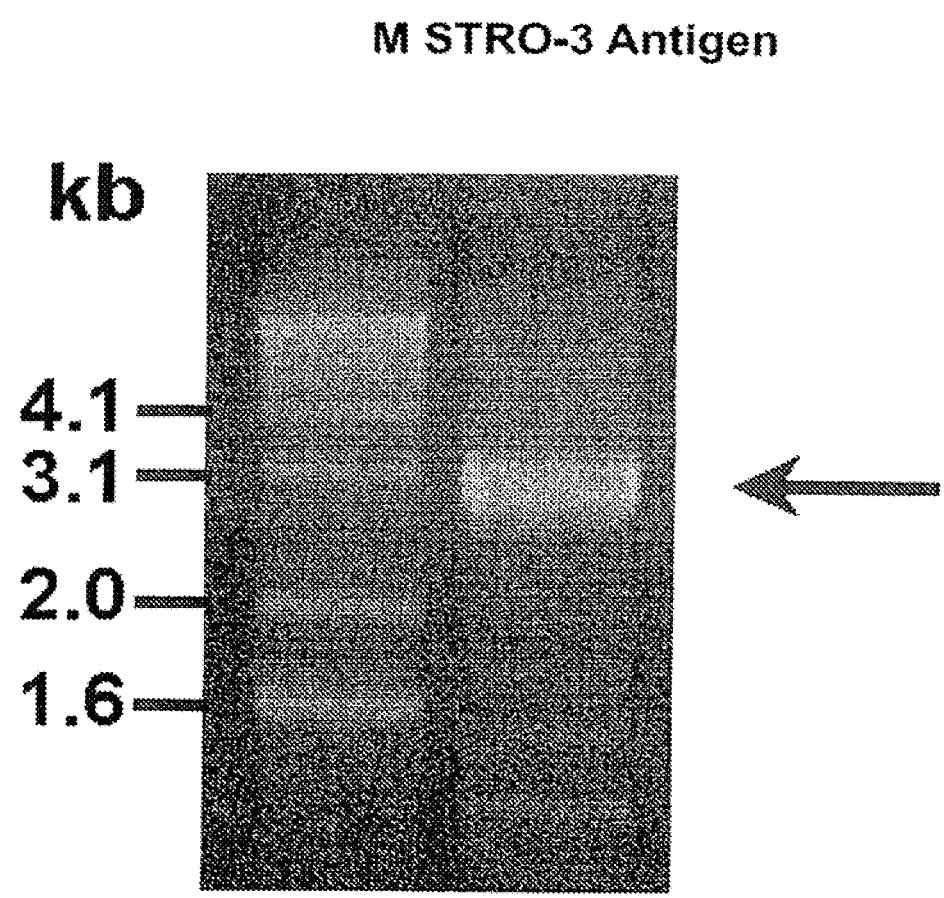
FIG. 2. PCR recovery of proviral cDNA inserts from genomic DNA isolated from BAF-3 cells expressing STRO-3 surface Ag Long range PCR was used to recover the cDNA inserts from genomic DNA (arrow) isolated from the BAF-3 cells expressing the STRO-3 cell surface Ag. The PGR primers used were complementary to the sequences adjacent to the multi-do πing site in the retroviral vector. Amplification was performed as detailed in Methods, after which the PCR products were separated on a 1.0% agarose gel and visualised by ethidium bromide staining.

PCR amplification of a representative clone for STRO-3 is shown in FIG. 2. Following agarose gel electrophoresis and ethidium bromide staining, the corresponding PCR products from three different clones were gel-pureed using a QIAquick Gel Extraction Kit (QIAGEN Inc. Chatsworth, CA, USA) and cloned in the pCxEM-T vector as recommended by the manufacturer. The nucleotide sequence of the PCR products was derived by sequencing with the PRISM™ Ready Reaction DyeDeoxy™ Terminator Cycle Sequencing Kit (Applied Biosystems Inc., Foster City, California, USA)

according to the manufacturer's specifications. Reactions were run on a Applied Biosystems 373 automated sequence analyser, and several hundred base pairs of nucleic acid sequence data was obtained for each clone. The resulting partial-nucleotide sequences were compared with the entries submitted to the Genbank/EMBL databases via standard FASTA alignment analysis. Partial DNA sequences for both antigens are given (FIG. 3). Comparisons with sequences in the combined EMBL/Genbank database identified the STRO-3 antigen as corresponding to the bone/liver/kidney form of alkaline phosphatase, namely TNAP.

Figure 4:
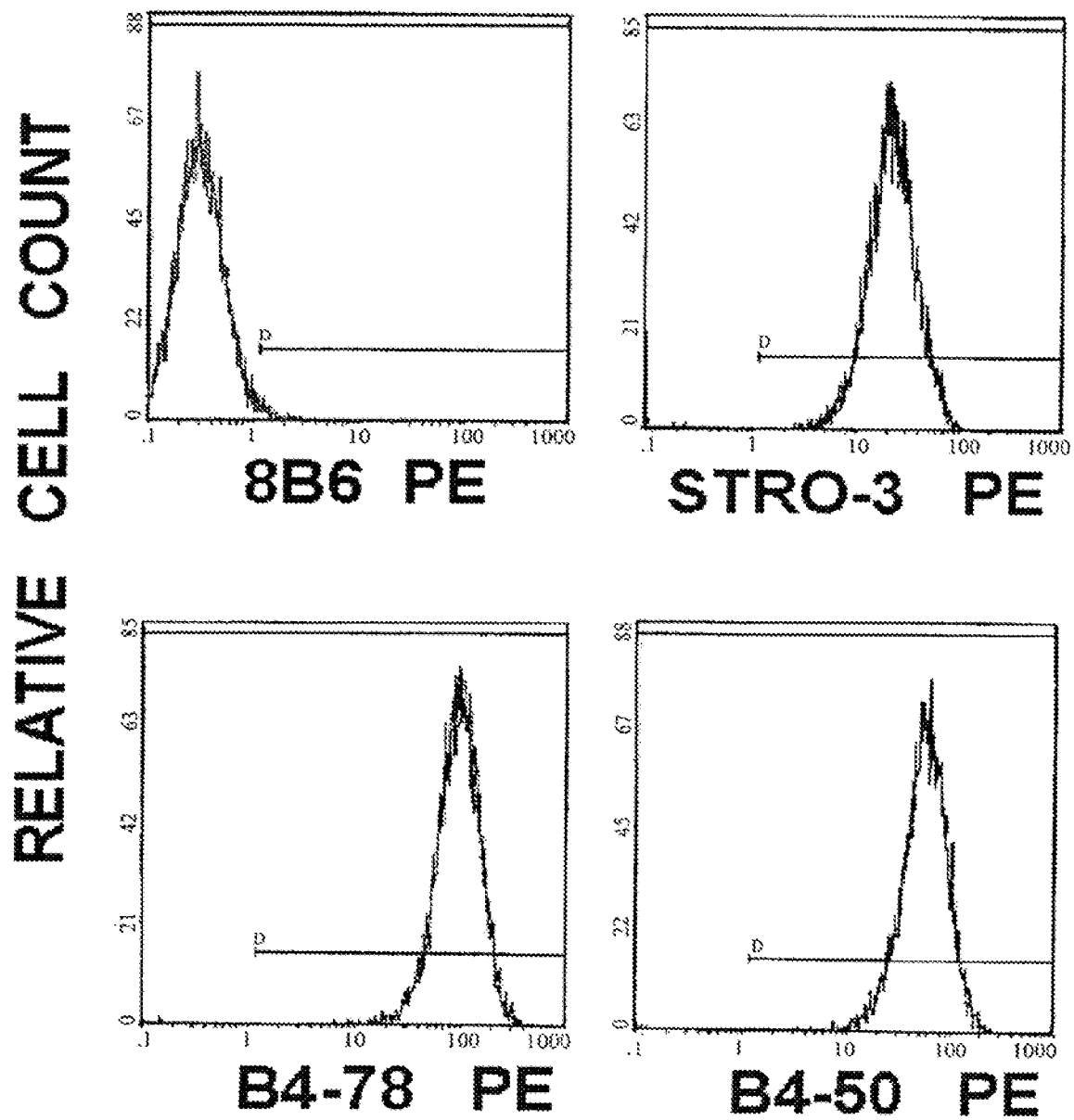
FIG. 4. STRO-3 mAb recognise the BLK isoform of ALP in BAF-3 Transfectants A 1.7 kb βamH-holI restriction fragment of the BLK-ALP cDNA (harbouring both the entire coding sequence and the 5' and 3' non-coding regions) was subcloned into the pR_F. αeO vector and subsequently introduced into BAF-3 cells by retroviral transduction (refer to Materials and Methods). The resultant G418-resistant cell population, was stained by indirect immunofluorescence and analysed by flow cytometry. Data are displayed as single-parameter fluorescence (FITC) hisiograms of $1 \times 10^4$ light-scatter gated events, collected as list mode data IgG1 control (thin black line); (A) mAb STRO-3; (B) mAb B4-78; (C) mAb B4-50 and (d) mAb 8B6.

Independent confirmation of the specificity of the STRO-3 mAb was subsequently obtained following immunofluorescence and flow cytometric analysis of TNAP expressing BAF-3 clones with the alkaline phosphatase specific antibodies, 134-78, 50 (Developmental Studies Hybridoma Bank, University of Iowa) which recognises an epitope conserved between each of the bone, liver and kidney isoforms of ALP (FIG. 4).

Figure 5:
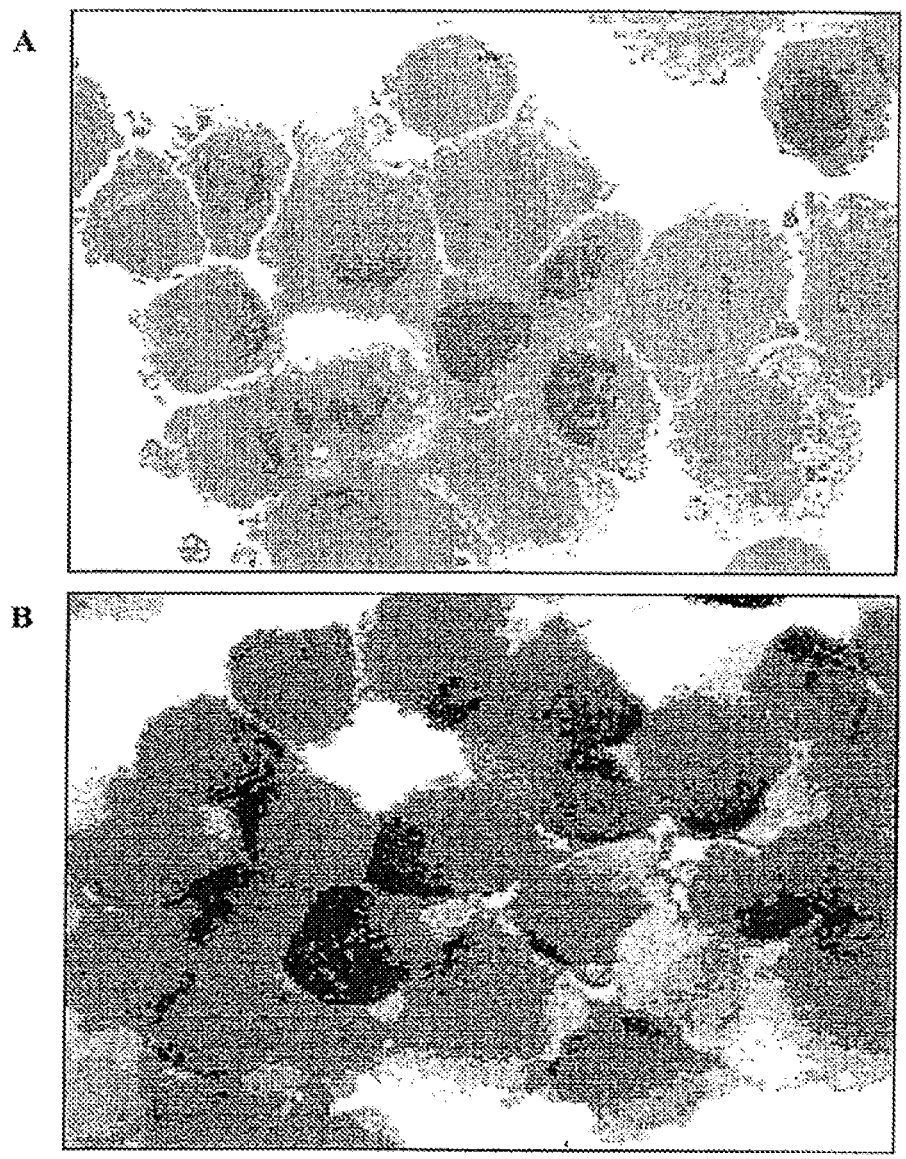
FIG. 5. STRO-3 mAb Identifies an Enzymatically Active Form of ALP Cytospia preparations of untransfected (A) and STRO-3 positive (B) BAF-3 cells were prepared on glass slides then fixed with 70% ethanol. The slides were then incubated with alkaline phosphatase substrate using the Sigma Alkaline Phosphatase Substrate Kit (AMOIOO) as recommended by the manufacturer. The results showed that BAF-3 cells expressing STRO-3 (B) contained the active form of alkaline phosphatase enzyme (purple/red colour). The cells were counter stained with Haematoxylin (blue).
Figure 6:
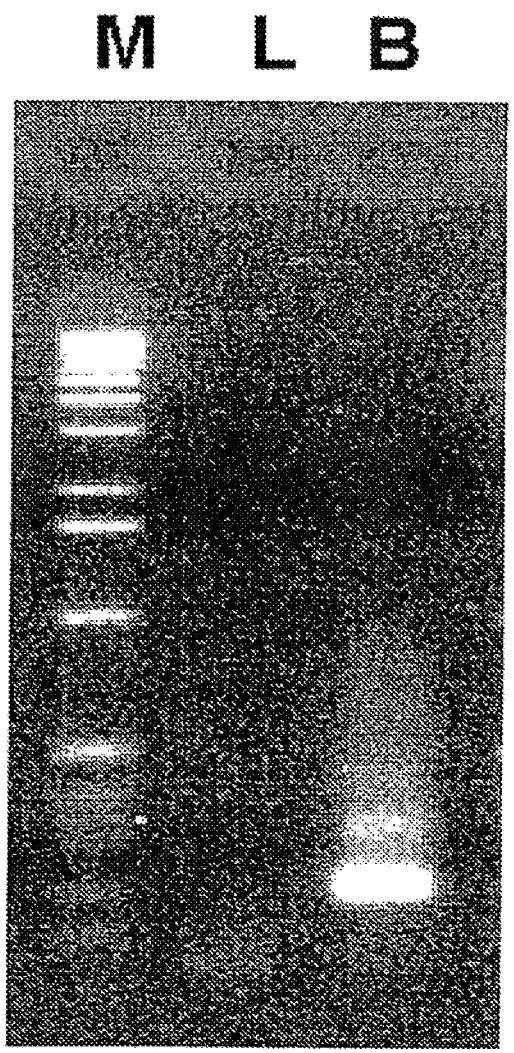
FIG. 6. ALP specific PCR

In addition, the mAb 134-50 (Developmental Studies Hybridoma Bank, University of Iowa) which has been previously shown to be specific for the bone AP enzyme also displayed immunoreactivity with the TNAP transfectants. In contrast, no detectable reactivity was observed following the staining of the TNAP transfectants with mAb 8B6 ((DAKO), which identifies an epitope present on only human placental AP antigen. In addition, BAF-3 cells re-transfected with the TNAP-BAF-3 cDNA insert, were found to express an active form of alkaline phosphatase, as demonstrated by positive reactivity in the presence of alkaline phosphatase substrate (FIG. 5). PCR analysis using specific primers for the bone and liver forms of alkaline phosphatase (Sato et al., 1994) identified the transcripts as bone-specific (FIG. 6).

Example 3: Immunohistochemical Detection of TNAP by STRO-3 mAb in Sections of BM Trephine Materials and Methods Five micron sections of paraffin-embedded normal post-natal bone, were cut onto 3-aminopropyl-triethoxysilane-coated slides and endogenous peroxidase activity blocked by incubation with 3% $H_2O_2$/Methanol. Microwave antigen retrieval was then performed in the presence of 1 mM.EDTA, pH 8.0 buffer. The slides were allowed to cool to 40° C. and non-specific binding blocked by incubating sections with 3% noπrial horse serum for 1 hour at RT, The slides were then incubated overnight with either an isotype-matched, non-binding control mAb (1B5, IgGi) or STRO-3 mAb. Bound antibody was revealed using a three-step immunoperoxidase method (Gronthos et al., 2000; Gronthos et al., 2003) in which slides were sequentially incubated with (a) affinity-purified HRP-conjugated goat anti-mouse antibody (Dako, Botany, NSW, Australia), followed by (b) affinity-purified Horseradish peroxidase (HRP)-conjugated swine anti-goat immunoglobulin (Tago, Burlingame. CA USA) and (c) hydrogen peroxide as substrate and amino ethylcarbazoie (AEC, Sigma, St Louis, MO) as the dye. Slides were counterstained briefly with haematoxylin solution and mounted in Guir Aquamount (BDH, Poole, UK).

Results and Discussion

The immunoreactivity of STRO-3 nxAb was assessed in sections of developing bone marrow derived from 55 day old human limb. No staining was observed in the periosteum or in cartilage (FIG. 7). However there was a marked expression of TNAP in the mesenchymal cells of the bone marrow spaces perivascular regions and at the interface of the growth plate region.

Example 4: Isolation of Human Bone Marrow Cells Using STRO-3 mAb

Bone marrow (BM) is harvested from healthy normal adult volunteers (20-35 years old), in accordance with procedures approved by the Institutional Ethics Committee of the Royal Adelaide Hospital. Briefly, 40 ml of BM is aspirated from the posterior iliac crest into lithium-heparin anticoagdantaonlaining tubes. BMMNC are prepared by density gradient separation using Lymphoprep™ (Nycomed Pharma, Oslo, Norway) as previously described (Zannettico et al, 199S). Following centrifugation at 400×g for 30 minutes at 4° C., the buffy layer is removed with a transfer pipette and washed three times in "HHF", composed of Hank's balanced salt solution (HBSS; Life Technologies, Gaithersburg, MD), containing 5% fetal calf serum (FCS, CSL Limited, Victoria, Australia).

TNAP+ were subsequently isolated by magnetic activated cell sorting as previously described (Gronthos et al., 2003; Gronthos et al, 1995). Briefly, approximately 1-3×$10^8$ BMMNC are incubated in blocking buffer, consisting of 10% (v/v) normal rabbit serum in HHF for 20 minutes on ice. The cells axe incubated with 200 µl of a 10 µg/ml solution of STR-3 mAb in blocking buffer for 1 hour on ice. The cells are subsequently washed twice in HHF by centrifugation at 400×g. A 1/50 dilution of goat anti-mouse γ-biolin (Southern Biotechnology Associates, Birmingham, UK.) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred µl streptavidin microbeads (Miltenyi Biotec; Bergisch Gladbach, Germany) are added to the cell suspension and incubated on ice for 15 minutes. The cell suspension is washed twice and resuspended in 0-5 ml of MACS buffer and subsequently loaded onto a mini. MACS column (MS Columns, Miltenyi Biotec), and washed three times with 0.5 ml MACS buffer to retrieve the cells which did not bind the STRO-3 mAb. After addition of a further 1 ml MACS buffer, the column is removed from the magnet and the TNAP-positive cells are isolated by positive pressure. An aliquot of cells from each fraction can be stained with streptavidin-FITC and the purity assessed by flow cytometry. STRO-3 mAb was found to identify a minor subpopulation of BMMNCs (<1%).

Primary cultures are established from the MACS isolated TNAP+ cells by plating in α-MEM supplemented with 20% fetal calf serum, 2 mM L-glutamine and 100 µm L-ascorbate-2-phosphate as previously described (Gronthos et al., 1995).

Example 5: Human Bone Marrow Cells Selected by STRO-3 mAb Give Rise to CFU-F

Materials and Methods
Magnetic-Activated Cell Sorting (MAGS)

To evaluate the CFU-F outgrowth potential OfTNAP++ cells, MACS sorting was used to separate TNAP+ and TNAP− cells from the bone marrow. This was performed generally as previously described (Gronthos and Simmons, 1995; Gronthos et al., 2003) but using the STRO-3 mAb. In brief, approximately 1-3×$10^8$ normal human bone marrow mononuclear cells were incubated with STRO-3 supernatant, anti-IgG-biotii-, streptavidin microbeads and finally streptavidin FITC (Caltag Laboratories, Burlingame, CA) before being separated on a Mini MACS magnetic column (Miltenyi Biotec Inc., Auburn, CA) according to the manufacturers instructions.

Fluorescence-Activated Cell Sorting (FACS)

CFU-F outgrowth capacity was also examined on STRO-3 selected cells sorted on the basis of +ve or –ve expression of STRO-1.

This was performed as previously described (Gronthos and Simmons, 1995; Gronthos et al., 2003). In brief, approximately $1-3 \times 10^8$ normal human bone marrow mononuclear cells were sequentially incubated with STRO-1 supernatant, anti-IgM-biotin, streptavidin microbeads and finally streptavidin FITC (Caltag Laboratories, Burlingame, CA) before being separated on a Mini MACS magnetic column. (Miltenyi Biotec Inc, Auburn, CA) according to the manufacturers instructions.

The STRO-1+ MACS isolated cells were labelled with streptavidin conjugated FITC then incubated either purified STRO-3 mAb or isotype control 185 (10 µg/ml) for 30 minutes on ice, washed and incubated with phycoerythrin (PE) conjugated goat anti-mouse IgG antibody (¹⁄₅₀; Southern Biotechnology Associates, Birmingham, AL) for an additional 20 minutes on ice. Cells were sorted using a FACStar$^{PLUS}$ flow cytometer (Becton Dickinson, Sunnyvale, CA). The STRO-1$^{bri}$/STRO-3$^+$ or STRO-1$^{bri}$/STRO-3" cells were cultured in alpha-Modification of Eagle's Medium supplemented with 20% fetal calf serum, L-glutamine 2 mM, ascorbate-2-phosphate (100 µM) to initiate primary culture in 5% CO, at 37° C. humidified atmosphere.

Results and Discussion

Experiments were designed to examine the potential of using STRO-3 mAb as a single reagent for isolating cells for CFU-F outgrowth (FIG. 8), MACS isolation based on TNAP expression revealed that clonogenic CFU-F were only detected in the TNAP+ BMMNC fraction.

Given that STRO-3 (IgGi) is a different isotype to that of STRO-1 (IgM) the ability of STRO-3 to identify clonogenic CFU-F was assessed by two-colour FACS analysis based on its co-expression with STRO-1$^+$ cells isolated using the MACS procedure (FIG. 9). STRO-3 mAb demonstrated a unique binding pattern, reacting with a subset of the STRO-1$^+$ BMMNC fraction which expressed the STRO-1 antigen at high levels (STRO-1$^{bright}$ fraction), effectively isolating and enriching for the MPC population (Table 2). Furthermore, the mAb STRO-3 failed to react with CD34 positive haemopoïetic stem cells in human adult bone marrow aspirates (data not shown).

TABLE 2

Enrichment of human bone marrow cells by dual-colour FACS analysis based on the co-expression of the cell surface markers STRO-I and TNAP (refer to FIG. 9). FACS sorted cells were cultured under standard clonogenip conditions in alpha MEM supplemented with 20% FCS. The data represents the mean number of day 14 colony-forming cells (CFU-F) per $10^5$ cells plated ± SE (n = 3 different bone marrow aspirates). These data suggest that human MPC are exclusively restricted to the TNAP positive fraction of BM which co-express the STRO-I antigen brightly.

| Bone Marrow Fraction | Frequency of CFU-F/$10^5$ Cells | Enrichment (Fold Increase) |
|---|---|---|
| Unfractionated BMMNC | 11.0 ± 2.2 | 1.0 |
| TNAP+/STRO-1$^{bright}$ | 4.511 ± 185 | 410 |
| TNAP+/STRO-1$^{dull/int}$ | 0.0 | 0.0 |

Example 6: Phenotype of STHO-3 mAb Selected Cells Before and after Culture Expansion Materials and Methods Single color flow cytometry was performed essentially as described in Gronthos et al. (1999), Briefly, cultures of cells at each passage were liberated by trypsin/EDTA and subsequently incubated for 30 min on ice in blocking buffer. Approximately $1 \times 10^5$ cells were washed as described above, and resuspended in 200 µl of primary antibody or antibodies for 1 hr on ice. The primary antibody consisting of saturating concentrations of the mouse IgM monoclonal antibody STRO-1 and/or a mouse IgG monoclonal antibody to human CC9 and STRO-3 were used. Other antibodies used included mAbs that bind CD45, CD34 and 3G5.

The mouse isotype IgM and IgG negative control mAbs were treated under identical conditions. After the cells were gashed, second label(s) were added in a final volume of 100 µl consisting of goat anti-mouse IgM µ-chain specific-FITC (¹⁄₅₀ dilution) and either goat anti-mouse IgG γ-specific-PE (¹⁄₅₀ dilution) or anti-rabbit Ig-specific-PE (¹⁄₅₀ dilution.) (Southern Biotechnology Associates). The cells were incubated for 45 min on ice, washed twice and fixed in FACs FIX (PBS supplemented with 1% (v/v), 2% (w/v) D-glucose, 0.01% sodium azide). The cells were then analysed on an Epics®-XL-MCL flow cytometer (Beckman Coulter, Hialeah, FL). The dot plot histogram represents $5 \times 10^4$ events collected as listmode data.

Results and Discussion

As can be seen in FIG. 10, immunoselection of human bone marrow mononuclear cells using a magnetically labelled STRO-3 mAbb results hi isolation of a population of cells characterised by high levels of TNAP and CD45 surface antigen expression (FIG. 10), with approximately 90% of the TNAP+ cells co-expressing CD45. In contrast, less than 1% of the TNAP+ enriched cells isolated using the STRO3 mAb expressed the hematopoietic stem cell marker CD34. In addition, no more than 5% of the TNAP+ cells enriched using methods of the invention co-expressed any of the markers previously used to isolate MPC, including STRO-1, CC9/CD146, and 3G5.

Figure 11:
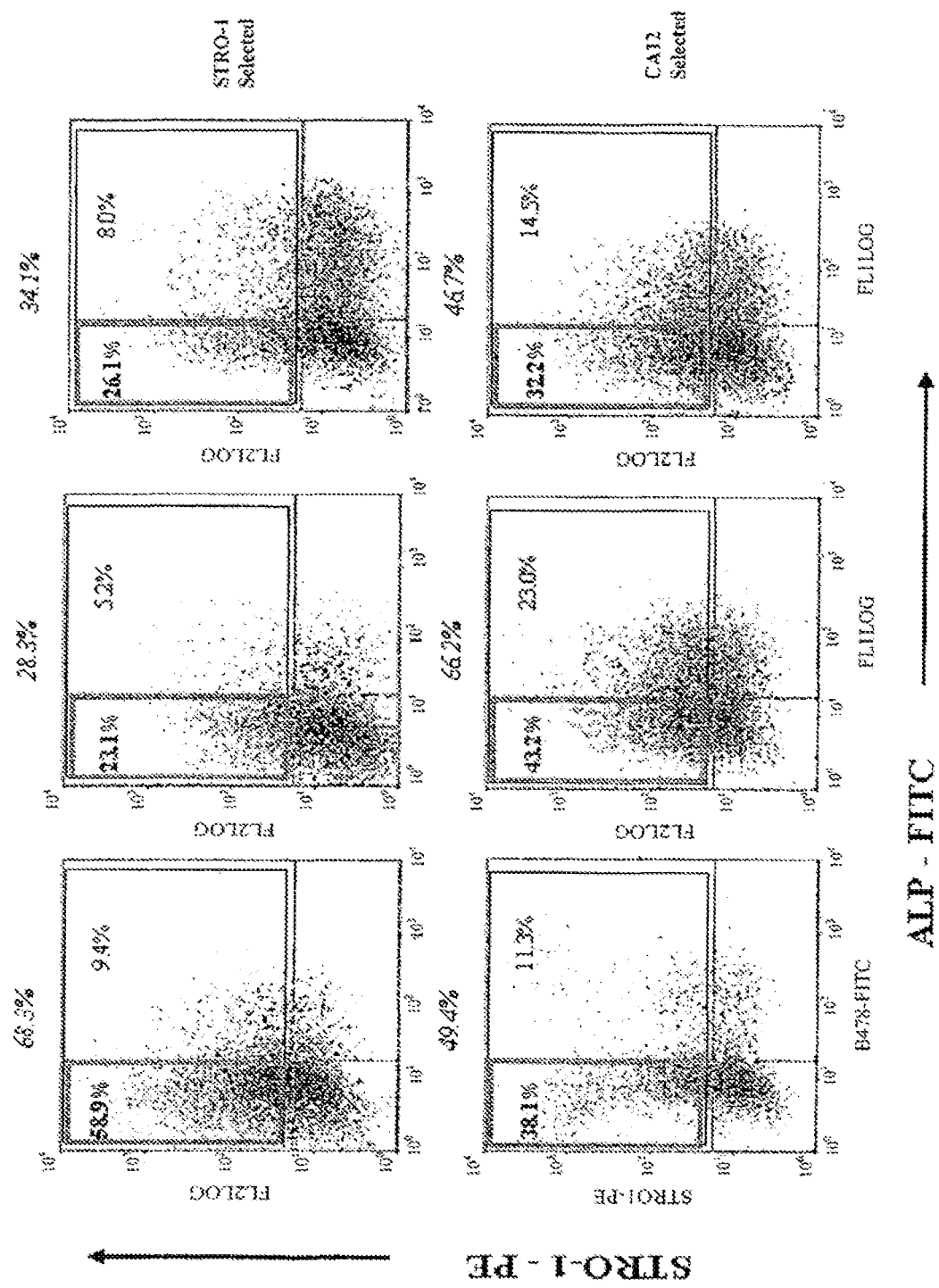

Following culture-expansion, the TNAP+ cells enriched using methods of the invention demonstrated a stable phenotype that differed from the enriched and freshly-isolated cells, FIG. 11. Culture expanded STRO-3 selected cells at both early (passage 2) and late (passage 5) passages were found to express homogeneously high levels of CC9/CD146 and HLA class I molecules, but were uniformly negative for CD45, HLA class II, CD 14, CD19, CD3, CDlla-c, CD31, CD86 and CDSO. Strikingly, while TNAP surface expression as detected by STRO-3 mAb was uniformly positive in early culture passages (passage 2), this was negative at later culture passages (passage 5).

Figure 13:
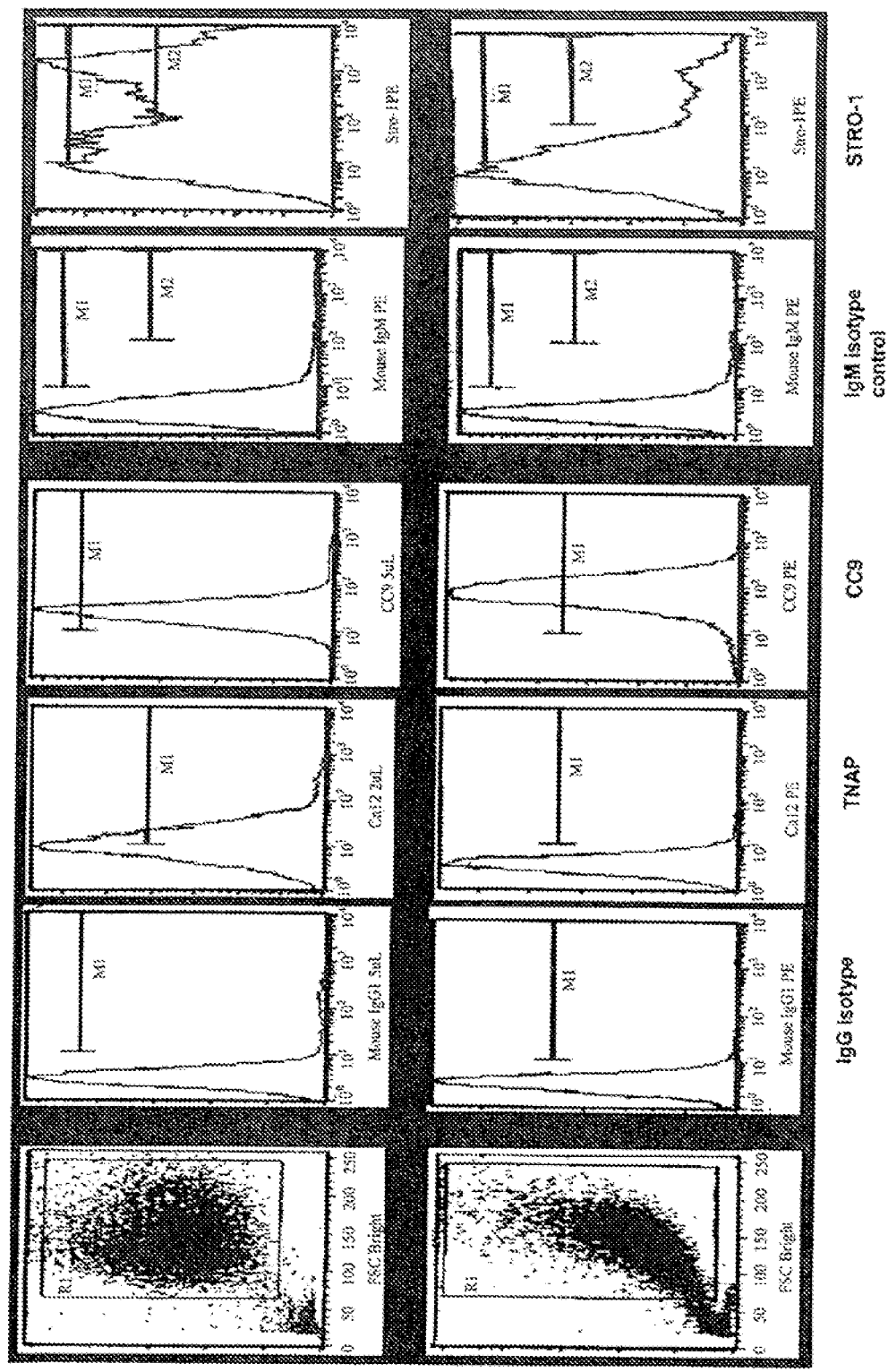

In contrast to progressive loss of STRO-3 reactivity following culture expansion, these TNAP+ cells enriched by STRO-3 selection demonstrated progressive increase in surface expression of the STRO-t antigen, FIGS. 11 and 13. By passage 2 approximately 84% of the cells were STRO-1 positive in comparison to the IgM isotype control, and approximately half (52%) expressed STRO-1 brightly (as defined by a 2 log magnitude higher expression of STRO-1 surface expression than STRO-1 negative cells). By passage 5, while most of the cells remained STRO-1 positive (approx. 69%), a lower proportion of cells expressed STRO-1 brightly (approx. 21%). This indicates mat initial culture of STRO-3 selected TNAP+ cells results in upregulation of the STRO-1 antigen, presumably reflecting proliferation without spontaneous differentiation, while ongoing culture results in downπregulation of STRO-1 antigen density from bright to intermediate expression.

Figure 12:
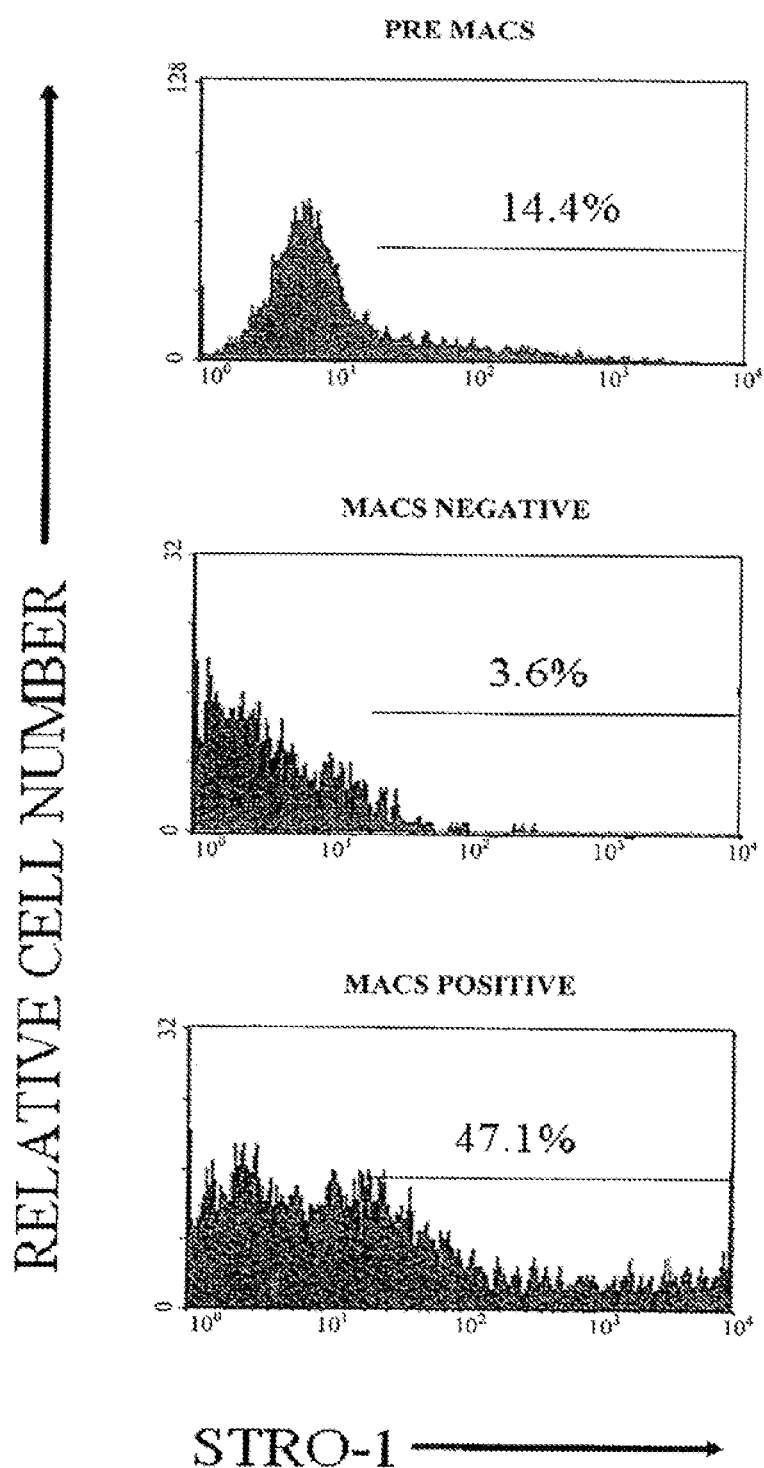

In marked contrast, immunoselectioα of human bone marrow mononuclear cells using a magnetically labelled STRO-1 mAb results in isolation of a population of cells characterised by high (approximately 50%) STRO-1 expression, and absence of CD45 expression (FIG. 12, and WO/2004/085630). Despite this high-level of initial STRO-1 expression, culture expansion of STRO-1 selected cells results in a progressive decrease in STRO-1 expression by passages 4 to 6. These reduced STRO-1 levels following culture-expansion are significantly reduced relative to both the starting population, and the culture-expanded TNAP+ enriched cells by STRO-3 selection at the same passages 4 to 6 (Figure H).

Together, these results show that the TNAP+ enriched population by STRO-3 selection is distinct from the STRO-1+ enriched population in terms of phenotypic characteristics both when initially freshly isolated and following culture-expansion.

Example 7: Differentiation of TNAP+ Cells—Adipogenesis

Materials and Methods
Adipogenic Assay Procedure
Preparation of Adipogenic Induction Medium: Adipogenic Induction Medium should be used once the cells have become 100% confluent (approximately 5-13 days). Prepare the medium before the cells become confluent.
1: Decontaminate the external surfaces of the Adipogenic Induction Medium (PT-3102B) and the following SingleQuots© with 70% v/v ethanol or isopropaπol:
  a. h-Insulin (recombinant)
  b. L-Glutamine
  c. MCGS
  d. Dwcamethasone
  e. Indomethacin
  f. IBMX (34sobuty-1-methyl-x.tn.thme)
  g. Pen/Steep
2: Aseptically open the above SingİeQuots and add the contents to the 175 ml of Adipogenic Induction Medium.
3. Rinse each. SingleQuot vial with the medium,
4. Use supplemented medium for the adipogenic induction of cells only. Store at 2° C. to 8° C. in the dark until needed.
5 Prepare Adipogenic Maintenance Medium as follows:
  1. Decontaminate the external surfaces of the Adipogenic Maintenance Medium (PT-3102A) and the following SingleQuots with 70% v/v ethanol or isopropanol:
    a. h-Insulin (recombinant)
    b. L-Glutamine
    c. MCGS
    d. Pen/Strep
  2. Aseptically open the above SingleQuots and add the contents to the 175 ml of Adipogenic Maintenance Medium.
  3. Rinse each SingleQuot vial with the medium.
  4. Store supplemented Adipogenic Maintenance Medium at 2° C. to 8° C. in the dark until needed.
Adipogenesis Culture Protocol:
1. Plate $2.1\times10^4$ STRO-3 mAb selected cells per $cm^2$ of tissue culture surface area in 0.2 to 0.3 ml of MSCGM per $cm^2$ of tissue culture surface area. For example: $2\times10^5$ cells in 2 rol medium per 9.6 $cm^2$ well of a 6 well plate. Incubate the cells at 37° C., in a humidified atmosphere of 5% CO2.
2. Feed the cells every 2-3 days by completely replacing the medium with fresh MSCGM until the cultures reach confluence (5-13 days). The cells must be confluent, or post confluent, for optimal Adipogenic differentiation.
3. At 100% confluence, three cycles of induction/maintenance will stimulate optimal Adipogenic differentiation. Each cycle consists of feeding the cells with supplemented Adipogenesis Induction Medium and culture for 3 days (37° C., 5% $CO_2$) followed by 1-3 days of culture in supplemented Adipogenic Maintenance Medium. Feed non-induced control cells with only supplemented Adipogenic Maintenance Medium on the same schedule. Adipogenic cells are delicate and care should be used to avoid disrupting the numerous lipid vacuoles in the cells. Do not let the cells dry out when changing medium.
4. After 3 complete cycles of induction/maintenance, culture the cells for 7 more days in supplemented Adipogenic Maintenance Medium, replacing the medium every 2-3 days.
5. The extent of Adipogenic differentiation may be noted by microscopic observation of lipid vacuoles in the induced cells. To document the Adipogenic differentiation, cultures may be stained with AdipoRed. Non-induced cells will have few, if any, lipid vacuoles.
6. Cultures of unfixed cells may be used for assays requiring adipocytes.

AdipoRed™ Assay for in vitro Adipogenesis
Protocol for 6-, 12-, 24- and 48-well plates:
1. Seed cells at 30,000/$cm^2$ and culture and differentiate the cells as described above, using appropriate volumes of cell culture media.
2. Immediately prior to the assay, rinse each plate with PBS, and add AdipoRed, using the volumes in Table 3.

TABLE 3

Volumes for AdipoRed ™ assay.

|  | Rinse volume/well | Final volume of PBS/well | Volume of AdipoRed/well |
| --- | --- | --- | --- |
| 6-well plate | 2 ml | 5 ml | 140 μl |
| 12-well plate | 1 ml | 2 ml | 60 μl |
| 24-well plate | 1 ml | 1 ml | 30 μl |
| 48-well plate | 0.4 ml | 0.4 ml | 12 μl |
| 96-well plate | 0.2 ml | 0.2 ml | 5 μl |

3. After addition of the AdipoRed, the best mixing of the reagent is obtained by pipetting 50% of the contents of each well up and down two times (three times for 6-well plates). It is important to obtain a homogeneous dispersion of the blue AdipoRed reagent Be very careful not to touch the tip of the pipette to the cell monolayer or remove cells from the well surface.
4. After 10 minutes, place the plate in the fluorimeter and measure the fluorescence with excitation at 485 run and emission at 572 nm. If the fluorimeter does not have the appropriate filters, the settings used for the common fluorophore fluorescein (excitation 485 ran; emission. 535) can be used.

Results and Discussion

Two lots of cells were assayed for differentiative capacity. The amps of cells were labeled:

| 2242A | 2070C |
|---|---|
| P.2o | P.2o |
| ~30E6 cells | ~3QE6 cells |
| 102NOV2005 | 08NOV2005 |

The results are provided in FIG. 14 and show that cells selected with STRO 3 mAb are capable of differentiating into adipocytes.

Example 5: Differentiation of TNAP+ Cells—Osteogenesis

Materials and Methods
Osteogenic Assay Procedure
Prepare Osteogenic Induction Medium as follows:
1. Decontaminate the external surfaces of the Differentiation Basal Medium Osteogenic and the following SingleQuots with 70% v/v ethanol or isopropanol:
   a. Dexamethasone
   b. L-Glutamine
   c. Ascorbate
   d. Pen/Strep
   e. MCGS
   f. β-Glycerophosphate
2. Aseptically open the above SingleQuots and add the contents to the 185 ml of Differentiation Basal Medium— Osteogenic.
3. Rinse each SingleQuot vial with the medium.
4. Store the supplemented Osteogenic Differentiation Medium at 2° C. to 8° C. in the dark until needed.

Osteogenesis Culture Protocol:
1. Plate $3.1 \times 10^3$ STRO-3 mAb selected cells per $cm^2$ of tissue culture surface area in 0.2-0.3 ml of MSCGM per $cm^2$ tissue culture area. For example: $3 \times 10^4$ cells in 2 ml medium per 9.6 $cm^2$ well of a 6 well plate.
2. Allow the cells to adhere to foe culture surface for 4 to 24 hours in MSCGM at 37° C., in a humidified atmosphere of 5% $CO_2$.
3. Induce Osteogenesis by replacing the MSCGM with Osteogenesis Induction Medium.
4. Feed the induced cells every 3-4 days for 2-3 weeks by completely replacing the medium with fresh Osteogenesis Induction Medium. Feed non-induced control cells with MSCGM on the same schedule.
5. Osteogenic induced cells will show changes in cell morphology, from spindle shaped to cuboidal shaped, as they differentiate and mineralize. Gaps may form in the post confluent cell layer and cells may begin to delaminate from culture surface. If this de-lamination is observed, proceed immediately to analysis of osteogenic differentiation as indicated by calcium deposition, or use the induced cells for other assays requiring osteocytes.
6. For calcium deposition assays, harvest cells by rinsing them in calcium free PBS, then scraping cells from the culture surface in the presence of 0.5M HCl. Assay the extracts from osteogenic induced cultures for calcium content and compare to extracts from non-induced control cells.

Calcium Deposition Assay for In Vitro Osteogenesis
Materials:
DPBS, without calcium or magnesium—Cambrex catalog #17-516Q
0.5NHCl
Calcium (CPC) Liquicolor kit—Staobio Laboratory catalog #0150-250
induced Osteogenic cultures
Plate reader or spectrophotometer
Procedure:
Aspirate all culture medium from each well of a 6-well culture plate that contains induced or control cells to be tested.
Rinse the cells in the plate by adding 1 ml of PBS to the side of each well, being careful to not dislodge the cells.
Aspirate off the PBS and re-rinse, as above.
Aspirate the second wash and add 0.5 ml of Q.5N HCl to each well.
Scrape the cells off of the surface using a cell lifter and transfer the cells and HCl to a polypropylene tube (1.5 ml Eppendorf tube or any 2-5 ml polypropylene tube with a tight fitting cap).
Add an additional 0.5 ml of 0.5N HCl to each well to recover any cells remaining in the well, and transfer this to the appropriate tube.
Samples may be capped tightly and stored at −20° C. for one month if they are not to be tested immediately.
Extract the calcium from the cells by snaking the tubes on an orbital shaker for 3-24 hours at 4° C. If using frozen samples, allow extra time for samples to thaw.
Centrifuge the sample tubes at 500 g for 2 minutes.
Carefully collect the supernatant with extracted calcium, without disrupting the pellet, and transfer to a new tube.
Following the instructions provided in the Stanbio Laboratory Calcium (CPC) Liquicolor kit, prepare a standard curve with the calcium standard and deteπrcine the amount of calcium in each control and osteo-induced sample.
Sample and assay reagent volumes may be adjusted to fit microliter plates (200 μl) or spectrophotometer cuvettes (2 ml).
10 μl-100 μl of sample is used for each calcium determination. Unused sample extract may be re-frozen for future re-assay.

Results and Discussion
The results are provided in FIG. 15 and show that cells selected with STRO-3 mAb are capable of differentiating into osteocytes.

Example 9: Differentiation of TNAP++ Cells—Chondrogenesis, Adipogenesis and Osteogenesis Choπdrogenic differentiation was assessed in aggregate cultures treated with 10 ng/ml TGF-β3 as previously described (Gronfhos et al., 2003). Alcian Blue demonstrated that STRO-3 mAb selected cells are capable of producing proteoglycan (FIG. 16C), and thus chondrocytes.

STRO-3 mAb selected cells were also differentiated into functional osteoblasts, following 3 weeks culture in OMEM supplemented with 10% FCS, 100 μM L-ascorbate-2-phosphate, dexamethasone 10-7 M and 3 mM inorganic phosphate. Mineral deposits were identified by positive Alizarin Red staining (FIG. 16A).

Similarly, adipogenesis was induced in the presence of 0.5 mM met hlisobuty lmelhyl xanhe, 0.5 μM hydrocortisone, and 60 μM indomethacin as previously described (FIG. 16B). Oil Red O staining demonstrated the presence of lipid-laden fat cells.

Example 10: Transplantation of Expanded Human STRO-3 mAb Selected Cells Induce New Bone Formation In Vivo Approximately $5.0 \times 10^6$ ex vivo expanded cells derived from STRO-3 mAb selected bone marrow cells were mixed with 40 mg of hydroxyapatite/tricalcium phosphate (HA/TCP) ceramic powder (Zimmer Inc, Warsaw, IN) and then transplanted subcutaneously into the dorsal surface of 6-week-old immunocompromised NOD/SCID mice (ARC, Perth, WA 5 Australia) fox eight weeks as previously described ((Gronthos et al., 2003). These procedures were performed in accordance to specifications of an approved animal protocol (University of Adelaide Ethics Number M19/2005), Harvested implants were fixed in 4% paraformaldehyde, then decalcification with 10% EDTA solution before being embedding into paraffin. A representative cross section of a 8 week old transplant stained with H&E is shown. Histological examination demonstrated the presence of new bone formation (FIG. 16D).

Example 11: STRO-3 raAb Selected Cells are Used in Bone Repair

Materials and Methods
Tibia Critical Sized Defect

With the sheep in dorsal recumbency, the wool and hair was removed from above the left bind limb (mid femur) down to the foot The skin over the tibia was prepared for aseptic surgery using alternating scrubs of povidone-iodine (Betadine) and alcohol. The limb was draped for aseptic surgery. Peri operative antibiotic prophylaxis (Ancef; 1 μm preoperatively, 1 gm mid-surgery and 1 gm following wound closure, intravenously) began at this point. A 6-cm skin incision extending through the periosteum was made over the medial diaphysis of the tibia. The periosteum and overlying soft tissues was bluntly elevated circumferentially. A 5-cm segmental defect was created mid-diaphysis with two osteotomies using an oscillating saw under constant cooling with saline solution.

The defect was repaired using a locking intermedullary nail. For insertion of the nail, a longitudinal incision, just medial to the midline, was made over the left knee (stifle) joint with the knee in a flexed position. The joint capsule was split, the patellar tendon retracted laterally, aid the centre of the tibial plateau dissected free of adipose tissue within the joint. A 6-mm entry portal was created by a drill- and the diaphysis of the tibia reamed with hand reamers until the nail can be inserted press-fit If necessary, the distal tibial metaphysis was reamed with an 8-mm drill so the distal part of the nail could be inserted manually. The nail was inserted with the use of the insertion handle and the driving head connected to the proximal end of the nail. Proximal and distal interlocking was performed with proximal and distal aiming devices.

Administration of Culture Expanded STRO-3 mAb Selected CeUs and HA/TCP Carrier to Sheep Tibia Critical Sized Defeat The defect was packed with an HA/TCP carrier or HA/TCP+ STRO-3 mAb selected culture expanded cells and tested at varying concentrations depending on the treatment group (25M, 75M or 225M) following brief incubation in the OR setting. The soft tissues was then closed over the defect to ensure containment of the carrier and cells.

Animals had plain radiographs taken lateral and craniocaudal (AP) under general anaesthesia. Radiographs were taken at the following timepoints: Day O (surgery) and 1, 2, and 3 months.

Radiographs were interpreted according to the following criteria:

% callus bridge was the summed measure of the amount of mineralized tissue extended into the defect area both proximal and distal and divided it by the total defect length.

Fusion was characterized by a scoring system below:
0 (no fusion);
1 (moderate fusion);
2 (robust interconnected fusion mass).

Spine Fusion Procedure

Sheep were anesthetized and wool was removed from the dorsal lumbar region of the sheep and positioned in sternal recumbency on the operating table. The lumbar region was prepared for aseptic surgery with multiple scrubs of povidone-iodine alternated with isopropyl alcohol. The area was draped and local anesthesia (Lidocarae), was infiltrated along dorsal approach to L4 and L5 dorsal to the spinous processes.

Approach to the transverse processes: A 20 cm skin incision was made and the paraspinal muscles will be dissected off the spinous processes and laminae. Facet joints and transverse processes between. L3 and L4 will be exposed.

Instrumentation and Spine Fusion Technique: The transverse processes of L3 and L4 was decorticated bilaterally. The HA/CP graft substitute (carrier) or carrier + allogeneic cells or autograft was placed between the transverse processes. At this point in the surgery, the sheep undergo transpedicular screw fixation using screws and rods (Medtrome-Sofamor-Danek; CD-Horozon, M8 fixed screw head system). The surgical site was closed routinely.

After 4 months, all sheep were humanely euthanized and immediately after removal of the connecting rods, the explanted spines subjected to CT scans and plain radiographs and faxitron analysis.

Mechanical Testing of Spine

Immediately following euthanasia, intact lumbar spines were harvested and immediately prepared for mechanical testing, A four vertebrae construct consisting of the two affected (fused) vertebrae as well as an additional vertebral level above and below the level of the fusion was isolated from the lumbar spine. These isolated specimens were denuded of all peri-spinal soft tissues, with care taken to preserve any ligamentous and facet capsule architecture. Several screws were drilled into superior endplate of most cephalad vertebra and the inferior endplate of the caudal vertebrae were coupled to metal potting fixtures, with the screw-vertebra construct secured using polymethylmethacrylate (PMMA). Specimens were kept moist during the entire preparation and testing procedure.

Kinetic Analysis—Load Application and Range of Motion Determination

The specimen was attached to a custom-designed spinal testing fixture. The testing fixture wag coupled to a standard servo hydraulic testing frame (MTS) and, using a system of pulleys and tensioned wires, applies pure moments to the specimen in flexion/extension, right and left lateral bending, and right and left axial rotation. Loads were applied up to a maximum of 5 N-m, Specimens were pre-conditioned for three cycles and data will be collected on the fourth cycle.

Load-dependent three-dimensional displacements were calculated using the principles of stereophotogrammetry. Three non-collinear markers will be attached to both the inferior and superior potting fixtures and the two levels that are involved with the fusion. Three high-resolution cameras (Vicon Peak, Centennial, CO, USA) were used to detect the light reflected by these markers, and the collected data was processed with custom-designed software (Spinal Flexibility Testing Software, MFLEX) to determine the appropriate intervertebral angles across the fusion mass. The resulting data provided both neutral zone and range of motion data across the involved levels and the adjacent segments for all three bending planes.

Statistical Analysis

Statistical significance in the aforementioned parameters between treatment groups is performed using a standard one-way ANOVA with Fisher's least-significant-difference PLSD post hoc test for multiple comparisons (StatView, SAS Institute Inc. Cary, NC, USA), p-values less than 0.05 will be considered statistically significant.

Animals had plain radiographs taken lateral and craniocaudal (AP) under general anaesthesia, Radiographs were taken at the following timepoints: Day 0 (surgery) and 1, 2, 3 and at 4 months. Additionally, faxitron analysis was performed at time of sacrifice using mammography film.

Radiographs were interpreted according to the following criteria:
0 (no fusion);
1 (moderate fusion);
2 (robust interconnected fusion mass).

Results and Discussion

FIG. 17 shows STRO-3 mAb selected culture expanded allogeneic adult multipotential cells result in significant spinal fusion following administration with an HA/TCP carrier in an ovine transpedicular screw fixation spine model compared to control alone or autograft as determined by x-ray analysis. Significant spinal fusion was observed as early as 3 months and continued to increase at 4 months. This effect did not appear to be dose dependent as even the lowest dose resulted in significant spinal fusion compared to control carrier and autograft.

Figure 18:
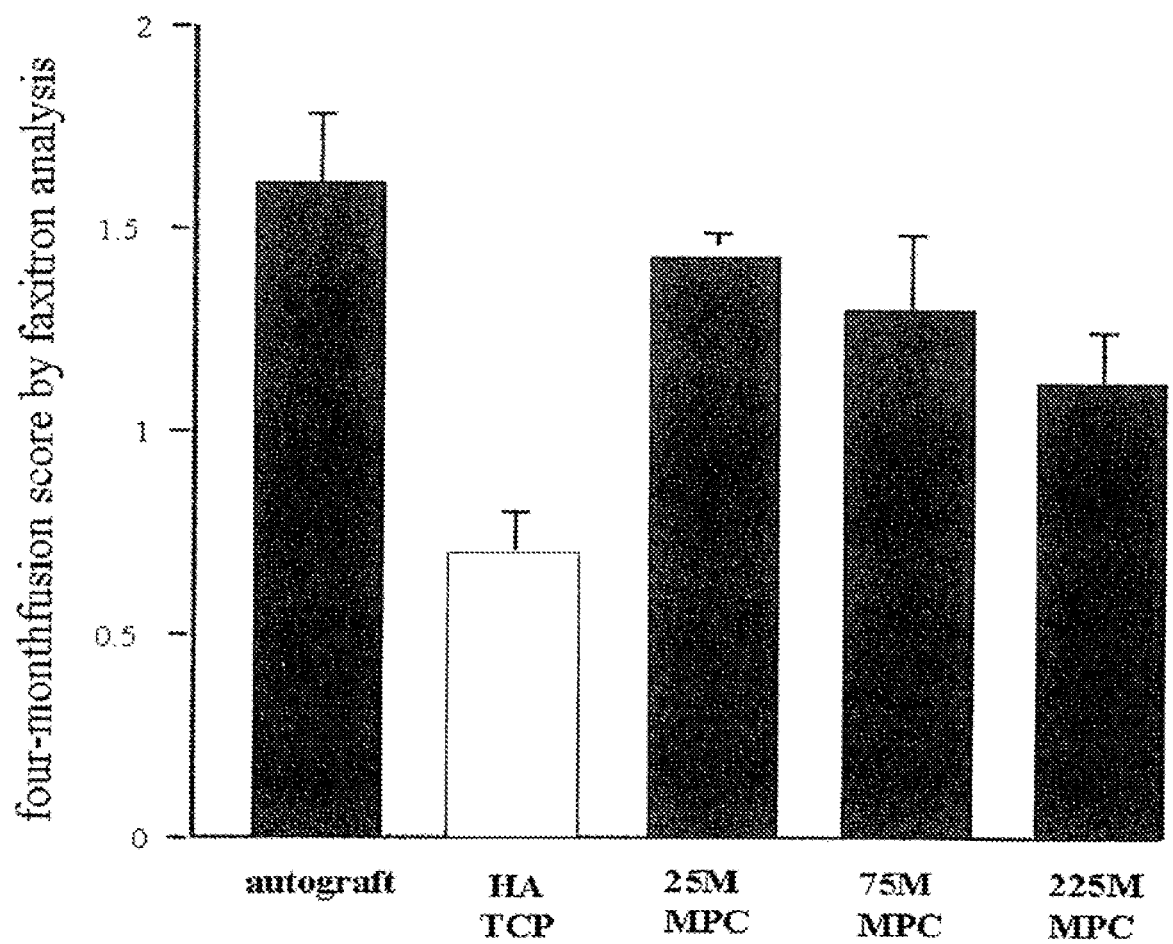

FIG. 18 shows STRO-3 mAb selected culture expanded allogeneic adult multipotential cells administered with an HA/TCP carrier in ovine transpedicular screw fixation spine model demonstrate robust spinal fusion compared to carrier controls at time of sacrifice when the instrumentation has been removed and the area assessed by fexiiron analysis using mammography film. All doses of multipotential cells demonstrate density of spinal fusion comparable to autograft standard of care.

Figure 19:
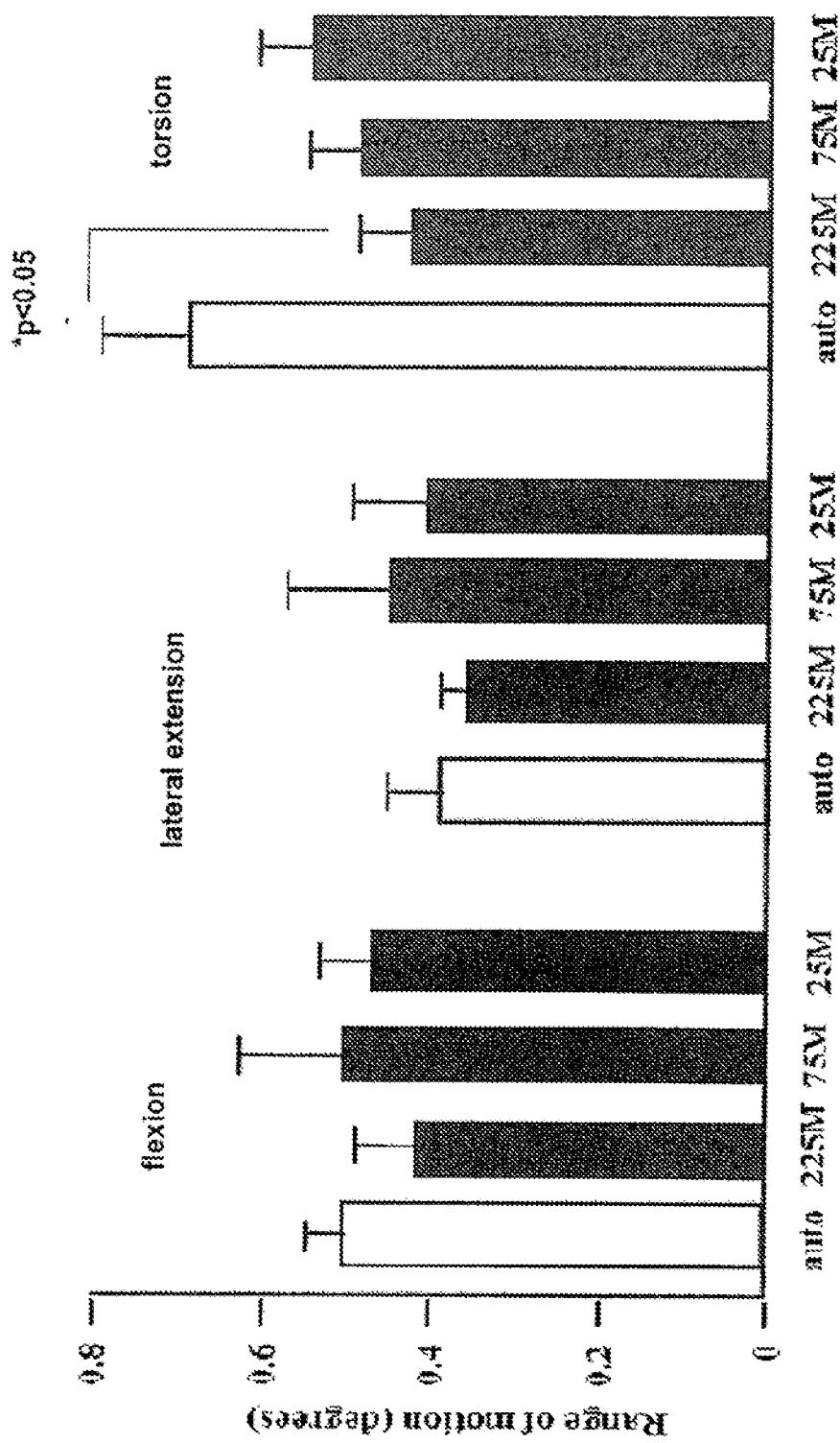

FIG. 19 shows STRO-3 mAb selected culture expanded allogeneic adult multipotential cells administered with an HA/TCP carrier in ovine transpedicular screw fixation spine model demonstrate fusion that is mechanically comparable to autograft controls. All doses of multipotential cells resulted in flexion, lateral extension and torsional range of motion mechanical loads characteristic of fused bone.

Figure 20:
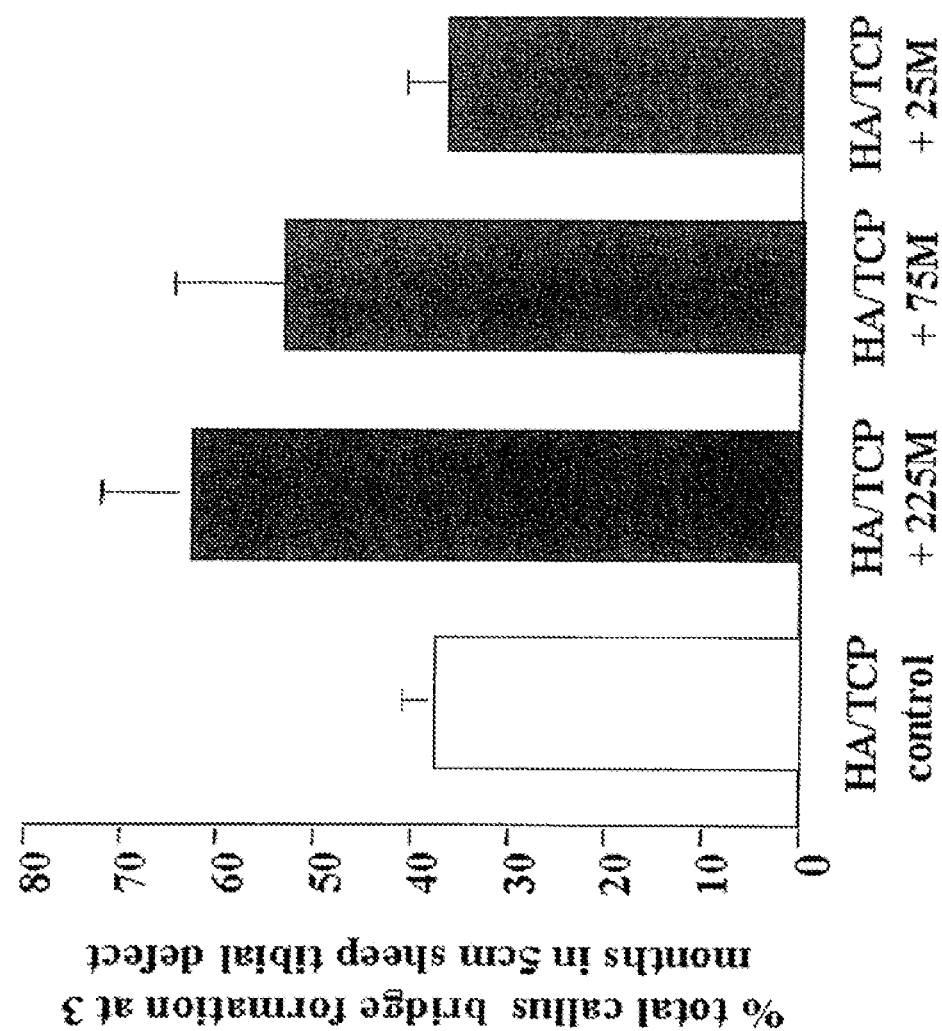

FIG. 20 shows STRO-3 mAb selected culture expanded allogeneic adult multipotential cells administered with an HA/TCP carrier in ovine critical sized 5 cm defect tibia model resulted in early bone growth in a dose dependent manner. 225M cells combined with HA/TCP carrier resulted in over 60% callus bone formation as early as 3 months following injury.

Figure 21:
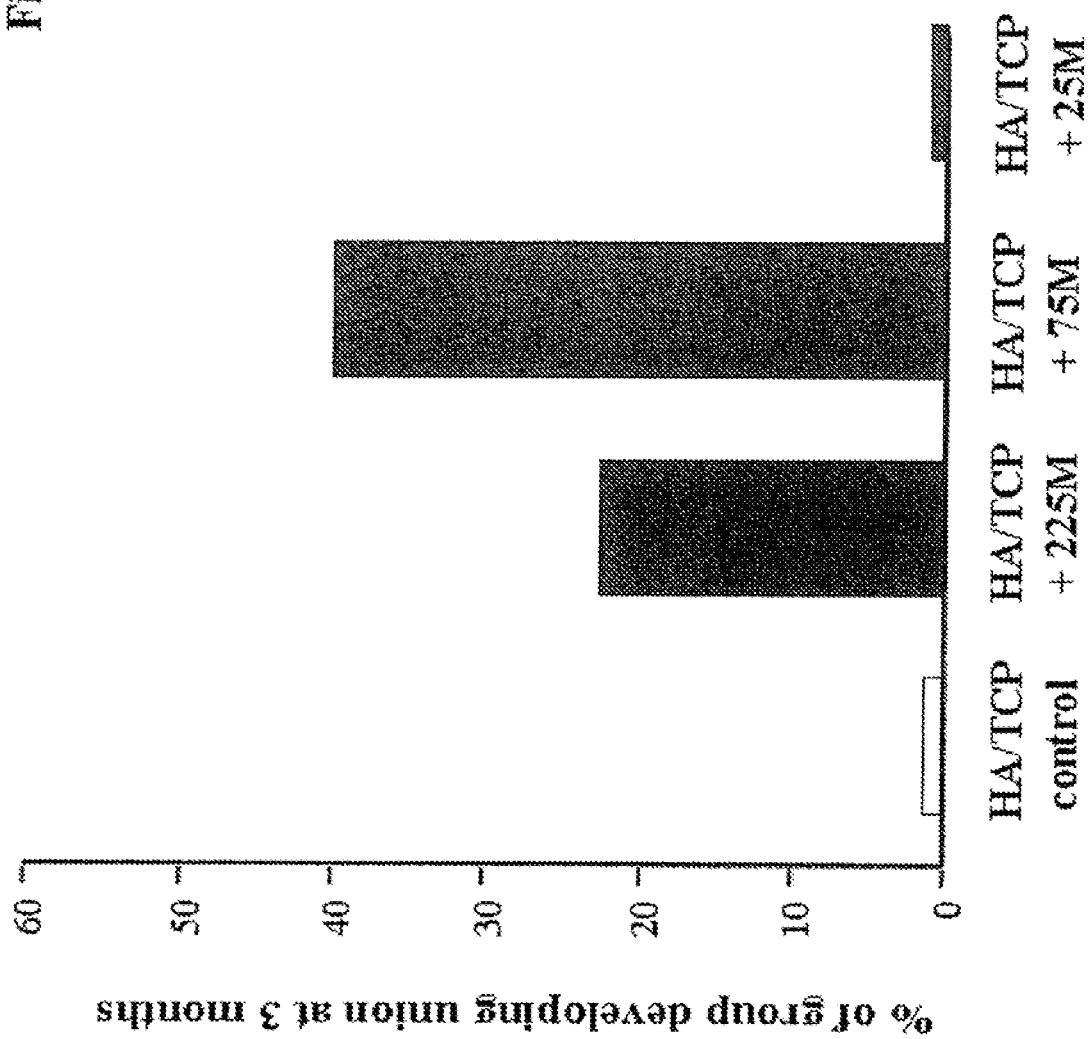

FIG. 21 shows STRO-3 mAb selected culture expanded allogeneic adult multipotential cells administered with an HA/TCP carrier in ovine critical sized 5 cm defect tibia model resulted in increased union rates compared to carrier alone control. Only the 75M and 225M cell dose resulted in union as defined by x-ray analysis at 3 months.

These results show that expanded cells of the invention are able to enhance bone repair.

Example 12: STRO-3 mAb Selected Adult Multipotential Cells Improve Cardiac Function Materials and Methods Thoracotomy Procedure For sheep, chest and upper abdomen was clipped, prepped with soap and water and painted with betadine solution which is allowed to dry. The surgical fields were draped with sterile drapes and all persons at the operating table were fully gowned, masked, gloved and capped. All thoracic operations are done through a left thoracotomy. The smallest possible incision was used and the $3^{rd}$, $4^{th}$ or $5^{th}$ interspace is entered. Skin incisions were made with scapel. Subcutaneous tissue and muscles are usually divided with cautery to improve hemostasis. The pericardium was opened and the heart supported in a pericardial cradle. An epicardial echocardiogram was performed under sterile technique. Polypropylene (#0) sutures are used to ligate the appropriate coronary arteries. The anteroapical infarction model has been well established previously in this animal model. Briefly, suture ligation of the distal ⅓ of the left anterior descending artery (LAD) along with ligation of the second diagonal coronary artery branch (D2) will uniformly create an anteroapical Infarct comprising approximately 20-25% of the left ventricle; this technique consistently and reliably produces injury which leads over time to ventricular remodeling and congestive heart failure (CHF). Thoracotomy wounds were closed with running 3-0 Vicryl suture, Skin was closed with a subcuticular suture of 3-0 Vicryl. Prior to chest closure an intercostal nerve block at the surgical site was performed with bupivacaine (5 cc of 0.25% solution). A chest tube was placed in the left pleural space and placed on 20cr αwater suction drainage until the animal is extubated.

Animals were fully monitored while under anesthesia during the procedure (eg, BP-arterial line, Cardiac output Swan-Ganz/conductance catheter). Animals are carefully watched in our laboratory for several hours post extubalion until fully awake and standing. They are closely watched for the next 6-24 hours for any arrhythmias or signs of low cardiac output and monitored and treated for pain control, fluid retention or lack of appetite as needed.

Additional thoracotomy were performed in nude rats. Left anterior descending artery ligation was performed under general anesthesia and animals were subsequently injected with cells in the perinfarct region, pericardium and wounds sutured and animals were allowed to survive for 2 weeks at which time they were sacrificed.

Administration if Adult Multipotential Cells

For sheep in intro expanded STRO-3 TOAb selected bone marrow cells or control Profreeze media was thawed in a 37 degree waterbatch. The 4 ml vial was then swabbed with alcohol and an angiocath needle syringe was then used to aspirate 1 ml volumes and transported into 4 ml syringes. A total of approximately 3.5 mls of the 4 mls was recovered. Each 1 ml syringe was then fitted with a 27 gauge needle and 0.2 ml was injected around the perinfaret borderzone via approximately 16-20 injections.

For rats, 0.2 ml of media containing one million cells was injected by 27 gauge needle at the perinfarct border zone.

Echocardiography
Laparotomy for Transdiaphragmatic Quantitative Echocardiography For sheep, at approximately baseline, immediately post-infarction, week four post-infarction each animal underwent laparotomy under full general anesthesia (isoflurane) to perform transdiaphragmatic quantitative echocardiography. A laparotomy is required because it is not possible to get adequate transthoracic or transesophageal echocardiographio images for quantitative analysis in sheep. These animals have enormous lungs that wrap around the heart entirely. The air in the lungs degrades the images substantially. During these studies hemodynamics such as blood pressure, heart rate and cardiac output were carefully monitored.

Specifically, the upper abdomen was clipped, prepped with soap and water and painted with betadine solution which is allowed to dry. The surgical field was draped with sterile drapes and all persons at the operating table were fully gowned, masked, gloved and capped. Because of overlapping lungs echocardiograms were taken from a sub-diaphragmatic view, The initial incision was made with a scalpel and carried through the subcutaneous and muscular layers with a cautery. The peritoneal cavity was opened. The echo probe was introduced under the diaphragm within a sterile plastic bag and all studies are done under sterile conditions. The incision is closed with simple interrupted 0-prolene suture through both the peritoneum and posterior fascia. The subcutaneous tissue was closed with 3-0 running Vicryl. The skin is closed with 3-0 subcuticular Vicryl.

For rats, 2D echocardiography was used to measure to systolic and diastolic volume parameters.

Data Analysis

All images were analyzed off-line. All measurements were made at end systole, identified as the frame at which LV cavity area was smallest. All plots representing three-dimensional renderings were created using Tecplot (Version 10; Amtec Engineering, Bellevue. Washington). Spline surface fits and Gaussian curvatures were calculated in Matlab. AU measurements are presented as means SD. Comparisons are made between baseline and postinfarction using paired t tests. The image processing and data analysis performed for the 2DCE data in both long and short axis has been described previously. Briefly, the endocardial curvature (K) and the ventricular wall thickness (h) were measured in the borderzone before and 1 hour after infarction. All 3DCE rotational cross-sectional images were analyzed as follows. Endocardial and epicardial contours were, traced (UTH-SCSA ImageTool; Department of Dental Diagnostic Science, University of Texas Health Science Center, San Antonio, Texas) by an echocardiography technician unaware of the hypotheses of the study.

The endocardium and epicardium were reconstructed at end systole by tracing each in every individual rotational cross-section. At each endocardial and epicardial location, the presence or absence of myocardial perfusion was determined; thereby, perfusion status was registered with LV geometry, allowing precise and unambiguous determination of borderzone myocardium. The cross sectional data were then combined to recreate a three dimensional representation of the LV endocardial and epicardial surfaces, indexed by perfusion status. The endocardial and epicardial surfaces were fit using a smoothing thin-plate spline (x), and the characteristics of this surface, including spatially resolved Gaussian curvature, were calculated.

Results and Discussion

Figure 22:
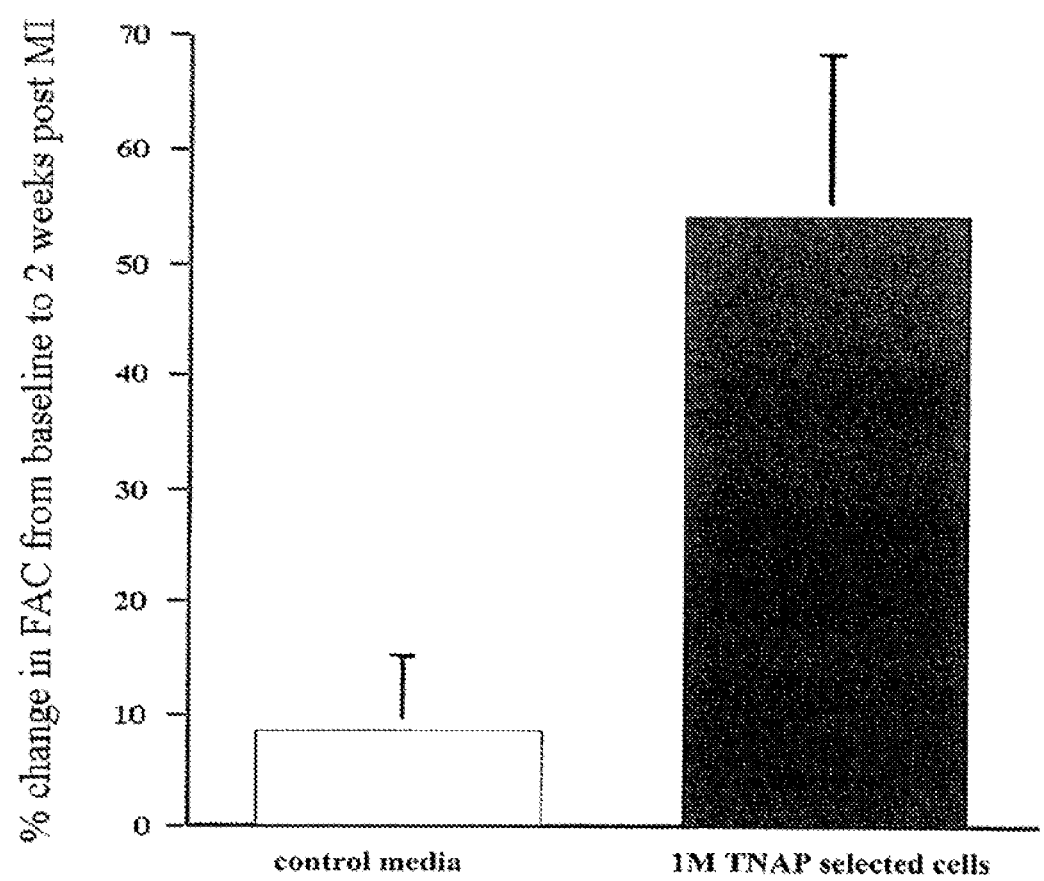

FIG. 22 shows the effects of human STRO-3 mAb selected cells following 5 passages directly injected into hearts of 5 rats 24 hours after acute ligation of the left anterior descending coronary artery. At two weeks the cells induce approximately 50% greater fractional area change compared with injection of control medium alone.

Figure 23:
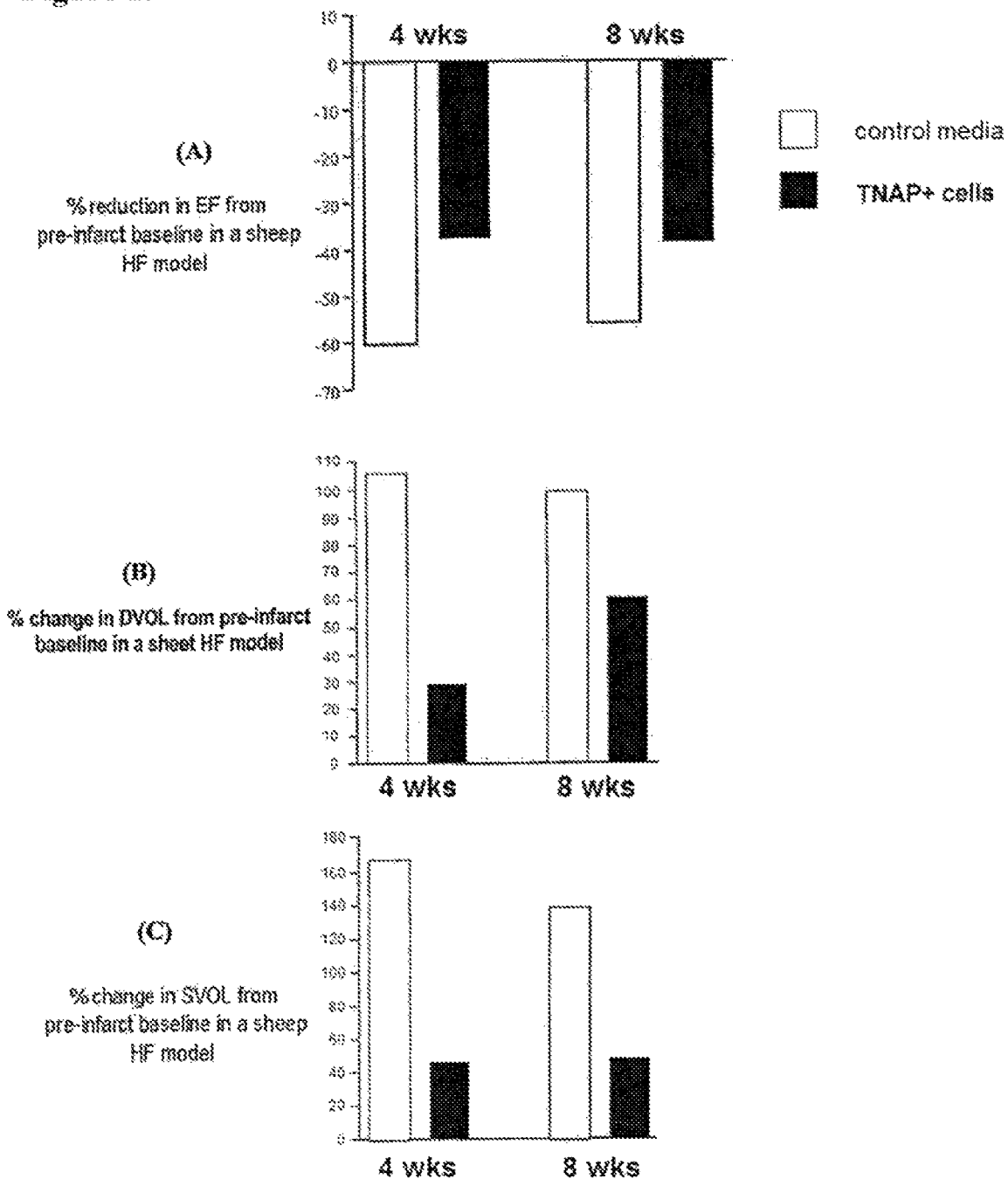

FIG. 23 shows the effects of allogeneic sheep STRO-3 mAb selected cells following 5 passages directly injected into sheep hearts immediately after acute ligation of both diagonal coronary arteries. At four and eight weeks the animals treated with STRO-3 selected cells demonstrate significantly greater ejection fraction (A), and significantly lower diastolic (B) and systolic (C) volumes, compared with animals treated with control medium alone.

These results show that expanded cells of the invention are able to improve cardiac function.

Example 13; Use of Human STRO3-Selected and Culture-Expanded TNAF Enriched Cells in Human Patients in Need of (1) Bone Regeneration, or (2) Cardiac Functional Recovery/Increase in Blood Vessel Formation Materials and Methods Standard operating protocols of Cell Therapies Pty Ltd (affiliated with Peter MacCullum Institute of Cancer Research Melbourne, Australia) were used on culture expanded STRO-3 mAb immunoselected TNAP+ cells from human-BM, enabling their subsequent in vivo use in patients in need of either bone regeneration or cardiac function/blood vessel formation.

Bone Marrow Aspiration Procedure

1. Bone Marrow (BM) is routinely taken from two or more sites approximately ½ to 1 cm apart on the back of the iliac crest (hip bone).

2. An injection of local anaesthetic is given in the skin over the hip to anaesthetise the skin area. A small cut is made in the skin and a needle is placed into the bone.

3. 5-20 ml of marrow is aspirated the needle is withdrawn and reinserted through the same skin incision into a different part of the bone, away from the previously aspirated area until 40 ml of marrow has been collected.

4. BM is routinely aspirated into Lithium-Heparin containing tubes, although other anti-coagulants are acceptable. It is preferable that the marrow aspirate is processed within 1 hour of collection, as described below.

Bone Marrow Mononuclear Preparation—Density Gradient Separation

All techniques are performed in a Biological Safety Cabinet Class 11

1. A 40 ml aspirate of BM will usually be received in 4 tubes (approx. 10 ml/tube).

2. Pool all the fractions of BM into a 50 ml tube (Falcon, Becton Dickinson) to ensure equal mixing. Divide BM volume into equal amounts into two 50 ml tubes. Add an equal volume of blocking buffer.

3. Perform a white cell estimation using white cell fluid (WCF). Assess cell number (pre-processing count).

4. Using a 70 mm cell strainer (Falcon, Becton Dickinson), strain the diluted BM into two 50 ml centrifuge tubes to remove any small clots and bone fragments.

5. Place 3 mls of Ficoll-Hypaque (Lymphoprep) solution in the bottom of tea "round bottom" 14 ml polystyrene tubes (Falcon, Becton Dickinson).

6. Carefully overlay lymphoprep with 7.5 mls of BM.

7. Centrifuge tubes at 400×g (1400 rpm) for 30 mins at RT. Ensure that the centrifuge brake is off 8. With a sterile cannula, vacuum aspirate media until approximately _ cm above the leucocyte band (buffy coat). Carefully collect the mononuclear layer with a disposable plastic Pasteur pipette and pool into a 50 ml tube.

9. Dilute cells to 40 ml with wash buffer and centrifuge sample at 400×g (1400 rpm) for 10 mins with the break on high.

10. Aspirate the buffer until just above the cell pellet Vortex the tube and add 50 ml HHF. Repeat step 9.

Magnetic Activated Cell Sorting (MACS) of TNAP Positive CeOs

1. Prior to immunolabeling, BMMNC (approximately 1-2×108 cells) are resuspended in 0.5 ml blocking buffer and incubated for 30 minutes on ice to block possible Fc receptor-mediated binding of antibodies.

2. Five hundred micro liters of STRO-3 mAb previously diluted to a concentration of 10 mg/ml in blocking buffer, is added to the BMMNC and incubated for 60 minutes at 4/C. with occasional, gentle mixing.

3. BMMNC are washed twice in HHF and resuspended in 0.5 ml of HHF containing biotiixylated goat anti-mouse IgG (g-chain specific, Southern Biotechnology Associates, Birmingham, UK) at a ⅟50 dilution and incubated at 4/C for 45 minutes.

4. The BMMNC are washed three times in MACS buffer (Ca2+- and Mn2+-free PBS supplemented with 1% BSA in PBS, 5 mM EDTA and 0.01% sodium azide) and resuspended in 450 J. of MACS buffer to which 50_1 of streptavidin microbeads (Miltenyi Biotec; Bergisch Gladbaeh, Germany) are added (10_. of microbeads/107 cells in 90 J MACS buffer). The mixture is incubated at 4/C for 15 minutes.

5. To monitor the purification process (optional), Strepavidin-PE conjugate (⅟50) (Caltag Laboratories, San Francisco, CA) is added directly to the cell suspension for an additional 5 minutes.

6. After 1 wash in ice-cold MACS buffer, a small aliquot of cells (approx. 200K) is removed for flow cytometric analysis (pre sample). The remaining cells are then be placed onto the mini MACS column (column capacity of 108 cells, Miltenyi Biotec, MS column). The TNAP− ceDs (negative fraction) are not retained within the column and pass through, under gravity into the effluent, whilst the TNAP+ cells remain, attached to the magnetised matrix.

7. Wash the column 3 times with 0.5 ml MACs buffer to remove any non-specifically bound TNAP− cells.

8. The TNAP+ cells are recovered by flushing the column with MACS buffer after withdrawing the column from the magnetic field. Small samples from each of the pre, negative and positive fractions are removed, fixed in FACS Fix (1% (v/v) formalin, 0.1 M D-glucose, 0.02% sodium azide in PBS) and subsequently analysed by flow cytometry in order to assess purity and recovery.

Establishment and Ex Vivo Culture of STRO-3 mAb Selected Cells

1. The TNAP+ enriched populations (5×104 per cm2) are cultured in tissue culture flasks or plates containing alpha-Modification of Eagle's Medium (α-MEM) supplemented with 20% foetal bovine serum, 100 mM L-ascorbate-2-phosphate, 2 mM L-glutamine, 50 U/ml penicillin and so mg/ml streptomycin (CSL) at 37/C in 4% CO2 for two weeks.

2. Primary cell populations should be passaged when the cultures achieve 80-90% confluency. Adherent cultures should be washed 1× with serum free HBSS and the cells liberated hy enzymatic digestion with 2 ml of 0.5% Trypsin/EDTA solution (IRH) per T75 flask for 5-10 minutes at 37° C. Cell suspensions are pooled and re-seeded at 0.5-1.0×104 per cm2 in α-MEM growth medium supplemented with 10% FBS.

3. Routinely, single cell suspensions of culture expanded cells are prepared by trypsin/EDTA digest as described above. The cells are then diluted and washed in cold HFF. Following centrifugation, the cell pellet is resuspended at a concentration of $5×10^6$ cells per ml in FBS and maintained on ice. An equal volume of freeze mix (20% DMSO in cold FBS) is then added gradually while gently mixing the cells to give a final concentration of 2.5×106 cells per ml in 10% DMSO/FBS. One ml aliquots are then distributed into 1.8 ml cyovials (NUNC) on ice, i.e. 1 ml per tube, then frozen at a rate of −1° C. per minute using a rate control freezer. The frozen vials are then transferred to liquid nitrogen for long-term storage. Recovery of the frozen stocks is achieved by rapid thawing the cells in a 37 bC water bath. The cells are then resuspended in cold HFF and spun at 280×g for 10 minutes. To assess viability of the cells, prepare a 1:5 dilution in 0.4% trypan blue/PBS, and the number of cells determined using a haemocytometer. Typically this procedure gives viabilities between 80-90%.

Quality Control of Cells Preparations

1. BMSSC cultures are prepared by trypsin/EDTA digest then resuspended in blocking buffer for 30 minutes.

2. Final cell qualification includes: negative gram stain, negative bacterial and fungal culture at 14 days, negative endotoxin testing, and 70% viability by trypan-blue dye exclusion.

3. Cells are characterised by immunophenotype STRO-1+, TNAP+, CD146+, CD44+, CD3−, CD14−, colony forming assays (Colony Forming Units-Fibroblasts (CFU-F), and induced osteoblast differentiation).

Autologous culture-expanded cells are then couriered, on ice, to the Royal Melbourne Hospital, Melbourne, Australia, for implantation in patients in need of bone regeneration, and to the John Hunter Hospital in Newcastle, Australia, for intrarayocardial implantation in patients in need of cardiac functional recovery and/or new blood vessel formation.

Percutaneous NOGA-Guided Bone Marrow Cell Implantation Procedure

The NOGA (Biosense) left ventricular electromechanical mapping system utilises magnetic technology to navigate an 8fr endocardial-mapping catheter, which is introduced percutaneously via the right femoral artery and advanced into the left ventricle. The catheter is then dragged along the endocardial surface, acquiring local R wave electrical potentials. The electrical signals are gated to surface ECG electrodes, thereby providing information on regional wall motion (local linear shortening scores). Areas of ischaemic but viable myocardium will be detected by NOGA as a region of reduced local linear shortening but preserved R wave potential. The pre-defined NOGA parameters of normal myocardium is areas of electrical activity >5 mV and local linear shortening >12%. Infracted myocardium will have areas of electrical activity <5 mV and local linear shortening <4%. Ischaemic but viable myocardium will have an electrical potential of 5 mV or greater and local linear shortening scores of 4-12%. The NOGA has been extensively validated as a tool for assessing myocardial viability on line in the Cardiac Catheteiisation Laboratory. The Biosense Myo-Star™ injection catheter is similar to the mapping catheter as it has a magnetic sensor at its tip, which makes it locatable in space. It has a retractable needle, which can be used to accurately inject the bone marrow cells into the target region. This system enables accurate and safe injection of the bone marrow cells into the endocardium as it makes contact with the endocardial surface.

Results and Discussion

Implantation of STRO3-Selected and Culture-Expanded TNAP-Enriched Cells in a Patient with a Non-Union Fracture of the Femur A 19-year-old male presented to Hie Royal Melbourne Hospital with a fracture of the femoral shaft which had occurred 9 months earlier due to a motorcycle accident and had failed to heal despite surgical implantation of rods and screws. A persistent, non-healing 5 cm defect persisted.

Following informed consent, the patient underwent a bone marrow aspirate, with STRO-3 mAb selection of the bone marrow mononuclear cells, and culture-expansion of these cells, as above. After approximately six weeks of culture, 200-225 million cells were harvested and prepared for infusion surgically.

At infusion, cells were resuspended into sterile, ealine/plasmalyte to a 5-10 ml volume and mixed with the Artificial Synthetic Bone Matrix (HA/TCP) containing bovine collagen (Mastergraft™ Matrix).

The procedure was uneventful, with no adverse events, and the defect was fully closed.

Implantation of STRO3-Selected and Culture-Expanded TNAP-Enriched Cells in Two Patients with Multiple Coronary Artery Vessel Occlusions and Refractory Chest Pain Two males age ranges 40-65 years presented to the John Hunter Hospital with persistent chest pain on exertion and multivessel coronary artery occlusions, not amenable to medical or surgical treatment.

Following informed consent, the patients underwent a bone marrow aspirate, with STRO-3 mAb selection of the bone marrow mononuclear cells, and culture-expansion of these cells, as above. After approximately six weeks of culture, 100-120 million cells were harvested for each patient and prepared for mtramyocardial infusion by NOGA (Biosense) cardiac catheter.

For each patient, NOGA catheter-guided intramyocardial injection of the cultured cells was performed. At each target region, 10-12 injection of 0.2 m containing cells was performed.

Echocardiograms were performed during and immediately after the procedure in order to exclude perforation of the ventricular wall and ensuing pericardial tamponade. After the procedure, patients were observed for 24 hours in the Coronary Care Unit. Electrocardiograms and cardiac enzyme levels were tested every 8 hours during Coronary Care Unit observation. Echocardiograms were obtained in the first 24 hrs after implantation procedure.

No adverse events were observed either acutely or in the post-operative period. The patients have each been followed for two months. During this period, each patient has indicated reduced frequency and severity in episodes of chest pain and reported increased exertional tolerance.

These data suggest that implantation of the expanded cells has resulted in increased vascular blood flow to the damaged and "at risk" areas of myocardium supplied by the occluded coronary vessels.

Example 14: Increased Cell Survival when Delivered with Fibrin Glue

Materials and Methods
Preparation of Fibrin Glue

Fibrin Glue (Tisseal VH, Baxter) was prepared according to manufacturer specification. Briefly, the vials containing the freeze-dried Sealer Protein Concentrate, the Fibrinolysis Inhibitor Solution, and the thrombin were heated in a waterbath to 37° C. The Fibrinolysis Inhibitor Solution was transferred into the vial containing the freeze-dried Sealer Protein Concentrate using the sterile reconstitution components provided with the DUPLOJECT Preparation and Application System. The vial was allowed to stand at 37° C. for one minute then swirled briefly and vigorously with a circular motion (avoiding excessive frothing) and placed into a water-bath for another 15 minutes. The calcium chloride solution was transferred to the thrombin solution once warmed.

Resuspension and Injection of Cells

Five million culture expanded immunoselected human MPCs in PBS were transferred to the diluted thrombin solution. The thrombin/cell solutions and reconstituted Sealer Protein solutions were then loaded into a modified DUPLOJECT Application system loaded with two needleless, Ice insulin syringes (Beckton Dickinson) and a 27G ⅝" needle (Beckton Dickinson).

Forty-eight hours after LAD ligation and infarction of nude rats, the left thoracotomy incision was reopened and adhesions were carefully lysed. The infarct zone was identified and 0.3 cc total volume (containing I million cells in 1:5 diluted fibrin glue) was injected in three, equal divided doses into the peri-infaret region. The incision was closed in layers and the animal recovered. Following a further forty-eight hours animals were sacrificed, cardiac tissue obtained and total DNA was extracted by standard methods.

PCR of human β-globulin gene was performed on rat extracted cardiac tissue DNA to estimate human cell survival from standard curves.

Results and Discussion

FIG. 24 shows that culture expanded MPCs of the invention demonstrate increased survival in tissues in vivo when delivered in fribrin glue.

It will be appreciated by persons skilled in the art that numerous variation and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Allcock et al. (1977) Synthesis of Poly[(amino acid alkyl ester)phosphazenes] *Macromolecule* 10, 824-830.

Anseth et al (2002) In situ forming degradable networks and their application in tissue engineering and drug delivery. *J Control Release* 78, 199-209.

Bianco et al. (2001). Bone marrow stromal stem cells: nature, biology, and potential applications. *Stem Cells* 19, 180-92, Bregni et al. (1992). Human peripheral blood hematopoietic progenitors are optimal targets of retroviral-mediated gene transfer. *Blood* 80, 1418-22.

Chatterjee et aL (1996) Adeno-associated virus vectors for gene therapy of the hematopoietic system. *Curr Top Microbiol Immunol* 218, 61-73.

Cole et al. (1984) Human monoclonal antibodies. *Mol. Cell Biochem.* 62, 109-20.

Cote et al. (1983) Generation of human monoclonal antibodies reactive with cellular antigens. *Proc. Natl Acad. Sci. USA* 80, 2026-30

Danos et al. (1988) Safe and efficient generation of recombinant retroviruses with amphotropic and ecotropic host ranges. *Proc. Natl. Acad. Sci. USA.* 85, 6460-4

De Broe et al. (1992). Introduction: recent developments in alkaline phosphatase research—*Clin Chem* 38, 2485.

Dennis et al. (2002). The STRO-1+ marrow cell population is multipotential. *Cells Tissues Organs* 170, 73-82.

Ducy et al. (1997). Osf2/Cbfa1: a transcriptional activator of osteoblast differentiation. Cell 89, 747-54.

Finer et al. (1994) kat: a high-efficiency retroviral transduction system for primary human T lymphocytes. *Blood.* 83, 43-50.

Frey et al. (1998) High-efficiency gene transfer into ex vivo expanded human hematopoietic progenitors and precursor cells by adenovirus vectors. *Blood* 91, 2781-92.

Fukushi et al. (1998), Intracellular retention and degradation of tissue-nonspecific alkaline phosphatase with a Gly317→Asp substitution associated with lethal hypophophotasia. *Biochem. Biophys. Res. Commun.* 246, 613-8.

Gronthos et al. (1994). The STR.O-1+ fraction of adult human bone marrow contains the osteogenic precursors. *Blood* 84, 4 164-73.

Gronthos et al (2000). Postnatal human dental pulp stem cells (DPSCs) in vitro and in vivo. *Proc Natl Acad Sci USA* 97, 13625-30-

Gronthos et al. (1995). The growth factor requirements of STRO-1-positive human bone marrow stromal precursors under serum-deprived conditions in vitro. *Blood* 85, 929-40.

Gronthos et al. (1996). The biology and application of human bone marrow stromal cell precursors—*J Henatother S,* 15-23.

Gronthos et al. (1999). Differential cell surface expression of the STRO-1 and alkaline phosphatase antigens on discrete developmental stages in primary cultures of human bone cells. *J Bone Miner Res* 14, 47-56.

Gronthos et al. (2003). Molecular and cellular characterisation of highly purified stromal stem cells derived from human bone marrow. *J Cell Sci* 116, 1827-35.

Harris (1990) The human alkaline phosphatases: what we know and what we don't know. *Clin. Chim. Acta* 186, 133-50.

Hooper (1997). Glycosyl-phosphatidylinositol anchored membrane enzymes. *Clin. Chim. Acta* 266, 3-12.

Hutmacher et al (2001) Scaffold design and fabrication technologies for engineering tissues—state of the art and future perspectives. *J Biomater Sci Polym Ed* 12, 107-124.

Kohler et al. (1975). Continuous cultures of fused cells secreting antibody of predefined specificity. *Nature* 256, 495-7.

Kozbor et al. (1985). Specific immunoglobulin production and enhanced tumorigenicity following ascites growth of human hybridomas. J. Immunol. Methods 81, 31-42.

Magnusson et al. (2002). Monoclonal antibodies against tissue-nonspecific alkaline phosphatase. Report of the ISOBM TD9 workshop. *Tumour Biol* 23, 228-48.

McComb et al. (1979). Alkaline Phosphatases, Plenum Press, New York.

Miller et al. (1986) Redesign of retrovirus packaging cell lines to avoid recombination leading to helper virus production. *Mol Cell Biol:* 6, 2895-902.

Miller et al. (1989) Improved retroviral vectors for gene transfer and expression. *Biotechniques.* 7, 980-82, 984-86, 989-990.

Miura et al (1994) Differences between the sugar moieties of liver- and bone-type alkaline phosphatases: are-evaluation, *Ann. Clin. Biochem.* 31, 25-30.

Mornet et al. (2001). Structural evidence for a functional role of human tissue nonspecific alkaline phosphatase in bone mineralization. *J. Biol. Chem.* 276, 31171-8.

Moss (1992). Perspectives in alkaline phosphatase research. *Clin Chem* 38, 2486-92.

Mulivor et al. (1985), Quantitative analysis of alkaline phosphatases in serum and amniotic fluid: comparison of biochemical and immunologic assays. *J. Lab. Clin Med.* 105, 342-8.

Nosjean et al. (1997). Human tissue non-specific alkaline phosphatases: sugar-moiety-induced enzymic and antigenic modulations and genetic aspects. *Biochemn. J.* 321, 297-303.

Oda et al. (1999). A general method for rapid purification of soluble versions of glycosylphosphatidylinosito-anchored proteins expressed in insect cells: an application for human tissue-nonspecific alkaline phosphatase. *J. Biochetn. (Tokyo)* 126, 694-9.

Owen et al. (1988). Stromal stem cells: marrow-derived osteogenic precursors. *Qba Found Symp* 136, 42-60.

Pear et al. (1993) Production of High-Titer Helper-Free Retroviruses by Transient Transfection. *Proc Nat Acad Set USA.* 90, 8392-8396.

Pearson et al. (1988). Improved tools for biological sequence comparison. *Proc, Natl. Acad. Sci. USA* 85, 24444-g.

Prockop (1997). Marrow stromal cells as stem cells for nonhematopoietic tissues. *Science* 216, 71-4.

Quesenbery et al—(eds) (1998) Stem Cell Biology and Gene Therapy, John Wiley & Sons.

Rucker et al. (1996) Regions in beta-chemokine receptors CCR5 and CCR2b that determine HIV-I cofactor specificity. *Cell* 87, 437-46.

Sato et al. (1994). Preferential usage of the bone-type leader sequence for the transcripts of liver/bone/kidney-type alkaline phosphatase gene in neutrophilic granulocytes. *Blood* 83, 1093-101.

Simmons et al—(1991). Identification of stromal cell precursors in human bone marrow by a novel monoclonal antibody, STRO-I. *Blood* 78, 55-62.

Stewart et al. (1999). Further characterization of cells expressing STRO-1 in cultures of adult human bone marrow stromal cells. *J Bone Miner Res* 14, 1345-56.

Wang et al. (2003) Synthesis and characterization of a novel degradable phosphate-containing hydrogel. *Biomaterials* 24.3969-3980.

Weiss et al. (1986). Isolation and characterization of a cDNA encoding a human liver/bone/kidney-type alkaline phosphatase, *Proc. Nat. Acad. Sci. USA S*3, 7182-6.

Weiss et al. (1988). Structure of the human Liver/bone/kidney alkaline phosphatase gene. *J Biol Chem* 263, 12002-10, Whyte (1994). Hypophosphotasïa and the role of alkaline phosphatase in skeletal mineralization. *Endocr Rev* 15, 439-61.

Xu et al, (1994). Correction of the enzyme deficiency in hematopoietic cells of Gaucher patients using a clinically acceptable retroviral supernatant transduction, protocol. *Exp. Hemat.* 22, 223-30.

Zannettino et al. (1996)—A powerful new technique for isolating genes encoding cell surface antigens using retroviral expression cloning. *J Immunol* 156, 611-20.

Zannettino et al. (1998) The sialomucin CD164 (MGC24V) is an adhesive glycoprotein expressed by human hematopoietic progenitors and bone marrow stromal cells that serves as a potent negative regulator of hematopoiesis. *Blood* 92, 2613-28.

The invention claimed is:

1. A cell population comprising multipotential cells enriched for TNAP+multipotential cells, wherein at least 4% of the total cell population are TNAP+, STRO-1+multipotential cells capable of being cultured in vitro to produce adipocytes, osteocytes and chondrocytes and wherein the TNAP+STRO-1+multipotential cells include a TNAP+ marker which binds to the STRO-3 antibody produced by the hybridoma cell line deposited under ATCC Accession Number PTA-7282.

2. A method of generating a committed cell population of a specific tissue type, the method comprising culturing a cell population comprising multipotential cells according to claim 1 in the presence of one or more stimulatory factors; and subjecting said cultured population to conditions biasing differentiation of the multipotential cells to the specific tissue type.

3. A method for generating or repairing a tissue in a subject in need thereof, the method comprising administering to the subject the enriched cell population according to claim 1 so as to generate or repair the tissue.

4. A composition comprising the cell population comprising multipotential cells enriched for TNAP+multipotential cells according to claim 1.

5. A method for generating or repairing a tissue in a subject in need thereof, the method comprising administering to the subject the composition according to claim 4 so as to generate or repair the tissue.

6. The cell population comprising multipotential cells enriched for TNAP+multipotential cells according to claim 1, wherein the STRO-1+ cells are STRO-1$^{bright}$ cells.

7. A composition comprising the cell population comprising multipotential cells enriched for TNAP+multipotential cells according to claim 6.

8. A method of generating a committed cell population of a specific tissue type, the method comprising culturing a cell population comprising multipotential cells according to claim 6 in the presence of one or more stimulatory factors; and subjecting said cultured population to conditions biasing differentiation of the multipotential cells to the specific tissue type.

9. A method for generating or repairing a tissue in a subject in need thereof, the method comprising administering to the subject the enriched cell population according to claim 6 so as to generate or repair the tissue.

10. The cell population comprising multipotential cells enriched for TNAP+multipotential cells according to claim 1, wherein at least 10% of the total cell population are TNAP+, STRO-1+multipotential cells capable of being cultured in vitro to produce adipocytes, osteocytes and chondrocytes.

11. The cell population comprising multipotential cells enriched for TNAP+multipotential cells according to claim 10, wherein the STRO-1+ cells are STRO-1$^{bright}$ cells.

12. A composition comprising the cell population comprising multipotential cells enriched for TNAP+multipotential cells according to claim 10.

13. A method of generating a committed cell population of a specific tissue type, the method comprising culturing a cell population comprising multipotential cells according to claim 10 in the presence of one or more stimulatory factors; and subjecting said cultured population to conditions biasing differentiation of the multipotential cells to the specific tissue type.

14. A method for generating or repairing a tissue in a subject in need thereof, the method comprising administering to the subject the enriched cell population according to claim 10 so as to generate or repair the tissue.

15. The cell population comprising multipotential cells enriched for TNAP+multipotential cells according to claim 10, wherein at least 20% of the total cell population are TNAP+, STRO-1+multipotential cells capable of being cultured in vitro to produce adipocytes, osteocytes and chondrocytes.

16. The cell population comprising multipotential cells enriched for TNAP+multipotential cells according to claim 15, wherein the STRO-1+ cells are STRO-1$^{bright}$ cells.

17. A composition comprising the cell population comprising multipotential cells enriched for TNAP* multipotential cells according to claim 15.

18. A method of generating a committed cell population of a specific tissue type, the method comprising culturing a cell population comprising multipotential cells according to claim 15 in the presence of one or more stimulatory factors; and subjecting said cultured population to conditions biasing differentiation of the multipotential cells to the specific tissue type.

19. A method for generating or repairing a tissue in a subject in need thereof, the method comprising administering to the subject the enriched cell population according to claim 15 so as to generate or repair the tissue.

20. A method of obtaining a cell population comprising multipotential cells enriched for TNAP+, STRO-1+multipotential cells which comprises contacting the multipotential cells with a STRO-3 antibody produced by the hybridoma cell line deposited under ATCC Accession Number PTA-7282 under binding conditions, recovering the multipotential cells to which the STRO-3 antibody binds, and then separately recovering the multipotential cells to which the STRO-3 antibody bound.

\* \* \* \* \*